United States Patent
Barrat

(10) Patent No.: US 11,197,890 B2
(45) Date of Patent: Dec. 14, 2021

(54) METHODS OF TREATING CANCER, INFECTIOUS DISEASE, AND AUTOIMMUNE DISEASE USING CXC CHEMOKINES

(71) Applicant: NEW YORK SOCIETY FOR THE RUPTURED AND CRIPPLED MAINTAINING THE HOSPITAL FOR SPECIAL SURGERY, New York, NY (US)

(72) Inventor: Franck Barrat, New York, NY (US)

(73) Assignee: New York Society for the Relief of the Ruptured and Crippled, maintaining the Hospital for Special Surgery, New York, NY (US)

( * ) Notice: Subject to any disclaimer, the term of this patent is extended or adjusted under 35 U.S.C. 154(b) by 259 days.

(21) Appl. No.: 15/839,105

(22) Filed: Dec. 12, 2017

(65) Prior Publication Data

US 2018/0193382 A1    Jul. 12, 2018

Related U.S. Application Data

(60) Provisional application No. 62/433,038, filed on Dec. 12, 2016, provisional application No. 62/492,562, filed on May 1, 2017.

(51) Int. Cl.
| | |
|---|---|
| *A61K 35/15* | (2015.01) |
| *A61K 38/19* | (2006.01) |
| *A61P 17/00* | (2006.01) |
| *A61K 45/06* | (2006.01) |
| *A61P 37/00* | (2006.01) |
| *A61P 35/00* | (2006.01) |
| *A61K 31/00* | (2006.01) |

(52) U.S. Cl.
CPC .............. *A61K 35/15* (2013.01); *A61K 31/00* (2013.01); *A61K 38/195* (2013.01); *A61K 45/06* (2013.01); *A61P 17/00* (2018.01); *A61P 35/00* (2018.01); *A61P 37/00* (2018.01)

(58) Field of Classification Search
CPC ...... A61K 35/15; A61K 38/195; A61K 45/06; A61P 35/00
See application file for complete search history.

(56) References Cited

PUBLICATIONS

By Bon et al (NEJM, 370:433-443, 2014) (Year: 2014).*
Wang et al (PNAS E7240-7249, published online Oct. 31, 2016) (Year: 2016).*
Barrat et al., Nucleic Acids of Mammalian Origin Can Act as Endogenous Ligands for Toll-like Receptors and May Promote Systemic Lupus Erythematosus. *J Exp Med* 202, 1131-1139 (Oct. 17, 2005).
Chia et al., Dendritic cells maintain dermal adipose-derived stromal cells in skin fibrosis. *J Clin Invest* 126, 4331-4345 (Nov. 2016).
Demaria et al., TLR8 deficiency leads to autoimmunity in mice. *J Clin Invest* 120, 3651-3662 (Oct. 2010).
Duramad et al., IL-10 regulates plasmacytoid dendritic cell response to CpG-containing immunostimulatory sequences. *Blood* 102, 4487-4492 (Dec. 15, 2003).
Guiducci et al., Autoimmune skin inflammation is dependent on plasmacytoid dendritic cell activation by nucleic acids via TLR7 and TLR9. *J Exp Med* 207, 2931-2942 (Dec. 20, 2010).
Guiducci et al., RNA recognition by human TLR8 can lead to autoimmune inflammation. *J Exp Med* 210, 2903-2919 (Nov. 25, 2013).
Guiducci et al., PI3K is critical for the nuclear translocation of IRF-7 and type I IFN production by human plasmacytoid predendritic cells in response to TLR activation. *J Exp Med* 205, 315-322 (Feb. 18, 2008).
Guiducci et al., Properties regulating the nature of the plasmacytoid dendritic cell response to Toll-like receptor 9 activation. *J Exp Med* 203, 1999-2008 (Aug. 7, 2006).
Hochberg, Updating the American College of Rheumatology revised criteria for the classification of systemic lupus erythematosus. *Arthritis Rheum* 40, 1725 (Sep. 1997).
Lafyatis et al., B cell depletion with rituximab in patients with diffuse cutaneous systemic sclerosis. *Arthritis Rheum* 60, 578-583 (Feb. 2009).
Mayes et al., Prevalence, incidence, survival, and disease characteristics of systemic sclerosis in a large US population. *Arthritis Rheum* 48, 2246-2255 (Aug. 2003).
Rice et al., A longitudinal biomarker for the extent of skin disease in patients with diffuse cutaneous systemic sclerosis. *Arthritis & rheumatology* 67, 3004-3015 (Nov. 2015).
Rowland et al., Early, transient depletion of plasmacytoid dendritic cells ameliorates autoimmunity in a lupus model. *J Exp Med* 211, 1977-1991 (Jul. 25, 2014).
Sisirak et al., Genetic evidence for the role of plasmacytoid dendritic cells in systemic lupus erythematosus. *J Exp Med* 211, 1969-1976 (Jul. 10, 2014).
Van den Hoogen et al., 2013 classification criteria for systemic sclerosis: an American College of Rheumatology/European League against Rheumatism collaborative initiative. *Arthritis Rheum* 65, 2737-2747 (Nov. 2013).
Varga and Abraham, Systemic sclerosis: a prototypic multisystem fibrotic disorder. *J Clin Invest* 117, 557-567 (Mar. 2007).
Wenzel and Tuting, An IFN-Associated Cytotoxic Cellular Immune Response against Viral, Self-, or Tumor Antigens Is a Common Pathogenetic Feature in "Interface Dermatitis". *J Invest Dermatol* 128, 2392-2402 (Apr. 17, 2008).
Yamamoto et al., Animal model of sclerotic skin. I: Local injections of bleomycin induce sclerotic skin mimicking scleroderma. *J Invest Dermatol* 112, 456-462 (Apr. 1999).

(Continued)

*Primary Examiner* — Lei Yao
(74) *Attorney, Agent, or Firm* — Leason Ellis LLP

(57) ABSTRACT

The current invention is related to the prevention and treatment of diseases including cancer, autoimmune disease, and infectious disease using CXC chemokines and the receptors to which they agonize. It has been found that certain chemokines, including CXCL4, CXCL9, CXCL10, and CXCL12 have various effects on toll-like receptors in various cell types and these can be utilized for disease treatment and prevention.

10 Claims, 48 Drawing Sheets

Specification includes a Sequence Listing.

(56) References Cited

PUBLICATIONS

Yamamoto and Nishioka, Role of monocyte chemoattractant protein-1 and its receptor,CCR-2, in the pathogenesis of bleomycin-induced scleroderma. *J Invest Dermatol* 121, 510-516 (Sep. 2003).
Batteux et al., New insights on chemically induced animal models of systemic sclerosis. *Current opinion in rheumatology* 23, 511-518 (Nov. 2011).
Blanco et al., Induction of dendritic cell differentiation by IFN-alpha in systemic lupus erythematosus. *Science* 294, 1540-1543 (Nov. 16, 2001).
Cederblad et al., Patients with systemic lupus erythematosus have reduced numbers of circulating natural interferon-alpha-producing cells. *J Autoimmun* 11, 465-470 (Oct. 1998).
Van Bon et al., Proteome-wide analysis and CXCL4 as a biomarker in systemic sclerosis. *N Engl J Med* 370, 433-443 (Jan. 30, 2014).
Guiducci et al., TLR recognition of self nucleic acids hampers glucocorticoid activity in lupus. *Nature* 465, 937-941 (Jun. 17, 2010).
Huang et al., Nintedanib inhibits fibroblast activation and ameliorates fibrosis in preclinical models of systemic sclerosis. *Ann Rheum Dis* 75, 883-890 (2016). Published Online Apr. 9, 2015.
Koca et al., Effectiveness of etanercept in bleomycin-induced experimental scleroderma. *Rheumatology* (Oxford) 47, 172-175 (Jan. 3, 2008).
LeRoy and Medsger, Jr., Criteria for the classification of early systemic sclerosis. *J Rheumatol* 28, 1573-1576 (Jul. 2001).
Tan et al., Signatures of differentially regulated interferon gene expression and vasculotrophism in the peripheral blood cells of systemic sclerosis patients. *Rheumatology* (Oxford) 45, 694-702 (Jan. 17, 2006).

\* cited by examiner

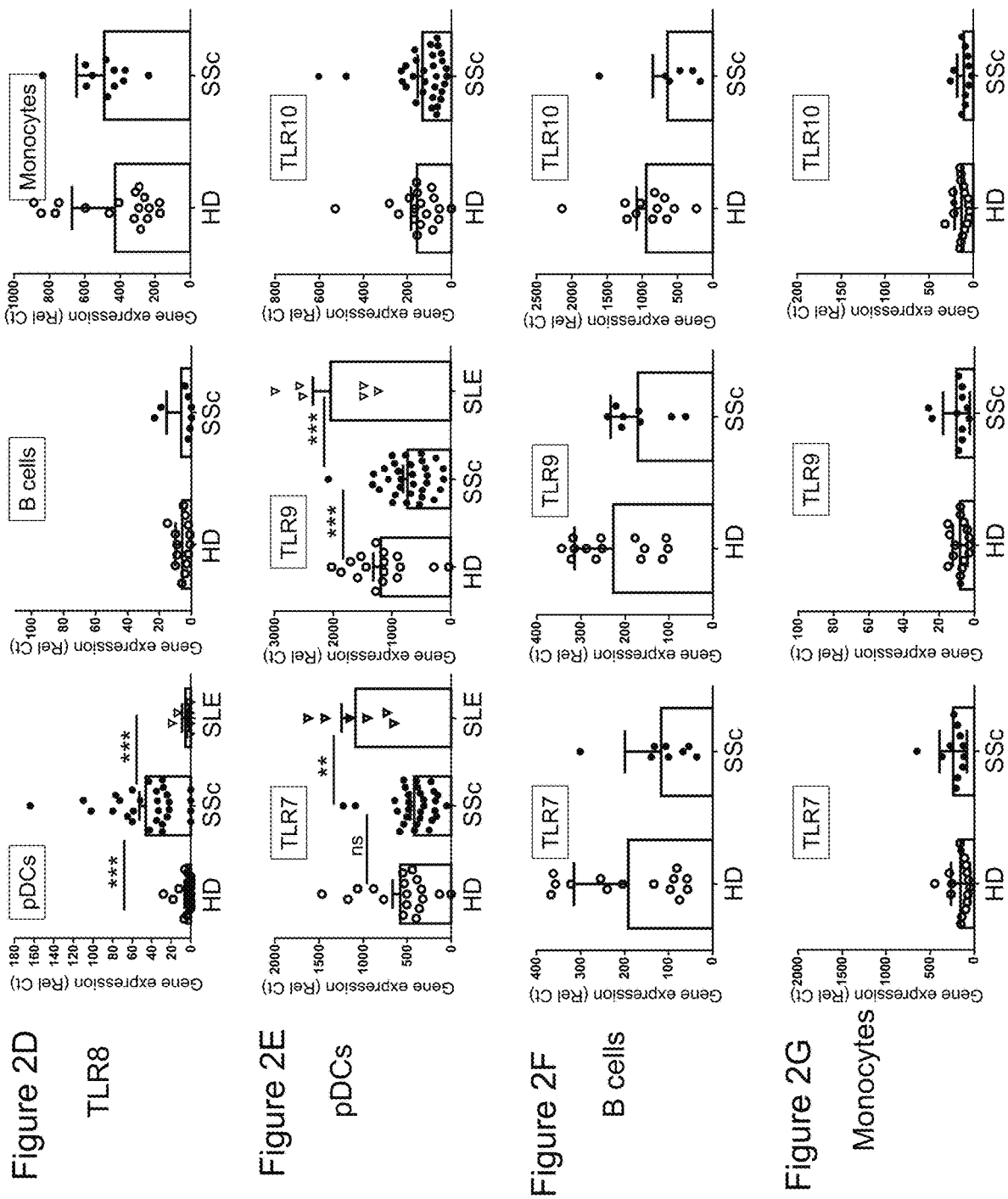

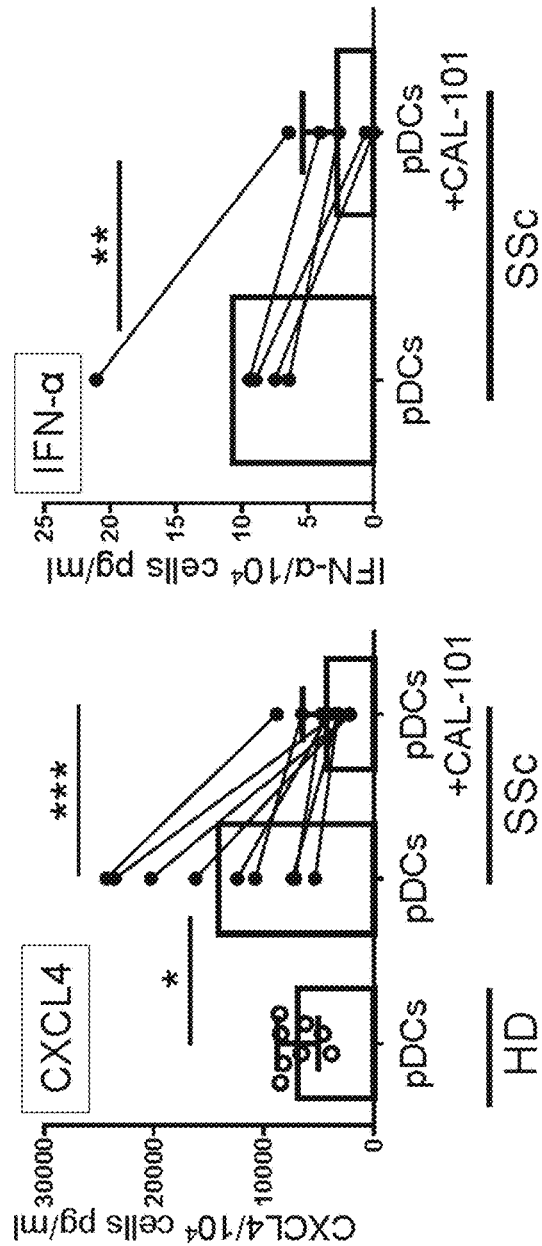
Figure 4C
Figure 4D
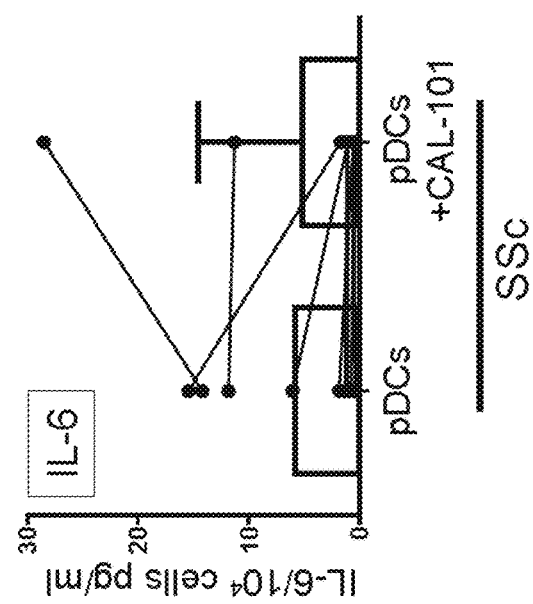
Figure 4E

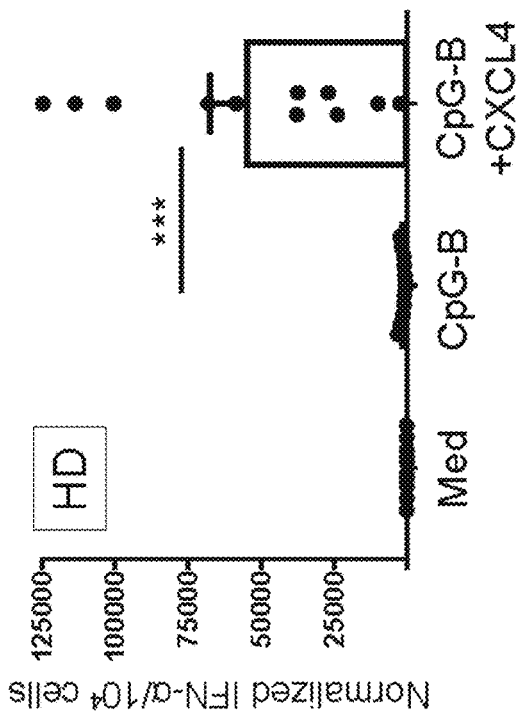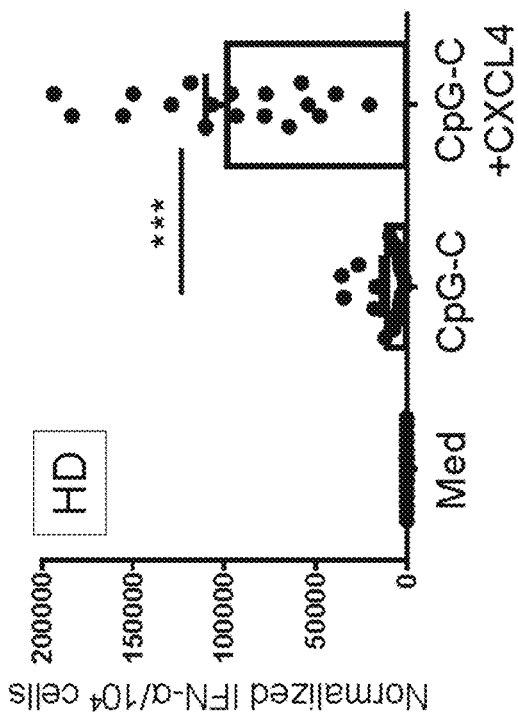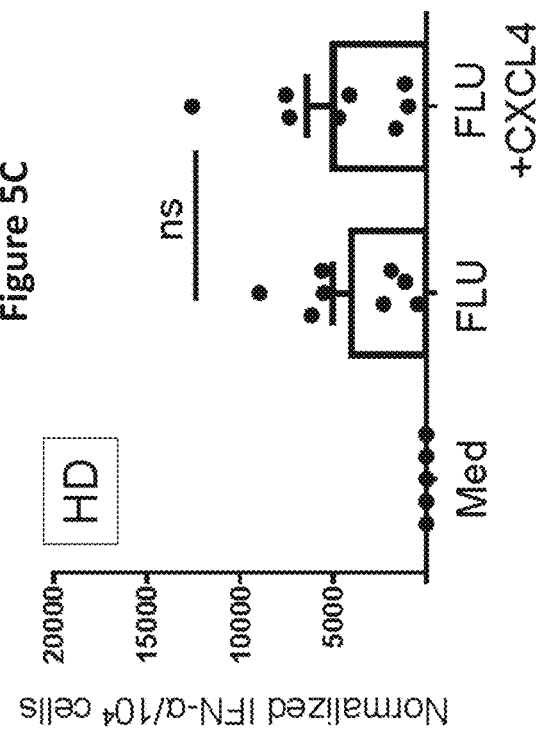
Figure 5A
Figure 5B
Figure 5C

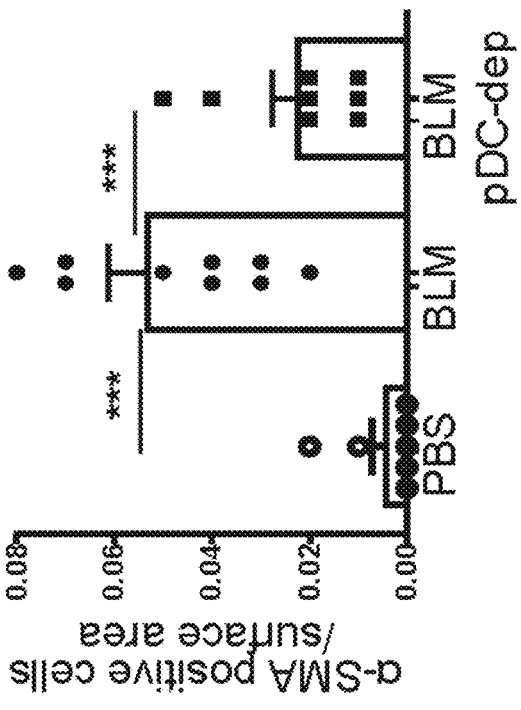
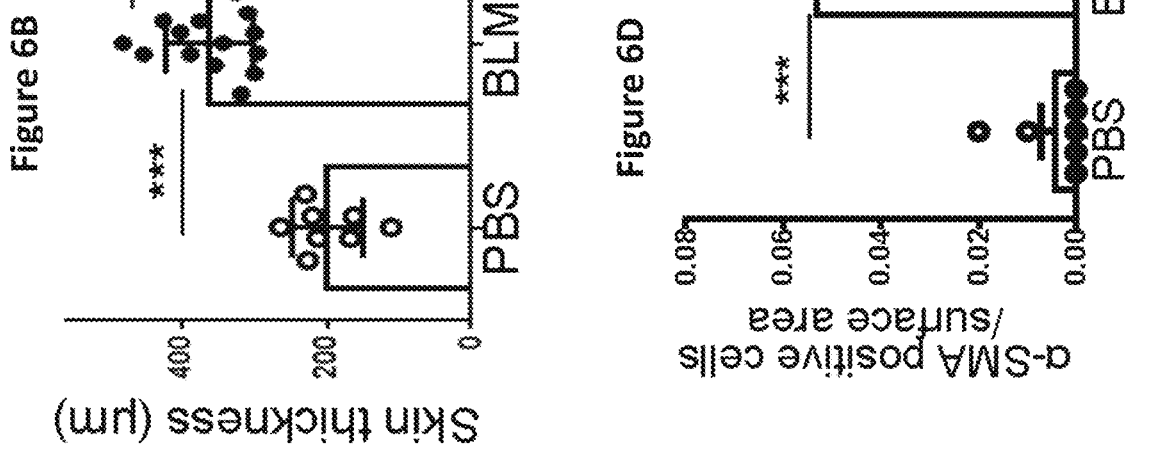
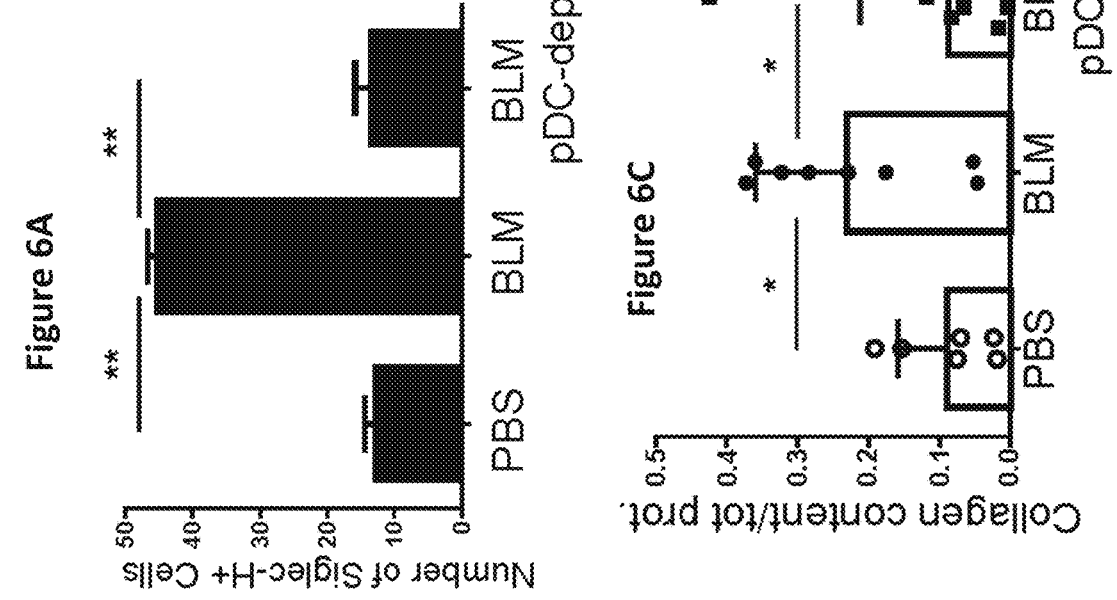
Figure 6A, Figure 6B, Figure 6C, Figure 6D

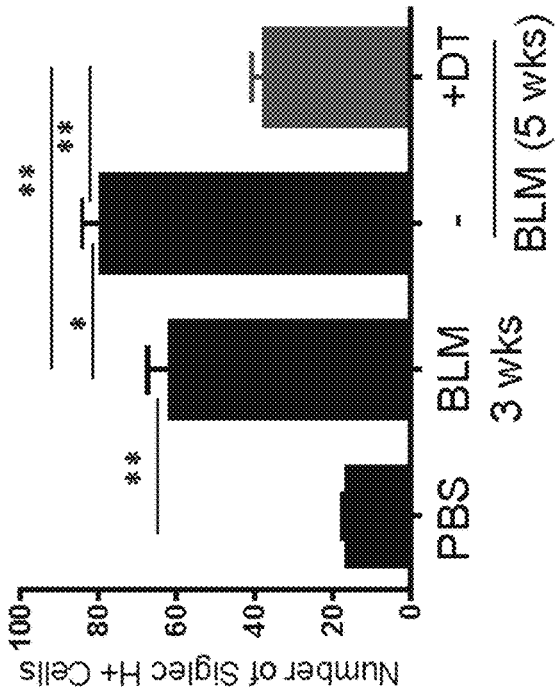
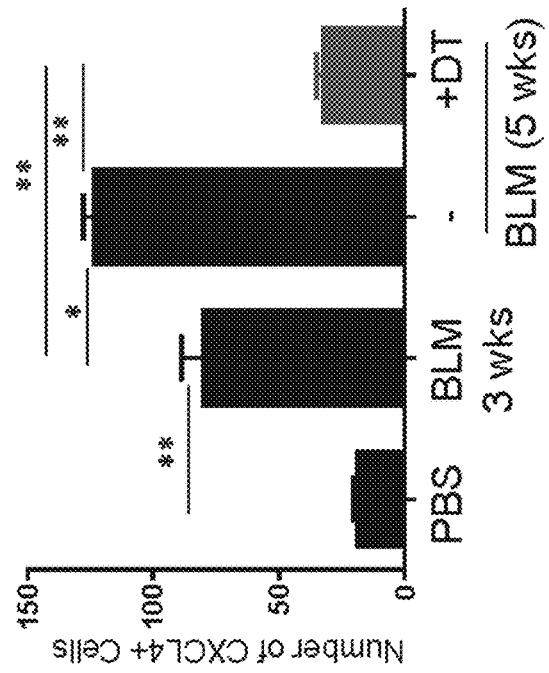
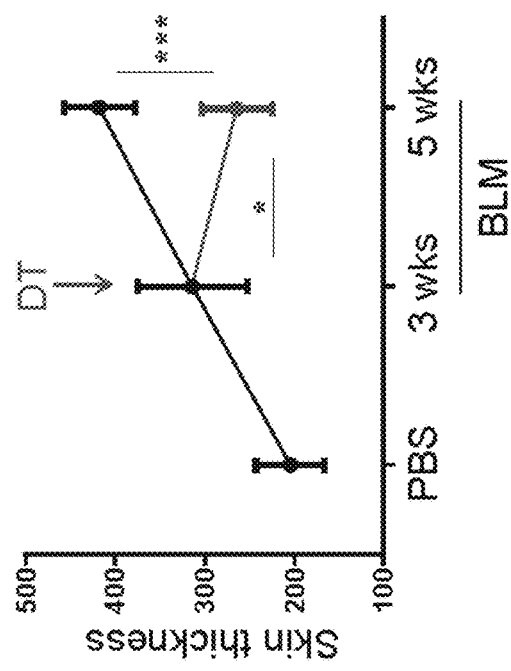
Figure 7A
Figure 7B
Figure 7C

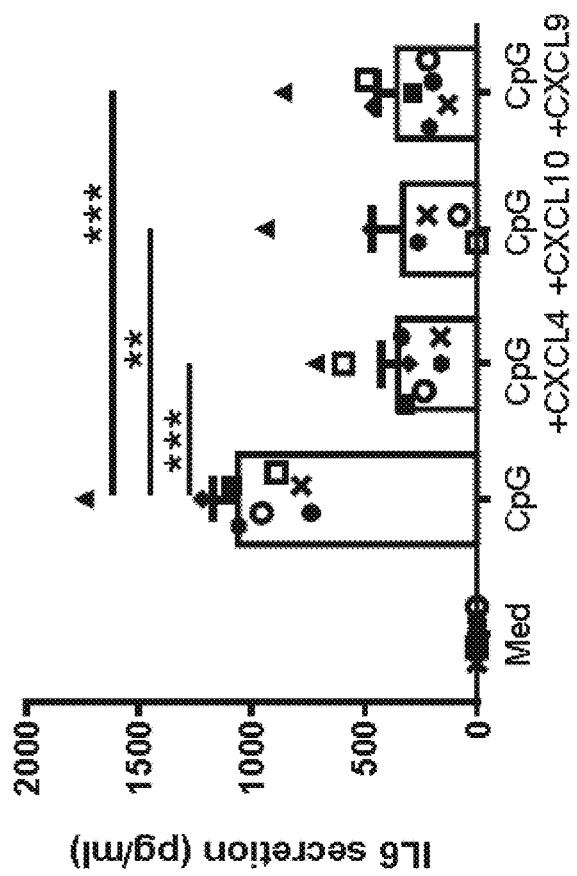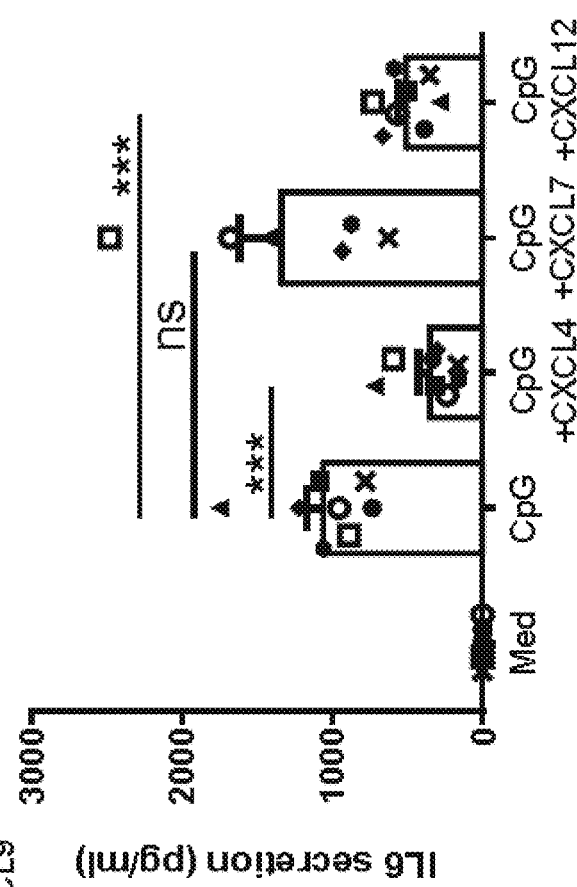

METHODS OF TREATING CANCER, INFECTIOUS DISEASE, AND AUTOIMMUNE DISEASE USING CXC CHEMOKINES

CROSS REFERENCE TO RELATED APPLICATION

The present application claims priority to U.S. Patent Application Ser. No. 62/433,038 filed Dec. 12, 2016, and U.S. Patent Application Ser. No. 62/492,562 filed May 1, 2017, both of which are hereby incorporated by reference in their entirety.

BACKGROUND OF THE INVENTION

The innate immune system recognizes a broad range of molecular structures that are conserved products present in various microorganisms, and are often referred to as pathogen-associated molecular patterns. This recognition depends on a diverse set of germline-encoded receptors, termed pattern recognition receptors (PRRs). These PRRs include a variety of molecules, such as mannose receptors, glucan receptors, scavenger receptors, and Toll-like receptors (TLRs), as well as intracellular sensors, such as the retinoic acid inducible (RIG)-I-like receptors (RLRs), and DNA sensors such as AIM2 or cGAS. Recognition of microbial molecules can trigger a rapid response by these PRRs, leading to a burst of proinflammatory cytokines and type-I interferons (IFNs), as well as stimulation of professional antigen-presenting cells that initiate and instruct the subsequent adaptive immune response. Nucleic acids have an especially important role as ligands for PRRs because the immune system is primed to respond to infection by microbial DNA and RNA. Sensors of nucleic acids are present in the endosomes of cells and also in their cytosol, and the cellular distribution and redundancy of these sensors allow the maximum protection against pathogens.

Nucleic acid recognition by these innate receptors leads to a potent activation of the innate immune system and the subsequent production of proinflammatory mediators, such as the type-I IFNs but also TNF, IL-1s, IL-6 and a set of pro-inflammatory cytokines and chemokines. During the past fifteen years, following the identification of TLR9 as a receptor for bacterial DNA, there has been remarkable progress in our understanding of how cells of the immune system have evolved to recognize pathogens via their genomes or the nucleic acids that are produced during their replication. The importance of nucleic acid recognition is illustrated by a broad redundancy among the many different types of receptors that are expressed by different cells and signals using distinct or, in some cases, redundant signaling pathways. Although pathogens are constantly evolving, nucleic acids are an intrinsic part of their structures, so it is not surprising that the immune system has built a series of tools to sense nucleic acids, and these are an important part of its arsenal for responding to pathogens.

Nucleic acids from viral genomes or products of viral replication are very potent drivers of immune defenses. However, the recognition of nucleic acids by innate immune cells blurs the boundaries of self- and nonself-discrimination because nucleic acids are common to both viruses and the host cells of which they infect. Thus, this fine balance can be easily perturbed resulting in potent immune activation by self-nucleic acids that accrue in endosomal or cytosolic compartments, leading to a myriad of localized and systemic inflammatory diseases.

Being critical players in controlling immune responses, the ability to regulate and control the signaling of PRRs is of great value, and thus, PRRs have become targets in a number of clinical indications including cancer, infectious diseases, allergic situations, asthma, as well as autoimmune diseases. Drugs that targets these PRRs are either used as single agent or in combination with other drugs.

Chemokines are small, about 8-10 kilodaltons in mass, secreted proteins that can mediate immune cell trafficking and lymphoid tissue development, and are found in all vertebrates. These proteins can also have pro-inflammatory properties, in particular during an immune response by helping to recruit cells to tissues. Chemokines are characterized by the presence of four cysteine residues in conserved locations that are key to forming their three-dimensional shape. Chemokines can be subdivided into four main classes depending on the location of the first two cysteine (C) residues in their protein sequence: namely, the CC chemokines, the CXC-chemokines, C chemokines and CX3C-chemokines. All of these proteins exert their biological effects by interacting with G protein-linked transmembrane receptors called chemokine receptors, which are selectively found on the surfaces of their target cells.

CXCL4 is a member of CXC chemokines released in high concentrations from activated platelets but can also be produced by hematopoietic cells. Although not well defined, the function of CXCL4 seems to be associated with coagulation but its role in regulating inflammation is unclear. Additionally, the nature of its receptor is unclear and at least two CXCL4 receptors have already been identified, CXCR3B present on activated T cells and on human microvascular endothelial cells, and chondroitin sulfate proteoglycan present on neutrophils. Both receptors were shown to have high affinity to CXCL4.

Chemokine receptors belong to the G protein-coupled receptor (GPCR) superfamily. CXCR3 is a seven transmembrane α-helix G protein-coupled receptor which was first identified in the late 1990s. Biochemical studies have identified three CXCR3 splice variants containing slightly different amino acid sequences: CXCR3A, CXCR3B and CXCR3-alt. As opposed to the two other variants, CXCR3alt possesses only the first five transmembrane domains and its function is unclear. CXCR3 is predominantly expressed on NK cells, T cells, B cells and DCs but also on non-immune cells. While CXCL9 only binds CXCR3A and CXCL4 only binds CXCR3B, CXCL10 can bind both CXCR3A and B splice variants and it is possible that other chemokines may engage this receptor as well.

It has been described that plasmacytoid dendritic cells (pDCs) are the main type I interferon (IFN) producers in human blood and they play a key role in innate anti-viral immunity. In addition, pDCs have been associated with autoimmunity in various contexts with a clear link with lupus (Barrat et al. 2005). pDCs and type I IFN also play a role in a number of cutaneous autoimmune diseases such as dermatomyositis, lichen sclerosis, cutaneous GVHD and cutaneous lupus (Wenzel and Tuting 2008). Although it is well described that pDCs infiltrate the skin following injury or in diseases, little is known about what is controlling pDCs trafficking and subsequent activation in the skin or whether pDCs can play a role in promoting/sustaining inflammation-related fibrosis.

In addition, pDCs respond quickly to inflammation and tissue injury, and can infiltrate tumors. However, their presence is often described as a negative prognosis factor in some cancers because they have reduced response to their known stimuli such as nucleic acids and may be prone to induce the generation of tumor specific regulatory T cells. However, activating pDCs in tumors has become a strategy to induce cytotoxic T cells as there is a clear benefit to try to re-activate these cells in the tumors, so they can produce type I and III IFNs which is key to activate tumor-specific cytotoxic T cells.

B cells are key cells of the adaptive immune system and can produce antibodies which are key mediators of the immune response to pathogens but can also mediate end-organ damage due to complement activation in multiple autoimmune diseases. Innate receptors are key to influence B cell responses, and mediators, such as IFNs, also impact their function. The ability to control B cell response would thus be of critical value in autoimmune diseases or in infectious situations. In addition, B cell leukemia are very difficult diseases to treat and controlling B cell proliferation/activation is thus of critical value in treatment of that disease.

Monocytes and macrophages contribute to the inflammatory status in multiple inflammatory and autoimmune situations through the production of cytokines such as TNF, IL-6 or IL-1s but also IFNs, and the control of their activation is an important area of research because of its potential impact in human disease.

SUMMARY OF THE INVENTION

The current invention is based upon several discoveries regarding toll-like receptors (TLR) 8 and 9 and the CXC chemokines, CXCL4, CXCL9, CXCL10, and CXCL12 that have implications in the treatment and prevention of disease. Based upon these findings, various CXC chemokines, including but not limited to CXCL1, CXCL2, CLXC3, CXCL4, CXCL5, CLXC9, CXCL10, CXCL11, CXCL12, CXCL13, CXCL14, CXCL15, CXCL16, and CXCL17, potentially can be used in treatment and prevention of disease. Additionally, the receptors that are targeted by these chemokines, including but not limited to CXCR1, CXCR2, CXCR3, CXCR4, CXCR5, CXCR6, and CXCR7 can also be used in the treatment and prevention of disease.

As shown herein:
1. In healthy plasmacytoid dendritic cells (pDCs) as well as in pDCs from patients with autoimmune diseases, such as systemic lupus erythematosus and systemic sclerosis, CXCL4, CXCL10, and CXCL12 potentiate the activation and/or response of TLR9. One effect of this response is the increased production of interferon-α (IFN-α). Additionally, CXCL4 and IFN-α production by pDCs are regulated by P13Kδ.
2. In pDCs from subjects with systemic sclerosis, CXCL4 potentiates the activation and/or response of TLR8, which is aberrantly expressed in these patients and contributes to the disease.
3. In healthy B cells, CXCL4, CXCL10, and CXCL12 as well as CXCL9 inhibit the activation and/or response of TLR9. One effect of this response is the decreased production of IL-6, TNF and expression of activation markers.
4. In healthy macrophages, CXCL4 potentiates the activation and/or response of TLR8. One effect of this response is the increased production of IL-6 and TNF.

These findings have several implications on the treatment and prevention of diseases including cancer, autoimmune diseases and infectious diseases caused by viruses and bacteria.

With regard to cancer and infectious disease, the increase in the production of IFN-α is beneficial, and as shown herein, activating and/or increasing a chemokine including but not limited to CXCL4, CXCL10, and/or CXCL12 with an agonist of TLR9 can have synergistic effects on the production of IFN-α by pDCs. Thus, one embodiment of the current invention is a method of treating cancer in a subject in need thereof by administering a therapeutically effective amount of an agent that activates and/or increases a chemokine including but not limited to CXCL4, CXCL10, and/or CXCL12, wherein the administration of the agent increases and/or potentiates the activation of TLR9 in pDCs to produce an increased amount or level of IFN-α.

A further embodiment of the present invention is a method of treating cancer in a subject in need thereof by administering a therapeutically effective amount of an agent that agonizes TLR9 and an agent that activates and/or increases a chemokine including but not limited to CXCL4, CXCL10, and/or CXCL12, wherein the administration of both agents activates pDCs to produce an increased amount or level of IFN-α.

In further embodiments, the agents can be administered with other therapeutic agents for cancer, including but not limited to checkpoint inhibitors.

In these embodiments, the agents can be administered to the subject together or separately. In further embodiments, the agents can be injected directly into the tumor tissue of the subject. In further embodiments, the pDC cells can be treated, contacted or incubated with one of more agents per the methods of the invention ex vivo, and transplanted into the subject. In some embodiments, the pDC cells are transplanted directly into the tumor tissue of the subject.

A further embodiment of the current invention is a method of treating an infectious disease in a subject in need thereof by administering a therapeutically effective amount of an agent that activates and/or increases a chemokine including but not limited to CXCL4, CXCL10, and/or CXCL12, wherein the administration of the agent increases and/or potentiates the activation of TLR9 in pDCs to produce an increased amount or level of IFN-α.

A further embodiment of the present invention is a method of treating infectious disease in a subject in need thereof by administering a therapeutically effective amount of an agent that agonizes TLR9 and an agent that activates and/or increases a chemokine including but not limited to CXCL4, CXCL10, and/or CXCL12, wherein the administration of both agents activates pDCs to produce an increased amount or level of IFN-α.

In further embodiments, the agents can be administered with other therapeutic agents for infectious disease, including but not limited antiviral agents and antibiotics.

In these embodiments, the agents can be administered together or separately. In further embodiments, the pDC cells can be treated, contacted or incubated with one of more agents per the methods of the invention ex vivo, and transplanted into the subject.

In autoimmune diseases such as SLE, the production of IFN-α is detrimental. Thus, a further embodiment of the current invention is a method of treating and/or preventing an autoimmune disease in a subject in need thereof by administering a therapeutically effective amount of an agent that antagonizes, inhibits and/or reduces a chemokine including but not limited to CXCL4, CXCL10, and/or CXCL12 to the subject, wherein the administration of the agent decreases or inhibits the activation of TLR9 in pDCs to produce a lesser amount or level of IFN-α.

In these embodiments, the agents can be administered to the subject or the pDC cells can be treated, contacted or incubated with one of more agents per the methods of the invention ex vivo, and transplanted into the subject.

Yet a further embodiment of the current invention is a method of treating and/or preventing systemic sclerosis in a subject in need thereof by administering a therapeutically effective amount of an agent that antagonizes, inhibits and/or reduces CXCL4 to the subject, wherein the administration of the agents decreases or inhibits the activation of TLR8 in pDCs to produce a lesser amount or level of CXCL4 and/or IFN-α.

In these embodiments, the agents can be administered to the subject, preferably to the skin tissue directly or the pDC cells can be treated, contacted or incubated with one of more agents per the methods of the invention ex vivo, and transplanted into the subject, preferably to the skin tissue.

The current invention is also based upon the surprising discovery that CXCL4, CXCL9, CXCL10, and CXCL12 blocks or mitigates the response of toll-like receptor (TLR) 9 in B cells. This has implications in autoimmune disease and leukemia where the mitigation of B cell response is crucial. Thus, one embodiment of the current invention is a method of controlling or mitigating a B cell response in a subject in need thereof by administering a therapeutically effective amount of an agent that antagonizes, inhibits and/or reduces a chemokine including but not limited to CXCL4, CXCL9, CXCL10, and/or CXCL12 in B cells.

A further embodiment of the invention is a method of treating and/or preventing an autoimmune disease in a subject in need thereof by administering a therapeutically effective amount of an agent that antagonizes, inhibits and/or reduces a chemokine including but not limited to CXCL4, CXCL9, CXCL10, and/or CXCL12 in B cells, wherein the administration of the agent increases and/or potentiates the activation of TLR9 in B cells.

Yet a further embodiment of the current invention is a method of treating leukemia in a subject in need thereof by administering a therapeutically effective amount of an agent that activates and/or increases a chemokine including but not limited to CXCL4, CXCL9, CXCL10, and/or CXCL12 in B cells, wherein the administration of the agent decreases or inhibits the activation of TLR9 in B cells.

In these embodiments, the agents can be administered to the subject or the B cells can be treated, contacted or incubated with one of more agents per the methods of the invention ex vivo, and transplanted into the subject.

Lastly the current invention is based on the surprising discovery that CXCL4 and TLR8 synergize to induce IL-6 and TNF-α in human macrophages. This finding has implications in the treatment and prevention of autoimmune diseases, where the increase in the production of TNF-α is detrimental to the disease. Thus, a further embodiment of the present invention is a method of treating and/or preventing an autoimmune disease in a subject in need thereof by administering a therapeutically effective amount of an agent that antagonizes, inhibit and/or reduces a chemokine including but not limited to CXCL4 and/or CXLC10 to the subject, wherein the administration of the agent decreases or inhibits the activation of TLR8 to produce TNF-α in macrophages.

In these embodiments, the agents can be administered to the subject or the macrophages can be treated, contacted or incubated with one or more agents per the method of the invention ex vivo, and transplanted into the subject.

The current invention also includes kits and pharmaceutical compositions comprising any of the agents alone or combined for use in the methods of the invention and comprising any of the cells treated, contacted or incubated as set forth by the methods of the invention for the treatment and/or prevention of diseases.

BRIEF DESCRIPTION OF THE FIGURES

For the purpose of illustrating the invention, there are depicted in drawings certain embodiments of the invention. However, the invention is not limited to the precise arrangements and instrumentalities of the embodiments depicted in the drawings.

Abbreviations that are used throughout the figures include: HD—healthy donor; SSc—systemic sclerosis; pDC—plasmacytoid dendritic cells; PMBC—peripheral mononuclear blood cells; WT—wild type; BLM—bleomycin.

FIG. 1 shows that pDCs infiltrate the skin of SSc patients and spontaneously secrete IFN-α and CXCL4.

FIG. 2 shows that TLR8 is aberrantly expressed on pDCs from SSc patients. FIG. 2B data are relative to medium condition. Statistical significance was evaluated with FIG. 2A a parameter paired t test and FIG. 2C using a Mann-Whitney U-test *p<0.05; p<0.01; *p<0.001. FIG. 2D shows TLR8 expression levels quantified in purified pDCs (n=18 HDs; n=29 SSc patients and n=6 SLE patients), B cells (n=14 for HDs; n=8 SSc patients) or monocytes (n=17 HDs; n=11 SSc patients) from PBMCs indicated. FIG. 2E shows gene expression level of TLR7, TLR9 and TLR10 quantified by qPCR in purified pDCs (n=17-18 HDs; n=29-31 SSc patients, n=6 SLE patients). FIG. 2F shows gene expression levels of TLR7, TLR9 and TLR10 quantified by qPCR in purified B cells (n=12-14 HDs; n=6-8 SSc patients). FIG. 2G shows gene expression levels of TLR7, TLR9 and TLR10 quantified by qPCR in purified monocytes (n=16-18 HDs; n=11 SSc patients). All results (FIGS. 2D-2G) are represented as a mean±SEM. Statistical significance was evaluated using a Mann-Whitney U-test and *p<0.05; p<0.01; *p<0.001 and only comparisons that are significant are shown.

FIG. 3 shows that TLR8 signaling induces CXCL4 and IFN-α secretion by SSc PDCs.

FIG. 4 shows that CXCL4 potentiates TLR8-mediated activation of SSc pDCs. FIG. 4C shows CXCL4 as quantified by ELISA from purified pDCs from HDs cultured alone and purified pDCs from SSc patients cultured for 24 hours either alone or in the presence of the PI3Kδ inhibitor CAL-101. Results are normalized to 10,000 cells. FIG. 4D shows IFN-α as quantified by ELISA from purified pDCs from SSc patients cultured for 24 hours either alone or in the presence of the PI3Kδ inhibitor CAL-101. Results are normalized to 10,000 cells. FIG. 4E shows IL-6 levels as quantified by ELISA from purified pDCs from SSc patients cultured for 24 hours either alone or in the presence of the PI3Kδ inhibitor CAL-101. Results are normalized to 10,000 cells. All results are represented as a mean±SEM and statistical significance was evaluated using a Mann-Whitney U-test and *p<0.05; p<0.01; *p<0.001.

FIG. 5 shows that CXCL4 potentiates TLR9-mediated activation but has minimal effect on TLR7-mediated activation of pDCs purified from SSc or HDs. FIG. 5A shows IFN-α quantified in the supernatants by ELISA in purified pDCs from HDs cultured in media alone (control), or with either a CpG-C, a TLR9 agonist or with CpG-C and CXCL4. FIG. 5B shows IFN-α quantified in the supernatants by ELISA in purified pDCs from HDs cultured in media alone (control), or with either a CpG-B, a TLR9 agonist or with CpG-B and CXCL4. FIG. 5C shows IFN-α quantified in the supernatants by ELISA in purified pDCs from HDs cultured in media alone (control), or with a TLR7 agonist (heat-inactivated VR95 influenza virus at 0.5 MOI, FLU) or with FLU and CXCL4 for 24 hours.

FIG. 6 shows that pDCs infiltrate the skin of BLM-treated mice and their depletion attenuates skin fibrosis. FIG. 6A is a graph of the average number of Siglec-H$^+$ cells (value based on 5 skin sections with n=8-12 mice per/group) in WT mice injected with PBS (left bar) and with BLM (middle bar), and of CLEC4C-DTR mice injected with DT and BLM (right bar). FIG. 6B are graphs quantifying the skin thickness of WT mice receiving PBS (left bar), WT mice injected with DT, and treated with BLM (middle bar), and CLEC4C-DTR mice injected with DT and BLM (right bar) from Trichrome Masson-stained skin sections at a 10× magnification. FIG. 6C is a graph of the collagen content in the skin expressed as a ratio of collagen per total protein in the same mice. FIG. 6D is a graph quantifying the number of α-SMA-positive cells per surface area in dermis from images of α-smooth muscle actin (SMA) immunohistochemistry of the dermis at a 40× magnification in the same mice.

FIG. 7 shows that pDCs are critical for the maintenance of skin fibrosis and for the presence of CXCL4 in the skin. Fibrosis was induced by injection of BLM in WT mice for either 3 weeks or 5 weeks or in CLEC4C-DTR mice for 5 weeks as described in material and methods. At 3 weeks of BLM treatment, pDC depletion was achieved in CLEC4C-DTR mice by DT injection (in red) while fibrosis induction was sustained for 2 more weeks. FIG. 7A shows the average of skin thickness in the indicated mice. FIG. 7B shows the number of Siglec-H$^+$ cells in the skin in the indicated mice. FIG. 7C shows the average of the number of CXCL4$^+$ cells in the indicated mice. Experiment was done twice with (n=6-10 per group). All results are represented as a mean±SEM and statistical significance was evaluated using a Mann-Whitney U-test and *p<0.05; p<0.01; *p<0.001.

FIG. 8 shows that TLR8 exacerbates disease in the bleomycin-induced fibrosis model.

FIG. 9 shows the impact of CXCL7, CXCL9, CXCL10 and CXCL12 on TLR9-mediated activation of pDCs.

FIG. 10 shows the impact of AMG487 on CXCL4 and CXCL10 activity upon TLR9-mediated activation of pDCs.

FIG. 12 shows that CXCL4 negatively regulates TLR9 (CpG-C)-mediated activation of human B cells.

FIG. 13 shows that CXCL4 has little effect on TLR7-mediated activation of human B cells.

FIG. 14 shows the impact of CXCL4, CXCL7, CXCL9, CXCL10 and CXCL12 on TLR9-mediated activation of human B cells. FIG. 14A is a graph of IL-6 as quantified in the supernatants by ELISA of purified B cells from HDs cultured in media alone (control), with either a CpG TLR9 agonist or with CpG and either CXCL4, CXCL10 or CXCL9. FIG. 14B is a graph of IL-6 as quantified in the supernatants by ELISA of purified B cells from HDs cultured in media alone (control), with either a CpG TLR9 agonist or with CpG and either CXCL4, CXCL7 or CXCL12. Results are represented as a mean±SEM and individual donors are shown and statistical significance evaluated using a Mann-Whitney U-test and *p<0.05; p<0.01; *p<0.001.

FIG. 15 shows the impact of AMG487 on CXCL4 activity upon TLR9-mediated activation of B cells.

FIG. 16 shows the impact of AMG487 on CXCL10 activity upon TLR9-mediated activation of B cells.

FIG. 17 is a graph of IP-10, IL-6 and TNF gene expression at 6 hours post culture of human macrophages prepared from purified monocytes by culturing the cells overnight with G-CSF. Cells were then cultured for 6 hours either with medium only, with ORN8L, with CXCL4 alone or with a combination of the CpG-ODN with increasing concentration of CXCL4 (1, 3 or 10 µg/ml) gene measured by q-PCR relative to GAPDH.

DETAILED DESCRIPTION OF THE INVENTION

Definitions

Figure 1A:
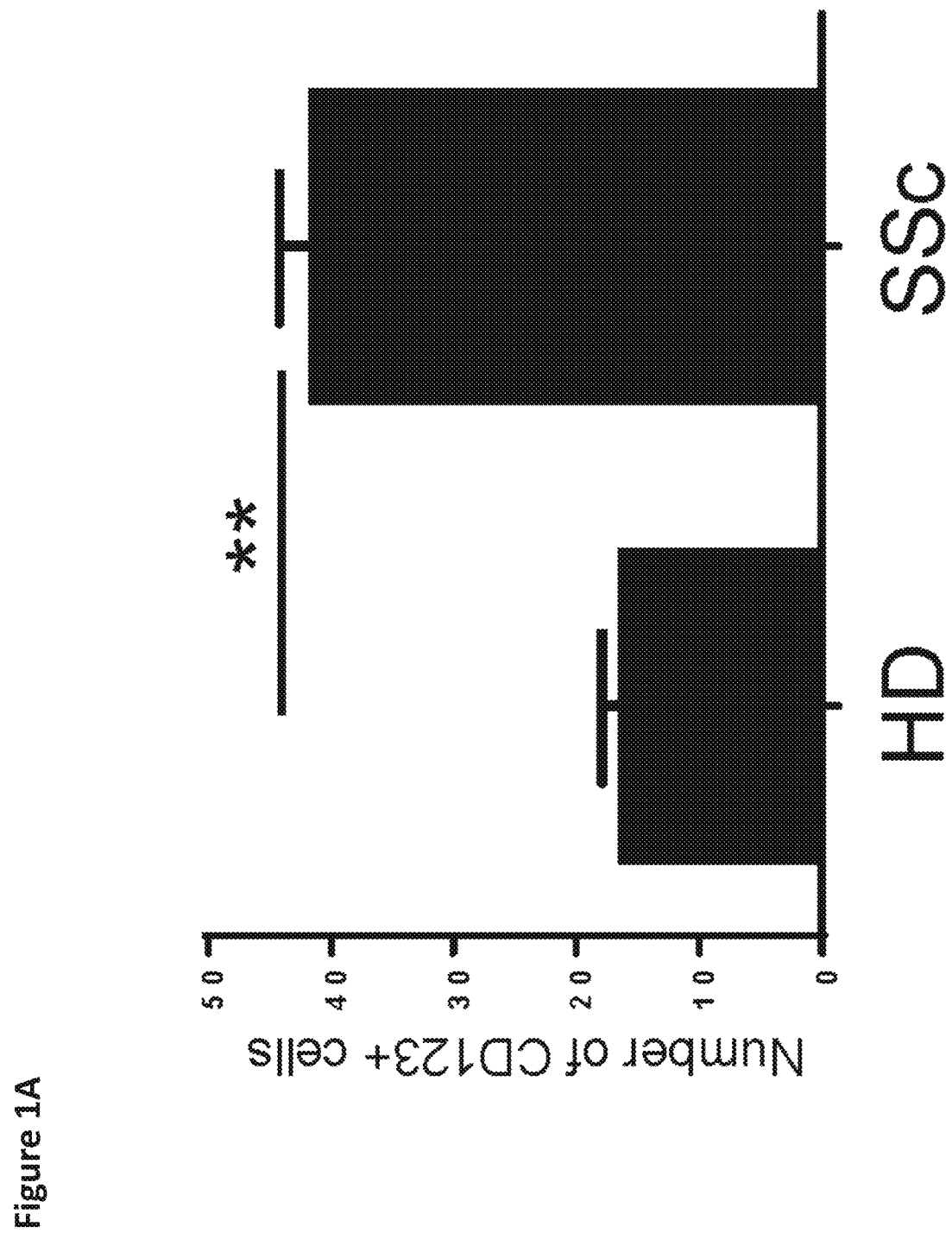
FIG. 1A is a graph of the quantification of the number of CD123+ counted in 5 high-power microscopic fields (based on 5 bioptic samples of patients with SSc and of 5 controls).

The terms used in this specification generally have their ordinary meanings in the art, within the context of this invention and the specific context where each term is used. Certain terms are discussed below, or elsewhere in the specification, to provide additional guidance to the practitioner in describing the methods of the invention and how to use them. Moreover, it will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of the other synonyms. The use of examples anywhere in the specification, including examples of any terms discussed herein, is illustrative only, and in no way limits the scope and meaning of the invention or any exemplified term. Likewise, the invention is not limited to its preferred embodiments.

The term "subject" as used in this application means an animal with an immune system such as avians and mammals. Thus, the invention can be used in veterinary medicine, e.g., to treat companion animals, farm animals, laboratory animals in zoological parks, and animals in the wild. The invention is particularly desirable for human medical applications.

The term "patient" as used in this application means a human subject. In some embodiments of the present invention, the "patient" is one suffering with cancer, an infectious disease or an autoimmune disease or suspected of suffering from cancer, an infectious disease or an autoimmune disease.

The terms "treat", "treatment", and the like refer to a means to slow down, relieve, ameliorate or alleviate at least one of the symptoms of the disease, or reverse the disease after its onset.

The terms "prevent", "prevention", and the like refer to acting prior to overt disease onset, to prevent the disease from developing or minimize the extent of the disease or slow its course of development.

The term "agent" as used herein means a substance that produces or is capable of producing an effect and would include, but is not limited to, chemicals, pharmaceuticals, biologics, small organic molecules, antibodies, nucleic acids, peptides, and proteins.

The phrase "therapeutically effective amount" is used herein to mean an amount sufficient to cause an improvement in a clinically significant condition in the subject, or delays or minimizes or mitigates one or more symptoms associated with the disease, or results in a desired beneficial change of physiology in the subject.

The phrase "in need thereof" indicates a subject has cancer, an infectious disease or an autoimmune disease, is suspected of having cancer, an infectious disease or an autoimmune disease, or has risk factors for cancer, an infectious disease or an autoimmune disease.

The term "autologous" refers to any material derived from the same individual to whom it is later to be re-introduced into the same individual.

The term "allogeneic" refers to any material derived from a different animal of the same species as the individual to whom the material is introduced. Two or more individuals are said to be allogeneic to one another when the genes at one or more loci are not identical.

The terms "vector", "cloning vector" and "expression vector" mean the vehicle by which a DNA or RNA sequence (e.g., a foreign gene) can be introduced into a host cell, so as to transform the host and promote expression (e.g., transcription and translation) of the introduced sequence. Vectors include, but are not limited to, plasmids, phages, and viruses.

The term "host cell" means any cell of any organism that is selected, modified, transformed, grown, used or manipulated in any way, for the production of a substance by the cell, for example, the expression by the cell of a gene, a DNA or RNA sequence, a protein or an enzyme. Host cells can further be used for screening or other assays, as described herein.

A "polynucleotide" or "nucleotide sequence" is a series of nucleotide bases (also called "nucleotides") in a nucleic acid, such as DNA and RNA, and means any chain of two or more nucleotides. A nucleotide sequence typically carries genetic information, including the information used by cellular machinery to make proteins and enzymes. These terms include double or single stranded genomic and cDNA, RNA, any synthetic and genetically manipulated polynucleotide, and both sense and anti-sense polynucleotide. This includes single- and double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases, for example thio-uracil, thio-guanine and fluoro-uracil.

"Nucleic acid" refers to deoxyribonucleotides or ribonucleotides and polymers thereof in either single- or double-stranded form. The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. The nucleic acids may also be modified by many means known in the art. Non-limiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, and carbamates) and with charged linkages (e.g., phosphorothioates, and phosphorodithioates). Polynucleotides may contain one or more additional covalently linked moieties, such as, for example, proteins (e.g., nucleases, toxins, antibodies, signal peptides, and poly-L-lysine), intercalators (e.g., acridine, and psoralen), chelators (e.g., metals, radioactive metals, iron, and oxidative metals), and alkylators. The polynucleotides may be derivatized by formation of a methyl or ethyl phosphotriester or an alkyl phosphoramidate linkage. Modifications of the ribose-phosphate backbone may be done to facilitate the addition of labels, or to increase the stability and half-life of such molecules in physiological environments. Nucleic acid analogs can find use in the methods of the invention as well as mixtures of naturally occurring nucleic acids and analogs. Furthermore, the polynucleotides herein may also be modified with a label capable of providing a detectable signal, either directly or indirectly. Exemplary labels include radioisotopes, fluorescent molecules, and biotin.

The term "polypeptide" as used herein means a compound of two or more amino acids linked by a peptide bond. "Polypeptide" is used herein interchangeably with the term "protein."

The term "about" or "approximately" means within an acceptable error range for the particular value as determined by one of ordinary skill in the art, which will depend in part on how the value is measured or determined, i.e., the limitations of the measurement system, i.e., the degree of precision required for a particular purpose, such as a pharmaceutical formulation. For example, "about" can mean within 1 or more than 1 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as Molecular Cloning: A Laboratory Manual, second edition (Sambrook, et al., 1989) Cold Spring Harbor Press; Oligonucleotide Synthesis (M. J. Gait, ed. 1984); Methods in Molecular Biology, Humana Press; Cell Biology: A Laboratory Notebook (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); DNA Cloning: A practical Approach, Volumes I and II (D. N. Glover ed. 1985); Nucleic Acid Hybridization (B. D. Hames & S. J. Higgins eds. (1985»; Transcription and Translation (B. D. Hames & S. J. Higgins, eds. (1984»; Animal Cell Culture (R. I. Freshney, ed. (1986»; Immobilized Cells and Enzymes (1RL Press, (1986»; and B. Perbal, A practical Guide To Molecular Cloning (1984); F. M. Ausubel et al. (eds.).

CXCL4, CXCL10, and CXCL12 Potentiate the Response of TLR8 and TLR9 in Plasmacytoid Dendritic Cells (pDCs)

CXCL4 also known as PF4 is small chemokine belonging to the CXC chemokine family. CXCL4 is a 70-amino acid protein that is released from the alpha-granules of activated platelets and binds with high affinity to heparin. Its major physiologic role appears to be neutralization of heparin-like molecules on the endothelial surface of blood vessels, thereby inhibiting local antithrombin III activity and promoting coagulation. Sequences for CXCL4 are publicly available (see, for example, GenBank Gene ID 5196).

CXCL10 also known as IP-10 is another small chemokine belonging to the CXC chemokine family and a ligand for the receptor CXCR3. Binding of this protein to CXCR3 results in pleiotropic effects, including stimulation of monocytes, natural killer and T-cell migration, modulation of adhesion molecule expression, and inhibition of vessel formation. Sequences for CXCL10 are publicly available (see, for example, GenBank Gene ID 3627).

CXCL12 also known as stromal cell-derived factor-1 (SDF1) is another small chemokine belonging to the CXC chemokine family. Sequences for CXCL12 are publicly available (see, for example, GenBank Gene ID 6386).

As shown herein, it has been discovered that these three chemokines activate the response of toll-like receptors (TLR) 9 in healthy plasmacytoid dendritic cells (pDCs) as well as pDCs from patients with autoimmune disease. The activation of this response includes the expression and secretion of interferon-α (IFN-α). As discussed above, activating pDCs in tumors has become a strategy to induce cytotoxic T cells as there is a clear benefit to try to re-activate these cells in the tumors. The key objective is thus to re-ignite these cells so they can produce type I and III IFNs which is key to activating tumor-specific cytotoxic T cells. CpG-ODNs (CpG oligonucleotides) are agonists of the TLR9 and have the ability to induce type I and type III IFN by blood cells and in particular by plasmacytoid dendritic cells (pDCs). CpG-ODNs are being investigated in various cancer indications since the interferon produced is key to promote the induction and activation of CD8+ T cells that eventually kill the tumor cells. However, one of the main issues with the use of these agonists is that although pDCs infiltrate the tumors and can indeed respond to CpG-ODN, the magnitude of the response is moderate because of the impact of the tumor microenvironment.

Thus, one embodiment of the current invention is a method of treating cancer in a subject in need thereof by administering a therapeutically effective amount of an agent or agents that activates and/or increases the expression and/or activity of a chemokine in pDCs. In one embodiment, the chemokine is a CXC chemokine. In a further embodiment, the CXC chemokine is chosen from the group consisting of CXCL4, CXCL10, and CXCL12.

A further embodiment of the current invention is a method of treating cancer in a subject in need thereof by administering a therapeutically effective amount of an agent or agents that activates or increases the expression and/or activity of a chemokine, and a therapeutically effective amount of an agonist of TLR9 in pDCs. In one embodiment, the chemokine is a CXC chemokine. In a further embodiment, the CXC chemokine is chosen from the group consisting of CXCL4, CXCL10, and CXCL12. The agent(s) and agonist work synergistically to increase the beneficial response of the pDCs of producing and secreting interferon.

TLR9 agonists are known in the art and include CpG nucleotides (CpG-ODN) as well as various other compounds being developed for use in cancer treatment including but not limited to those listed in Table 1, including but not limited to MGN1703 and MGN1601. CpG-ODNs that can be used in the current invention include CpG-B and CpG-C as well as CpG-A. Other agonists of TLR9 can used in the methods of the invention including those known and those later discovered or developed.

A further embodiment of the current invention is a method of treating cancer in a subject in need thereof by administering a therapeutically effective amount of an agent or agents that activates and/or increases the expression and/or activity of a chemokine, and a therapeutically effective amount of an agonist of a pattern recognition receptor (PRR) in pDCs. In one embodiment, the chemokine is a CXC chemokine. In a further embodiment, the CXC chemokine is chosen from the group consisting of CXCL4, CXCL10, and CXCL12. The agent(s) and the agonist work synergistically to increase the beneficial response of the pDCs of producing and secreting interferon. PRRs that can be agonized or stimulated in the method of the invention include but are not limited to all toll-like receptors, retinoic acid inducible (RIG)-I-like receptors (RLRs), NOD-like receptors (NLRs), cGAS, and the STING pathway. Agonists of the PRRs include but are not limited to poly-ICLC (TLR3), imiquimod (TLR7), TMX-101 (TLR7), resiquimod (TLR7 and TLR8), motolimod (TLR8), and cyclic dinucleotides (STING).

The use of an agent or agents that activates and/or increases a chemokine in conjunction with a PRR agonist can also be combined with the administration of a checkpoint inhibitor. Checkpoint proteins interact with specific ligands which send a signal to the T cell and essentially turn off or inhibit T cell function. Cancer cells take advantage of this system by driving high levels of expression of checkpoint proteins on their surface which results in control of the T cells expressing checkpoint proteins on the surface of T cells that enter the tumor microenvironment, thus suppressing the anticancer immune response. As such, inhibition of checkpoint proteins results in complete or partial restoration of T cell function and an immune response to the cancer cells. Examples of checkpoint proteins include but are not limited to CTLA-4, PD-L1, PD-L2, PD-1, B7-H3, B7-H4, BTLA, HVEM, TIM3, GALS, LAGS, VISTA, KIR, 2B4 (belongs to the CD2 family of molecules and is expressed on all NK, γδ, and memory CD8+ (αβ) T cells), CD 160 (also referred to as BY55), CGEN-15049, CHK 1 and CHK2 kinases, A2aR and various B-7 family ligands. Currently marketed checkpoint inhibitors include Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody) and Yervoy/ipilimumab (anti-CTLA-4 checkpoint inhibitor).

Thus, a further embodiment of the current invention is a method of treating cancer in a subject in need thereof by administering a therapeutically effective amount of an agent or agents that activates and/or increases the expression and/or activity of a chemokine, and a therapeutically effective amount of an agonist of TLR9 in pDCs, in conjunction with a checkpoint protein or inhibitor. In one embodiment, the chemokine is a CXC chemokine. In a further embodiment, the CXC chemokine is chosen from the group consisting of CXCL4, CXCL10, and CXCL12.

A further embodiment of the current invention is a method of treating cancer in a subject in need thereof by administering a therapeutically effective amount of an agent that activates and/or increases the expression and/or activity of a chemokine, and a therapeutically effective amount of an agonist of a pattern recognition receptor (PRR) in pDCs, in conjunction with a checkpoint protein or inhibitor. In one embodiment, the chemokine is a CXC chemokine. In a further embodiment, the CXC chemokine is chosen from the group consisting of CXCL4, CXCL10, and CXCL12.

Cancers that can be treated by the methods of the current invention include but are not limited to lung cancer, colon cancer, melanoma, pancreatic cancer, mammary cancer, prostate cancer, breast cancer, ovarian cancer, basal cell carcinoma, biliary tract cancer, bladder cancer, bone cancer, cervical cancer, colon and rectum cancer, connective tissue cancer, cancer of the digestive system, endometrial cancer, esophageal cancer, cancer of the head and neck, kidney cancer, larynx cancer; liver cancer, fibroma, neuroblastoma, oral cavity cancer, skin cancer, testicular cancer, thyroid cancer, uterine cancer, medulloblastoma, sarcoma, squamous cell carcinoma, and lymphoma.

In particular, the methods of the invention can be used to treat solid tumors wherein the agents can be injected directly into the tumor tissue or the pDCs can be stimulated ex vivo and introduced into the tumor tissue.

Another area where the increased response of TLR9 in pDCs is beneficial is in infectious disease. A better IFN response leads to better clinical outcomes for patients with infectious diseases. Thus, a further embodiment of the present invention is a method of treating an infectious disease in a subject in need thereof by administering a therapeutically effective amount of an agent or agents that activates and/or increases the expression and/or activity of a chemokine in pDCs. In one embodiment, the chemokine is a CXC chemokine. In a further embodiment, the CXC chemokine is chosen from the group consisting of CXCL4, CXCL10, and CXCL12.

A further embodiment of the current invention is a method of treating an infectious disease in a subject in need thereof by administering a therapeutically effective amount of an agent that activates and/or increases the expression and/or activity of a chemokine, and a therapeutically effective amount of an agonist of TLR9 in pDCs. In one embodiment, the chemokine is a CXC chemokine. In a further embodiment, the CXC chemokine is chosen from the group consisting of CXCL4, CXCL10, and CXCL12. The agent(s) and the agonist will work synergistically to increase the beneficial response of the pDCs of producing and secreting interferon.

TLR9 agonists are known in the art and include CpG nucleotides (CpG-ODN) as well as various other compounds being developed for use in treatment of infectious disease including but not limited to those listed in Table 1 including but not limited to Heplisav-B. CpG-ODNs that can be used in the current invention include CpG-B and CpG-C. CpG-ODNs that can be used in the current invention include CpG-B and CpG-C as well as CpG-A. Other agonists of TLR9 can used in the methods of the invention including those known and those later discovered or developed.

A further embodiment of the current invention is a method of treating an infectious disease in a subject in need thereof by administering a therapeutically effective amount of an agent that activates and/or increases the expression and/or activity of a chemokine, and a therapeutically effective amount of an agonist of a pattern recognition receptor (PRR) in pDCs. In one embodiment, the chemokine is a CXC chemokine. In a further embodiment, the CXC chemokine is chosen from the group consisting of CXCL4, CXCL10, and CXCL12. The agent(s) and the agonist will work synergistically to increase the beneficial response of the pDCs of producing and secreting interferon. PRRs that can be agonized or stimulated in the method of the invention include but are not limited to all toll-like receptors, retinoic acid inducible (RIG)-I-like receptors (RLRs), NOD-like receptors (NLRs), cGAS, and the STING pathway. Agonists of the PRRs include but are not limited to poly-I; poly C12U (TLR3), imiquimod (TLR7), GS-9620 (TLR7), and SB 9200 (RIG-1 and NOD2).

The use of a an agent or agents that activates and/or increases a chemokine in conjunction with a PRR agonist can also be combined with the administration of an antiviral agent. Antiviral agents that can be used in the current methods include but are not limited to Acyclovir, Brivudin, Cidofovir, Famciclovir, Fomivirsen, Foscarnet, Ganciclovir, Penciclovir, Valacyclovir, Valganciclovir, Amantadine, Rimantadine, Oseltamivir, Zanamivir, Ribavirin, Adefovir, Emtricitabine, Entecavir, Lamivudine, Telbivudine, Boceprev, Telaprevir and Telaprevir.

The use of an agent or agents that activates and/or increases a chemokine in conjunction with a PRR agonist can also be combined with the administration of an antibiotic.

Yet a further embodiment of the current invention is a method of treating an infectious disease in a subject in need thereof by administering a therapeutically effective amount of an agent or agents that activates or increases the expression and/or activity of a chemokine, and a therapeutically effective amount of an agonist of TLR9 in pDCs, in conjunction with an antiviral agent or an antibiotic. In one embodiment, the chemokine is a CXC chemokine. In a further embodiment, the CXC chemokine is chosen from the group consisting of CXCL4, CXCL10, and CXCL12.

Yet a further embodiment of the current invention is a method of treating an infectious disease in a subject in need thereof by administering a therapeutically effective amount of an agent or agents that activates and/or increases the expression and/or activity of chemokine and a therapeutically effective amount of an agonist of a pattern recognition receptor (PRR) in pDCs, in conjunction with an antiviral agent or an antibiotic. In one embodiment, the chemokine is a CXC chemokine. In a further embodiment, the CXC chemokine is chosen from the group consisting of CXCL4, CXCL10, and CXCL12.

Infectious diseases that can be treated by the methods of the invention include but are not limited to chronic hepatitis B, chronic hepatitis, cytomegalovirus, Epstein-Barr virus, hepatitis C, human herpes simplex 1, human herpes simplex 2, human immunodeficiency virus, respiratory syncytial virus, varicella zoster virus, influenza virus, and human papilloma virus.

Bacterial infections that can treated by the methods of the invention include but are not limited to those caused by *Legionella pneumophilia*, *Streptococcus pyogenes*, and *Helicobacter pylori* as well as sepsis.

In these embodiments, the agents can be administered to the subject or the pDC cells can be treated, contacted or incubated with one of more agents per the methods of the invention ex vivo, and transplanted into the subject.

pDC is the key cell type mediating TLR-induced inflammation in autoimmune disease patients as well. In lupus, it has been shown that pDCs produce large amounts of type I IFN due to TLR7 and TLR9 recognition of endogenous RNA and DNA in the form of immune complexes (Barrat et al. 2005). It has also been shown that pDC activation prevents optimal response to corticosteroid treatment by lupus patients (Guiducci et al. 2010), and two recent studies identified pDCs as the key cell type promoting lupus in mouse models of the disease (Sisirak et al. 2014; Rowland et al. 2014). The importance of pDCs has also been observed in a series of related cutaneous autoimmune diseases such as dermatomyositis, lichen sclerosis, cutaneous Graft-versus-host disease (GVHD) or cutaneous lupus that share a common pathological inflammatory feature described as "interface dermatitis" (Wenzel and Tuting 2008). In these patients, pDCs massively infiltrate the skin and produce IFN-α which plays a major role in the development of cutaneous lesions.

Systemic Sclerosis (SSc) is a multisystem, fibrosing disorder in which vasculopathy, autoimmunity, and inflammation lead to diverse life-altering and life-threatening clinical manifestations (Varga and Abraham 2007). SSc has the highest degree of morbidity and mortality of the rheumatic diseases with a ten-year mortality rate of 23% to 45% (Mayes et al. 2003). The female predominance is about 4:1, and the usual age of onset is 35 to 55 years of age. The pathophysiology of SSc is not completely understood, but substantial evidence shows interplay between immunologic derangement, endothelial dysfunction, and pro-fibrotic mechanisms. A clear understanding of SSc pathogenesis has been impeded by the heterogeneous nature of the disease, which is seen clinically, serologically, and at the level of gene expression in the skin and peripheral blood (Lafyatis et al. 2009).

As shown herein, pDCs infiltrate the skin of SSc patients and are chronically activated, leading to increased secretion of IFN-α and CXCL4 which are both hallmarks of the disease. It is also shown herein that CXCL4 acts primarily by potentiating TLR8, but also TLR9-induced IFN production by pDCs. Depleting pDCs prevented disease in a mouse model of scleroderma and could revert fibrosis in mice with established disease. In contrast, the disease was exacerbated in mice transgenic for TLR8 with recruitment of pDCs to the fibrotic skin, whereas TLR7 only partially contributed to the inflammatory response, indicating that TLR8 is the key RNA-sensing TLR involved in the establishment of fibrosis. Thus, pDC is an essential cell type involved in the pathogenesis of SSc and its removal using depleting antibodies or attenuating pDC function could be a novel approach to treat SSc patients.

Thus, a further embodiment of the current invention is a method of treating and/or preventing an autoimmune disease in a subject in need thereof by administering a therapeutically effective amount of an agent or agents that antagonizes, inhibits and/or reduces the expression and/or activity of a chemokine in pDCs wherein the administration of the agents decreases or inhibits the activation TLR9 in pDCs to produce a lesser amount or level of IFN-α. In one embodiment, the chemokine is a CXC chemokine. In a further embodiment, the CXC chemokine is chosen from the group consisting of CXCL4, CXCL10, and CXCL12.

Autoimmune diseases that can be treated and/or prevented by the current methods of the invention include but are not limited to include but are not limited to systemic lupus erythematosus, rheumatoid arthritis, type 1 diabetes, multiple sclerosis, myasthenia gravis, Graves disease, pernicious anemia, scleroderma, psoriasis, inflammatory bowel diseases, Hashimoto's disease, Addison's disease, cutaneous autoimmune disease, systemic sclerosis and Sjögren's syndrome.

In these embodiments, the agents can be administered to the subject or the pDC cells can be treated, contacted or incubated with one of more agents per the methods of the invention ex vivo, and transplanted into the subject.

Yet a further embodiment of the current invention is a method of treating and/or preventing systemic sclerosis in a subject in need thereof by administering a therapeutically effective amount of an agent or agents that antagonizes, inhibits and/or reduces CXCL4 to the subject, wherein the administration of the agents decreases or inhibits the activation TLR8 in pDCs to produce a lesser amount or level of IFN-α.

In these embodiments, the agents can be administered to the subject, preferably to the skin tissue directly or the pDC cells can be treated, contacted or incubated with one of more agents per the methods of the invention ex vivo, and transplanted into the subject, preferably to the skin tissue.

In these embodiments of the invention, the phrase "in need thereof" indicates a subject has an autoimmune disease, is suspected of having an autoimmune, or has risk factors for an autoimmune disease.

TABLE 1

Clinical development of agonists and antagonists of nucleic acid sensors in human diseases

| Targeted receptor | Compound (name) | Company | Indications |
|---|---|---|---|
| TLR3 | Poly-ICLC (Hiltonol) | Oncovir | Cancer: malignant brain tumors and astrocytoma; glioblastoma (+temozolomide); non-small-cell lung carcinoma (combined with MUC1-targeting vaccination) Cancer vaccine: glioblastoma (combined with dendritic cell vaccine) Anal dysplasia; smallpox (preclinical) |
| | Poly I: poly C12U (Ampligen) | Hemispherx Biopharma | Infectious diseases: HPV, HIV, hepatitis, and influenza; chronic fatigue syndrome |
| TLR7 | Imiquimod (Aldara) | Meda AB | Cancer: superficial basal cell carcinoma Infectious diseases: genital warts; actinic keratosis |
| | AZD8848 | AstraZeneca and Dainippon Sumitomo Pharma | Asthma and allergic rhinitis (hay fever) |
| | GSK2245035 | GlaxoSmithKline | Allergic airways diseases; asthma |
| | GS-9620 | Gilead | Infectious diseases: HBV, HCV, and HIV infections |
| | TMX-101 (Vesimune) | Telormedix | Cancer: non-muscle invasive bladder cancer |
| TLR7 and TLR8 | R848 (resiquimod) | Meda AB | Cancer vaccine: adjuvant in cancer vaccines for multiple types of tumors |
| TLR8 | VTX-2337 (Motolimod) | VentiRx | Cancer: squamous cell carcinoma of the head and neck (+cetuximab); ovarian cancer |
| | VTX-1463 | VentiRx | Allergic rhinitis |
| TLR9 | Kappaproct | InDex Pharmaceuticals | Ulcerative colitis |
| | DIMS 9054 | InDex Pharmaceuticals | Pulmonary inflammation; multiple sclerosis (preclinical) |

TABLE 1-continued

Clinical development of agonists and antagonists of nucleic acid sensors in human diseases

| Targeted receptor | Compound (name) | Company | Indications |
|---|---|---|---|
| | MGN1703 (dSLIM) | Mologen | Cancer: colorectal cancer; lung carcinoma (small-cell bronchial carcinoma) |
| | MGN1601 | Mologen | Cancer vaccine: MGN1703 plus allogeneic cancer cells; renal cell cancer |
| | AZD1419 | Dynavax and AstraZeneca | Asthma |
| | SD101/CpG-C | Dynavax | Cancer: low-grade B cell lymphoma (combined with low-dose radiation or +ipilimumab); metastatic melanoma (+anti-PD-1); relapsed non-Hodgkin's lymphoma |
| | 1018 (Heplisav-B) | Dynavax Technologies | Infectious diseases: TLR9 agonist (1018 ISS) + hepatitis B surface antigen |
| | CpG 7909 (PF-3512676) | Pfizer | Cancer: mantle cell lymphoma |
| | CpG 7909 (PF-3512676) + BioThrax | Emergent BioSolutions | Anthrax vaccination |
| STING | Cyclic dinucleotides (ADU-S100) | Aduro Biotech | Palpable cancer (preclinical) |
| RIG-I and NOD2 | SB 9200 | Spring Bank Pharmaceuticals | Infectious diseases: HCV and HBV |

CXCL4, CXCL9, CXCL10, and CXCL12 Inhibit the Response of TLR9 in B Cells

As further shown herein, chemokines CXCL4, CXCL9, CXCL10, and CXCL12 inhibit the response of TLR9 in B cells which is the opposite effect as found in pDCs (Example 13). This finding was unpredictable. Without being bound by any theory, this could be explained by the fact that these chemokines use different receptors in different cell types, and additionally, TLRs signal differently in the different cell types. All of these reasons can contribute to why the effects of the chemokines are different in different cell types.

CXCL9, like CXCL4, CXCL10, and CXCL12, belongs to the CXC chemokine family, and is also known as MIG. Sequences for CXCL9 are publicly available (see, for example, GenBank Gene ID 4283).

The ability to control B cell response would be of critical value in autoimmune diseases or in infectious situation. In addition, B cell leukemia are very difficult diseases to treat and controlling B cell proliferation/activation is thus of critical value.

Thus, a further embodiment of the current invention is a method of treating and/or preventing an autoimmune disease in a subject in need thereof by administering a therapeutically effective amount of an agent or agents that antagonizes, inhibits and/or reduces the expression and/or activity of chemokine in B cells, wherein the chemokine inhibits the response of TLR9. In one embodiment, the chemokine is a CXC chemokine. In a further embodiment, the chemokine is chosen from the group consisting of CXCL4, CXCL9, CXCL10, and CXCL12. This blockade of the chemokines which inhibit the TLR9 response is beneficial for autoimmune disease by maintaining an active TLR9 in B cells which is known to be required to eliminate autoreactive B cells.

In this embodiment of the invention, the phrase "in need thereof" indicates a subject has an autoimmune disease, is suspected of having an autoimmune, or has risk factors for an autoimmune disease. Autoimmune diseases that can be treated and/or prevented by this method of the invention, include but are not limited to systemic lupus erythematosus, rheumatoid arthritis, type 1 diabetes, multiple sclerosis, myasthenia gravis, Graves disease, pernicious anemia, scleroderma, psoriasis, inflammatory bowel diseases, Hashimoto's disease, Addison's disease, cutaneous autoimmune disease, systemic sclerosis and Sjögren's syndrome.

Activated B cells are also detrimental in B cell leukemia thus, inhibition of their activation and proliferation would aid in treating these blood cancers.

Thus, a further embodiment of the current invention is a method of treating a B cell leukemia in a subject in need thereof by administering a therapeutically effective amount of an agent or agents that activates and/or increases the expression and/or activity of chemokine in B cells, wherein the chemokine inhibits the response of TLR9. In one embodiment, the chemokine is a CXC chemokine. In a further embodiment, the chemokine is chosen from the group consisting of CXCL4, CXCL9, CXCL10, and CXCL12.

A further embodiment would include administering a therapeutically effective amount of an agent or agents that activates and/or increases the expression and/or activity of chemokine in B cells with another treatment for B cell leukemia. In one embodiment, the chemokine is a CXC chemokine. In a further embodiment, the chemokine is chosen from the group consisting of CXCL4, CXCL9, CXCL10, and CXCL12.

B cell leukemias that can be treated by the methods of the invention include but are not limited to B-cell chronic lymphocytic leukemia/small lymphocytic lymphoma, acute lymphoblastic leukemia, mature B-cell type, B-cell prolymphocytic leukemia, precursor B lymphoblastic leukemia, and hairy cell leukemia.

CXCL4 Potentiates the Response of TLR8 in Macrophages

Lastly, as shown herein, CXCL4 activates the response of TLR8 in macrophages including the induction of IL-6 and TNF. This finding was unpredictable. Without being bound by any theory, this could be explained again by the fact that these chemokines use different receptors in different cell types, and that the TLRs signal differently in the cell types, making the effects different in different cell type. In the case of macrophages, a different TLR (TLR8 versus TLR9) is involved in the response and in macrophages CXCL4 actually blocks IFN and promote IL-6 and TNF. This is the complete opposite as what is seen in pDCs and B cells, reinforcing that these CXCLs are regulators of TLRs in multiple cell types.

Macrophages contribute to the inflammatory status in multiple inflammatory and autoimmune situations through the production of cytokines such as TNF, IL-6 or IL-1s but also IFNs and the control of their activation can be used to treat autoimmune disease as well as allergic rhinitis and asthma.

Thus, a further embodiment of the current invention is a method of treating and/or preventing an autoimmune disease in a subject in need thereof by administering a therapeutically effective amount of an agent or agents that antagonizes, inhibits and/or reduces the expression and/or activity of a CXCL4 in macrophages, wherein the chemokine CXCL4 inhibits the response of TLR8.

Autoimmune and inflammatory diseases that can be treated and/or prevented by the current methods of the invention include but are not limited to systemic lupus erythematosus, rheumatoid arthritis, type 1 diabetes, multiple sclerosis, myasthenia gravis, Graves disease, pernicious anemia, scleroderma, psoriasis, inflammatory bowel diseases, Hashimoto's disease, Addison's disease, cutaneous autoimmune disease, systemic sclerosis and Sjögren's syndrome.

In this embodiment of the invention, the phrase "in need thereof" indicates a subject has an autoimmune disease, is suspected of having an autoimmune, or has risk factors for an autoimmune disease.

Activating and/or Increasing Chemokines

As discussed above, the current invention is based upon the discovery that in some instances increasing chemokines including but not limited to CXCL4, CXCL10, and CXCL12 activate TLR9 responses in pDC, which is beneficial for treating cancer and infectious disease. In other embodiments, increasing CXCL4, CXCL9, CXCL10, and CXCL12 inhibits TLR9 in B cells, which is beneficial for treating leukemia. Methods for increasing expression and/or activity of a protein are well known in the art. Increasing chemokines may be at the transcriptional, translational or post-translational level.

Methods of the current invention include the administration of a therapeutically effective amount of an agent that activates and/or increases the expression and/or activity of chemokines including but not limited to CXCL4, CXCL9, CXCL10, and CXCL12.

Agents can include chemicals, pharmaceuticals, biologics, antibodies, and small organic molecules.

Further agents that can be used in this method include but are not limited to agents for increasing the expression of the gene encoding chemokines including CXCL4, CXCL9, CXCL10, and/or CXCL12; and include nucleic acids which encode the CXCL4, CXCL9, CXCL10, and/or CXCL12 protein, or the entire CXCL4, CXCL9, CXCL10, and/or CXCL12 gene, or a nucleic acid that is substantially homologous to the CXCL4, CXCL9, CXCL10, and/or CXCL12 gene, or a variant, mutant, fragment, homologue or derivative of the CXCL4, CXCL9, CXCL10, and/or CXCL12 gene that produces a protein that maintains or increases their function.

The gene or a nucleic acid which encodes the CXCL4, CXCL9, CXCL10, and/or CXCL12 protein, or a nucleic acid that is substantially homologous to the CXCL4, CXCL9, CXCL10, and/or CXCL12 gene, or a variant, mutant, fragment, homologue or derivative of the CXCL4, CXCL9, CXCL10, and/or CXCL12 gene that produce proteins with maintained or increased function can also be used in the methods of the invention.

The sequences for these chemokines as well as other CXC chemokines can be found on the National Center for Biotechnology Database and can be used to manufacture variants, mutants, fragments, homologues and derivatives which maintain or have increased function.

DNA or other nucleic acids such as mRNA can also be used in the method.

While it would be understood that any agent or agents that increase or upregulate the expression of CXCL4, CXCL9, CXCL10, and/or CXCL12, would also most likely increase CXCL4, CXCL9, CXCL10, and/or CXCL12 proteins, alternatively, an agent or agents that directly increase or promote the activation, amount and/or activity of the proteins can be used in the methods.

Alternatively, administering the proteins can be used in the methods. This includes the administration of a polypeptide, or a variant thereof having at least 90% sequence identity with the CXCL4, CXCL9, CXCL10, and/or CXCL12 polypeptides.

In an embodiment, the variant of the polypeptide has at least 91% sequence identity, or at least 92% sequence identity, or at least 93% sequence identity, or at least 94% sequence identity, or at least 95% sequence identity, or at least 96% sequence identity, or at least 97% sequence identity, or at least 98% sequence identity, or at least 99% sequence identity, with the sequence of the polypeptide of which it is a variant. Thus, preferably, the variant of the polypeptide has at least 91%, 92%, 93%, 94%, 95%, 96%, 97%, 98% or 99% sequence identity with the sequence of the CXCL4, CXCL9, CXCL10, and/or CXCL12 polypeptide. Such variants may be made, for example, using the methods of recombinant DNA technology, protein engineering and site-directed mutagenesis, which are well known in the art, and discussed in more detail below.

The percent sequence identity between two polypeptides may be determined using suitable computer programs.

Biologically active fragments (also referred to as biologically active peptides) or variants include any fragments or variants of a protein that retain an activity of the protein.

Polypeptides, may be prepared using an in vivo or in vitro expression system. Preferably, an expression system is used that provides the polypeptides in a form that is suitable for pharmaceutical use, and such expression systems are known to the skilled person. As is clear to the skilled person, polypeptides of the invention suitable for pharmaceutical use can be prepared using techniques for peptide synthesis.

A nucleic acid molecule encoding, for example, the proteins or variants thereof, may be used to transform a host cell or host organism for expression of the desired polypeptide. Suitable hosts and host cells are known in the art and may be any suitable fungal, prokaryotic or eukaryotic cell or cell line or organism, for example: bacterial strains, including gram-negative strains such as *Escherichia coli* and gram-positive strains such as *Bacillus subtilis* or of *Bacillus brevis*; yeast cells, including *Saccharomyces cerevisiae*; or *Schizosaccharomyces pombe*; amphibian cells such as *Xenopus* oocytes; insect-derived cells, such SF9, Sf21, Schneider and Kc cells; plant cells, for example tobacco plants; or mammalian cells or cell lines, CHO-cells, BHK-cells (for example BHK-21 cells) and human cells or cell lines such as HeLa, as well as all other hosts or host cells that are known and can be used for the expression and production of polypeptides.

The polypeptides or variants thereof, may be made by chemical synthesis, again using methods well known in the art for many years. In certain embodiments, polypeptides for administration to a patient may be in the form of a fusion molecule in which the polypeptide is attached to a fusion partner to form a fusion protein. Many different types of fusion partners are known in the art. One skilled in the art can select a suitable fusion partner according to the intended use of the fusion protein. Examples of fusion partners include polymers, polypeptides, lipophilic moieties, and succinyl groups. Certain useful protein fusion partners include serum albumin and an antibody Fc domain, and certain useful polymer fusion partners include, but are not limited to, polyethylene glycol, including polyethylene glycols having branched and/or linear chains. In certain embodiments, the polypeptide may be PEGylated, or may comprise a fusion protein with an Fc fragment.

In an embodiment, the polypeptide may be fused to or may comprise additional amino acids in a sequence that facilitates entry into cells (i.e. a cell-penetrating peptide). Thus, for example, the CXCL4, CXCL9, CXCL10, and/or CXCL12 or variant thereof or a polypeptide may further comprise the sequence of a cell-penetrating peptide (also known as a protein transduction domain) that facilitates entry into cells. As is well known in the art, cell-penetrating peptides are generally short peptides of up to 30 residues having a net positive charge and act in a receptor-independent and energy-independent manner.

Additionally or alternatively, the polypeptide may be fused to or may comprise additional amino acids in a sequence that facilitates entry into the nucleus (i.e., a nuclear localization sequence (NLS), aka nuclear localization domain (NLD)). Thus, for example, the CXCL4, CXCL9, CXCL10, and/or CXCL12 protein or variant thereof may further comprise the sequence of an NLS that facilitates entry into the nucleus. NLS includes any polypeptide sequence that, when fused to a target polypeptide, is capable of targeting it to the nucleus. Typically, the NLS is one that is not under any external regulation (e.g. calcineurin regulation) but which permanently translocates a target polypeptide to the nucleus.

It is appreciated that the sequence of the cell-penetrating peptide and/or the NLS may be adjacent to the sequence of the protein or variant, or these sequences may be separated by one or more amino acids residues, such as glycine residues, acting as a spacer.

Therapeutic proteins produced as an Fc-chimera are known in the art. For example, Etanercept, the extracellular domain of TNFR2 combined with an Fc fragment, is a therapeutic polypeptide used to treat autoimmune diseases, such as rheumatoid arthritis.

In certain embodiments, the fusion partner may be a polymer, for example, polyethylene glycol (PEG). PEG may comprise branched and/or linear chains. In certain embodiments, a fusion partner comprises a chemically-derivatized polypeptide having at least one PEG moiety attached.

The fusion partner may be attached, either covalently or non-covalently, to the amino-terminus or the carboxy-terminus of the polypeptide. The attachment may also occur at a location within the polypeptide other than the amino-terminus or the carboxy-terminus, for example, through an amino acid side chain (such as, for example, the side chain of cysteine, lysine, histidine, serine, or threonine).

Chemokine receptors belong to the G protein-coupled receptor (GPCR) superfamily. While some data herein has suggested that CXCL4 and CXCL10 are not working through the CXCR3 receptor in pDCs and B cells, the receptor may contribute to the effect and the effects found by CXCL4 and CXCL10 could be mimicked by agonizing the CXCR3 receptor. Thus, the methods of the invention wherein CXCL4, CXCL9, CXCL10, and CXCL12 are activated can be accomplished by agonizing any of the CXC receptors to which one or more the cytokines binds, including but not limited to CXCR3 and CXCR4. Agents for agonizing receptors are known in the art and include small molecules, antibodies, and chemicals.

Antagonizing, Inhibiting, and/or Reducing Chemokines

It has also been shown herein that there are indications wherein inhibiting chemokines, including but not limited to CXCL4, CXCL9, CXCL10, and CXCL12 is beneficial.

Methods and agents for the inhibition of expression and activity of chemokines including CXLC4, CXCL9, CXCL10, and CXCL12 are known in the art.

One such agent for inhibition is a small molecule. A further agent for inhibition is an antibody.

Additional inhibitors of CXCL4, CXCL9, CXCL10, and CXCL12 expression and activity include CXCL4, CXCL9, CXCL10, and CXCL12-specific RNAi, CXCL4, CXCL9, CXCL10, and CXCL12-specific short RNA, CXCL4, CXCL9, CXCL10, and CXCL12-specific antisense (e.g., CXCL4, CXCL9, CXCL10, and CXCL12-specific morpholinos) and triplet-forming oligonucleotides, and CXCL4, CXCL9, CXCL10, and CXCL12-specific ribozymes.

Short RNA molecules include short interfering RNA (siRNA), small temporal RNAs (stRNAs), short hairpin RNA (shRNA), and micro-RNAs (miRNAs). Short interfering RNAs silence genes through an mRNA degradation pathway, while stRNAs and miRNAs are approximately 21 or 22 nucleotide RNAs that are processed from endogenously encoded hairpin-structured precursors, and function to silence genes via translational repression. See, e.g., McManus et al. (2002). *RNA* 8(6):842-50; Morris et al. (2004). *Science* 305(5688):1289-92; He and Hannon. (2004). *Nat. Rev. Genet.* 5(7):522-31.

"RNA interference, or RNAi" a form of post-transcriptional gene silencing ("PTGS"), describes effects that result from the introduction of double-stranded RNA into cells (reviewed in Fire. (1999). *Trends Genet.* 15:358-363; Sharp. (1999) *Genes Dev.* 13:139-141; Hunter. (1999). *Curr. Biol.* 9:R440-R442; Baulcombe. (1999). *Curr. Biol.* 9:R599-R601; Vaucheret et al. (1998). *Plant J.* 16:651-659). The active agent in RNAi is a long double-stranded (antiparallel duplex) RNA, with one of the strands corresponding or complementary to the RNA which is to be inhibited. The inhibited RNA is the target RNA. The long double stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. (2001). *Nature* 411:494-498). In this report, "short interfering RNA" (siRNA, also referred to as small interfering RNA) were applied to cultured cells by transfection in oligofectamine micelles.

These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of CXCL4, CXCL9, CXCL10, and/or CXCL12, siRNAs to the gene encoding CXCL4, CXCL9, CXCL10, and/or CXCL12 can be specifically designed using computer programs. Illustrative nucleotide sequences encoding the amino acid sequences of these components are readily available.

Software programs for predicting siRNA sequences to inhibit the expression of a target protein are commercially available and find use. One program, siDESIGN from Dharmacon, Inc. (Lafayette, Colo.), permits predicting siRNAs for any nucleic acid sequence, and is available on the internet at dharmacon.com. Programs for designing siRNAs are also available from others, including Genscript (available on the internet at genscript.com/ssl-bin/app/rnai) and, to academic and non-profit researchers, from the Whitehead Institute for Biomedical Research found on the worldwide web at "jura.wi.mit.edu/pubint/http://iona.wi.mit.edu/siRNAext/."

Alternatively, double-stranded (ds) RNA is a powerful way of interfering with gene expression in a range of organisms that has recently been shown to be successful in mammals (Wianny and Zernicka-Goetz. (2002), *Nat. Cell. Biol.* 2:70-75). Double stranded RNA corresponding to the sequences of a CXCL4, CXCL9, CXCL10, or CXCL12 polynucleotides can be introduced into or expressed in cells of a candidate organism to interfere with CXCL4, CXCL9, CXCL10, or CXCL12 activity.

MicroRNA can also be used to inhibit CXCL4, CXCL9, CXCL10, and/or CXCL12. MicroRNAs are small non-coding RNAs averaging 22 nucleotides that regulate the expression of their target mRNA transcripts by binding. Binding of microRNAs to their targets is specified by complementary base pairing between positions 2-8 of the microRNA and the target 3' untranslated region (3' UTR), an mRNA component that IFNluences translation, stability and localization. Additionally, this microRNA can also be modified for increasing other desirable properties, such as increased stability, decreased degradation in the body, and increased cellular uptake.

Ribozymes are RNA molecules capable of cleaving targeted RNA or DNA. Examples of ribozymes are described in, for example, U.S. Pat. Nos. 5,180,818; 5,168,053; 5,149,796; 5,116,742; 5,093,246; and 4,987,071, all incorporated herein by reference. Ribozymes specific for CXCL4, CXCL9, CXCL10, or CXCL12 can be designed by reference to the CXCL4, CXCL9, CXCL10, or CXCL12 cDNA sequence.

A further approach is to express anti-sense constructs directed against the polynucleotides of CXCL4, CXCL10, CXCL9, and/or CXCL12 to inhibit gene function.

Antisense oligonucleotides are single-stranded nucleic acids, which can specifically bind to a complementary nucleic acid sequence. By binding to the appropriate target sequence, an RNA-RNA, a DNA-DNA, or RNA-DNA duplex is formed. By binding to the target nucleic acid, antisense oligonucleotides can inhibit the function of the target nucleic acid. Typically, antisense oligonucleotides are 15 to 35 bases in length. However, it is appreciated that it may be desirable to use oligonucleotides with lengths outside this range, for example 10, 11, 12, 13, or 14 bases, or 36, 37, 38, 39 or 40 bases. Thus, with knowledge of the CXCL4, CXCL9, CXCL10, and CXCL12 cDNA sequences, polynucleotide inhibitors of expression can be produced using methods well known in the art.

The antisense molecules may be expressed from any suitable genetic construct and delivered to the subject. Typically, the genetic construct which expresses the antisense molecule comprises at least a portion of the CXCL4, CXCL9, CXCL10, or CXCL12 cDNA or gene operatively linked to a promoter which can express the antisense molecule in the cell. Preferably, the genetic construct is adapted for delivery to a human cell.

Other agents would include antibodies to the components of CXCL4, CXCL9, CXCL10, or CXCL12. Such antibodies are commercially available or can be produced by methods known in the art.

The terms "antibody" and "antibodies" include polyclonal antibodies, monoclonal antibodies, humanized or chimeric antibodies, single chain Fv antibody fragments, Fab fragments, and F(ab')$_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies and humanized antibodies are particularly useful in the present invention.

Antibody fragments that have specific binding affinity for a target of interest can be generated by known techniques. Such antibody fragments include, but are not limited to, F(ab')$_2$ fragments that can be produced by pepsin digestion of an antibody molecule, and Fab fragments that can be generated by reducing the disulfide bridges of F(ab')$_2$ fragments. Alternatively, Fab expression libraries can be constructed. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments recognizing a target of interest can be produced through standard techniques, such as those disclosed in U.S. Pat. No. 4,946,778.

The inhibitor of CXCL4, CXCL9, CXCL10, and/or CXCL12 should inhibit at least one function or activity of naturally-occurring variants of human CXCL4, CXCL10, or CXCL12 in which one or more of the amino acid residues have been replaced with another amino acid.

It is also appreciated that the CXCL4, CXCL9, CXCL10, and/or CXCL12 inhibitor may be one that inhibits at least one function or activity of an orthologue of CXCL4, CXCL9, CXCL10, and/or CXCL12 in another species, for example CXCL4, CXCL9, CXCL10, and/or CXCL12 from a horse, dog, pig, cow, sheep, rat, mouse, guinea pig or a primate. It will be appreciated, that when the inhibitor is administered to a particular individual, the inhibitor is one that modulates at least one function or activity of CXCL4, CXCL9, CXCL10, and/or CXCL12 from the same species as that individual. Thus, when the patient is a human patient, the inhibitor inhibits at least one function or activity of human CXCL4, CXCL9, CXCL10, or CXCL12, and so on.

Methods and routes of administering polynucleotide inhibitors, such as siRNA molecules, antisense molecules and ribozymes, to a patient, are well known in the art and described in more detail below. It is appreciated that polynucleotide inhibitors of CXCL4, CXCL9, CXCL10, and/or CXCL12 may be administered directly, or may be administered in the form of a polynucleotide that encodes the inhibitor. Thus, as used herein, unless the context demands otherwise, by administering to the individual an inhibitor of CXCL4, CXCL9, CXCL10, and/or CXCL12 which is a polynucleotide, includes the meanings of administering the inhibitor directly, or administering a polynucleotide that encodes the inhibitor, typically in the form of a vector.

In a further embodiment, the inhibitor may be a dominant-negative mutant of CXCL4, CXCL9, CXCL10, and/or CXCL12. As well as those mentioned above, the dominant-negative mutant may have a mutated or deleted DNA binding domain (DBD).

Suitable methods, routes and compositions for preparing polypeptide inhibitors of CXCL4, CXCL9, CXCL10, and/or CXCL12 and nucleic acid molecules that encode them and administering them to a patient are known in the art and described below, and include viral vectors such as adenoviral vectors.

Administration of Agents and Compositions

When the CXCL4, CXCL9, CXCL10, and/or CXCL12 inhibitor or activator is a nucleic acid such as DNA, RNA, interfering RNA or microRNA, methods for delivery include receptor mediated endocytosis where the nucleic acid is coupled to a targeting molecule that can bind to a specific cell surface receptor, inducing endocytosis and transfer of the nucleic acid into cells. Coupling is normally achieved by covalently linking poly-lysine to the receptor molecule and then arranging for (reversible) binding of the negatively charged DNA or RNA to the positively charged poly-lysine component. Another approach utilizes the transferrin receptor or folate receptor which is expressed in many cell types. When producing the microRNA for this method of administration, the microRNA could be manufactured to have a guide strand which is identical to the microRNA of interest and a passenger strand that is modified and linked to a molecule for increasing cellular uptake Another method to administer the nucleic acid to the proper tissue is direct injection/particle bombardment, where the nucleic acid is be injected directly with a syringe and needle into a specific tissue, such as muscle, skin or tumor, and can be delivered by administration including intravenous, intradermal, and subcutaneous injection.

An alternative direct injection approach uses particle bombardment ('gene gun') techniques: nucleic acid is coated on to metal pellets and fired from a special gun into cells. Successful gene transfer into a number of different tissues has been obtained using this approach. Such direct injection techniques are simple and comparatively safe.

Another method for delivery of nucleic acid to the proper tissue or cell is by using adeno-associated viruses (AAV). Nucleic acid is delivered in these viral vectors is continually expressed, replacing the expression of the DNA or RNA that is not expressed in the subject. Also, AAV have different serotypes allowing for tissue-specific delivery due to the natural tropism toward different organs of each individual AAV serotype as well as the different cellular receptors with which each AAV serotype interacts. The use of tissue-specific promoters for expression allows for further specificity in addition to the AAV serotype.

Other mammalian virus vectors that can be used to deliver the DNA or RNA include oncoretroviral vectors, adenovirus vectors, Herpes simplex virus vectors, and lentiviruses.

Liposomes are spherical vesicles composed of synthetic lipid bilayers which mimic the structure of biological membranes. The nucleic acid to be transferred is packaged in vitro with the liposomes and used directly for transferring the nucleic acid to a suitable target tissue in vivo. The lipid coating allows the nucleic acid to survive in vivo, bind to cells and be endocytosed into the cells. Cationic liposomes (where the positive charge on liposomes stabilize binding of negatively charged DNA), have are one type of liposome.

The nucleic acid can also be administered with a lipid to increase cellular uptake. The nucleic acid may be administered in combination with a cationic lipid, including limited to, lipofectin, DOTMA, DOPE, and DOTAP.

Other lipid or liposomal formulations including nanoparticles and methods of administration have been described as for example in U.S. Patent Publication 2003/0203865, 2002/0150626, 2003/0032615, and 2004/0048787. Methods used for forming particles are also disclosed in U.S. Pat. Nos. 5,844,107, 5,877,302, 6,008,336, 6,077,835, 5,972,901, 6,200,801, and 5,972,900.

The polypeptide or nucleic acid molecule for administration to the patient may be formulated as a nanoparticle. Nanoparticles are a colloidal carrier system that has been shown to improve the efficacy of an encapsulated drug by prolonging the serum half-life. Polyalkylcyanoacrylates (PACAs) nanoparticles are a polymer colloidal drug delivery system that is in clinical development (described, for example, by Stella et al. (2000) J. Pharm. Sci., 89: 1452-1464; Brigger et al. (2001) Int. J. Pharm 214: 37-42; Calvo et al. (2001) Pharm. Res. 18: 1157-1166; and Li et al. (2001) Biol. Pharm. Bull. 24: 662-665). Biodegradable poly(hydroxyl acids), such as the copolymers of poly(lactic acid) (PLA) and poly(lactic-co-glycolide) (PLGA) are being extensively used in biomedical applications and have received FDA approval for certain clinical applications. In addition, PEG-PLGA nanoparticles have many desirable carrier features including (i) that the agent to be encapsulated comprises a reasonably high weight fraction (loading) of the total carrier system; (ii) that the amount of agent used in the first step of the encapsulation process is incorporated into the final carrier (entrapment efficiency) at a reasonably high level; (iii) that the carrier has the ability to be freeze-dried and reconstituted in solution without aggregation; (iv) that the carrier be biodegradable; (v) that the carrier system be of small size; and (vi) that the carrier enhances the particles persistence. Nanoparticles may be synthesized using virtually any biodegradable shell known in the art. In one embodiment, a polymer, such as poly(lactic-acid) (PLA) or poly(lactic-co-glycolic acid) (PLGA) is used. Such polymers are biocompatible and biodegradable, and are subject to modifications that desirably increase the photochemical efficacy and circulation lifetime of the nanoparticle. In one embodiment, the polymer is modified with a terminal carboxylic acid group (COOH) that increases the negative charge of the particle and thus limits the interaction with negatively charged nucleic acids. Nanoparticles may also be modified with polyethylene glycol (PEG), which also increases the half-life and stability of the particles in circulation. Alternatively, the COOH group may be converted to an N-hydroxysuccinimide (NHS) ester for covalent conjugation to amine-modified compounds.

Other protein modifications to stabilize a polypeptide, for example to prevent degradation, as are well known in the art may also be employed. Specific amino acids may be modified to reduce cleavage of the polypeptide in vivo. Typically, N- or C-terminal regions are modified to reduce protease activity on the polypeptide. A stabilizing modification is any modification capable of stabilizing a protein, enhancing the in vitro half life of a protein, enhancing circulatory half life of a protein and/or reducing proteolytic degradation of a protein. For example, polypeptides may be linked to the serum albumin or a derivative of albumin. Methods for linking polypeptides to albumin or albumin derivatives are well known in the art.

It is appreciated that the compounds for administration to a patient, for example as described above, will normally be formulated as a pharmaceutical composition, i.e. together with a pharmaceutically acceptable carrier, diluent or excipient.

The phrase "pharmaceutically acceptable" refers to molecular entities and compositions that are physiologically tolerable and do not typically produce an allergic or similar untoward reaction, such as gastric upset, dizziness and the like, when administered to a human, and approved by a regulatory agency of the Federal or a state government or listed in the U.S. Pharmacopeia or other generally recognized pharmacopeia for use in animals, and more particularly in humans. "Carrier" refers to a diluent, adjuvant, excipient, or vehicle with which the therapeutic is administered. Such pharmaceutical carriers can be sterile liquids, such as saline solutions in water and oils, including those of petroleum, animal, vegetable, or synthetic origin, such as peanut oil, soybean oil, mineral oil, sesame oil, and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition, if desired, can also contain minor amounts of wetting or emulsifying agents, or pH buffering agents.

Preferred methods of administration include oral; mucosal, such as nasal, sublingual, vaginal, buccal, or rectal; parenteral, such as subcutaneous, intravenous, bolus injection, intramuscular, or intraarterial; or transdermal administration to a subject. Most preferred method of administration are parenteral and oral.

These administrations can be performed using methods standard in the art. Oral delivery can be performed by complexing a therapeutic composition of the present invention to a carrier capable of withstanding degradation by digestive enzymes in the gut of an animal. Examples of such carriers, include plastic capsules or tablets, such as those known in the art. One method of local administration is by direct injection. Administration of a composition locally within the area of a target cell refers to injecting the composition centimeters and preferably, millimeters from the target cell or tissue. The inhibitor may be provided in any suitable form, including without limitation, a tablet, a powder, an effervescent tablet, an effervescent powder, a capsule, a liquid, a suspension, a granule or a syrup.

The co-administration of the agents can be by any administration described herein. Moreover, it can be in one composition, or in more than one composition. The administration of the agents can be simultaneous, concurrently or sequentially.

Alternatively, a further embodiment of the invention provides methods of ex vivo cell therapy, wherein a population of cells is obtained, contacted, incubated or treated with one of the agents disclosed herein, and then administered back to the subject in need thereof.

In some embodiments, the cells (pDCs, B cells or macrophages) are obtained from a subject, such as a mammalian subject. In some embodiments, the mammalian subject is a non-human primate, a rodent (e.g., mouse or rat), a bovine, a porcine, an equine, or a domestic animal. In some embodiments, the cells are obtained from a healthy donor. In some embodiments, the cells are obtained from the subject to whom the treated cells will be subsequently administered. Cells that are administered to the same subject from which the cells were obtained are referred to as autologous cells, whereas cells that are obtained from a subject who is not the subject to whom the cells will be administered are referred to as allogeneic cells.

Cells may be obtained from any suitable source using convention means known in the art. In some embodiments, cells are obtained from a sample from a subject, such as skin sample or a blood sample.

pDCs, B cells or macrophages can be mobilized into the circulating blood by administering a mobilizing agent in order to harvest the cells from the peripheral blood. The number of the cells collected following mobilization using a mobilizing agent is typically greater than the number of cells obtained without use of a mobilizing agent.

In some embodiments, a sample is obtained from a subject and is then enriched for a desired cell type, e.g., pDC—$CD14^-HLA-DR^+CD11c^-CD123^+BDCA4^+$. As shown in Example 1, pDCs, B cells and macrophages can be obtained from PBMCs isolated from blood as described herein. Cells can also be isolated from other cells, for example by isolation and/or activation with an antibody binding to an epitope on the cell surface of the desired cell type. Another method that can be used includes negative selection using antibodies to cell surface markers to selectively enrich for a specific cell type without activating the cell by receptor engagement.

In particular, when the method of the invention is used to treat SSc, pDCs can be obtained from the skin tissue of the subject in need thereof. When the method of the invention is used to treat some cancers, the cells can be injected or administered into the tumor tissue or systemically into the blood. Similarly, when used to treat infectious disease, the cells can be administered into the blood of the subject.

Populations of the cells can be expanded prior to or after treatment, contact or incubation with the desired agent or agents. The cells may be cultured under conditions that comprise an expansion medium. The cell may be expanded for about 1, 2, 3, 4, 5, 6, 7, 8, 9, 10, 11, 12, 13, 14, 15, 16, 17, 18, 19, 20, 21, 22, 23, 24, 25 days or any range necessary.

The cells may be autologous to the subject, i.e., the cells are obtained from the subject in need of the treatment, treated, contact and/or incubated with the agents described herein, and then administered to the same subject. Administration of autologous cells to a subject may result in reduced rejection of the host cells as compared to administration of non-autologous cells. Alternatively, the host cells are allogeneic cells, i.e., the cells are obtained from a first subject, treated, contact and/or incubated with the agents described herein and administered to a second subject that is different from the first subject but of the same species. For example, allogeneic immune cells may be derived from a human donor and administered to a human recipient who is different from the donor.

A typical amount of cells, i.e., administered to a mammal (e.g., a human) can be, for example, in the range of one million to 100 billion cells; however, amounts below or above this exemplary range are also within the scope of the present disclosure. For example, the daily dose of cells can be about 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), preferably about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), more preferably about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells, or a range defined by any two of the foregoing values).

Also within the scope of the present disclosure are multiple administrations (e.g., doses) of the agents and/or populations of cells. In some embodiments, the agents and/or populations of cells are administered to the subject once. In some embodiments, agents and/or populations of cells are administered to the subject more than once (e.g., at least 2, 3, 4, 5, or more times). In some embodiments, the agents and/or populations of cells are administered to the subject at a regular interval, e.g., every six months.

The present invention further comprises pharmaceutical compositions comprising the cells treated, incubated or contacted with agents using the methods of the invention for the treatment of disease. These cells include plasmacytoid dendritic cells, B cells and macrophages treated, incubated or contacted with agents using the methods of the invention.

Kits

Also within the scope of the present disclosure are kits for practicing the method of the invention. Such kits may include agents that activates or increases the expression and/or activity of a chemokines, and toll-like receptors. Such kits may include agents that antagonize or decrease the expression and/or activity of a chemokine.

In some embodiments, the kit can comprise instructions for use in any of the methods described herein. The included instructions can comprise a description of administration of the agents to a subject to achieve the intended activity in a subject. The kit may further comprise a description of selecting a subject suitable for treatment based on identifying whether the subject is in need of the treatment.

The instructions relating to the use of the agents described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the pharmaceutical compositions are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device, such as an inhaler, nasal administration device, or an infusion device. A kit may have a sterile access port (for example, the container may be an intravenous solution bag or a vial having a stopper pierceable by a hypodermic injection needle). The container may also have a sterile access port.

Kits optionally may provide additional components such as buffers and interpretive information. Normally, the kit comprises a container and a label or package insert(s) on or associated with the container. In some embodiment, the disclosure provides articles of manufacture comprising contents of the kits described above.

EXAMPLES

The present invention may be better understood by reference to the following non-limiting examples, which are presented in order to more fully illustrate the preferred embodiments of the invention. They should in no way be construed to limit the broad scope of the invention.

Example 1—Materials and Methods

Study Design

Systemic Sclerosis (SSc) patients between 21 and 79 years of age, SLE patients between 25 and 54 years of age and healthy donors (HD) between 27 and 60 years of age were included in the human study. Patients were treated with a variety of therapies. However, they were excluded from the B cell analysis if they received rituximab, and they were excluded from the TLR assays if they were treated with hydroxychloroquine. No blinding or randomization was performed for the human studies. For in vivo studies, 8-12 week old female mice were used. Immunohistochemistry and immunostaining analyses were performed in a blinded manner.

Mice and Bleomycin Model

C57BL/6 and C-type lectin domain family 4, member C2-diphtheria toxin receptor transgenic (CLEC4C-DTR) mice (Rowland et al. 2014) and TLR7ko mice were obtained from The Jackson Laboratory, and the TLR8Tg were generated as described (Guiducci et al. 2013). Skin fibrosis was induced using the bleomycin (BLM)-induced model as originally described by Yamamoto (Yamamoto et al. 1999; Batteaux et al. 2011) and adapted for better consistency (Chia et al. 2016). BLM treatment can induce skin fibrosis in a small (about 1 cm) area at the site of injection with a prevalence of almost 100%. Mice (female 8-12 weeks-old) received daily subcutaneous injections for 3-5 weeks in 3 adjacent spots on the shaved lower back either with 60 µg (100 µl) of filter-sterilized BLM or PBS. In order to deplete pDCs, CLEC4C-DTR mice were injected twice weekly by intraperitoneal injection with 400 ng of diphtheria toxin (DT). Injections started either 1 day before and during the 4 weeks of experimental fibrosis, or started at 3 weeks after the start of the BLM injections and continued for the remaining 2 weeks (BLM treatment was not interrupted). The depletion efficiency was confirmed by flow cytometry analysis of pDCs (B220$^+$pDCsA-1$^+$) in the spleen.

All animal procedures were performed in accordance with the regulations of the Institutional Animal Care and Use Committee of the Hospital for Special Surgery and Weill Cornell Medical College.

Patients

Participants were recruited from the IRB-approved Hospital for Special Surgery Scleroderma or Systemic Lupus Erythematosus Registries. Patients and healthy volunteers provided written IFNormed consent before enrollment. All SSc patients fulfilled the 2013 ACR/EULAR Classification Criteria for SSc (van den Hoogen et al. 2013). Patients were categorized as having limited cutaneous (lcSSc) or diffuse cutaneous (dcSSc) subtype of SSc according to LeRoy (LeRoy and Medsger 2001). Disease duration was defined as the time from the first SSc related symptom apart from the Raynaud phenomenon and was classified as early if the disease duration was ≤2 years. The clinical and demographic characteristics of the SSc patients are described in Table 2.

All SLE patients fulfilled the 1997 ACR criteria (Hochberg 1997) and its complementary criteria, the 2012 Systemic Lupus International Collaborating Clinics (SLICC) criteria for SLE patients (petri. The clinical and demographic characteristics of the SLE patients are described in Table 3.

TABLE 2

Clinical and demographic characteristics of the SSc patients

| | |
|---|---|
| Age - years, mean (SD) | 51.32 (12.82) |
| Sex -n, % female | 61, 77.2% |
| Race - number, percentage | 55, 69.6% Caucasian |
| | 18, 22.8% African American |
| | 5, 6.3% Asian |
| Disease Duration - years, mean (SD) | 5.6 (4.9) |
| Scleroderma subtype - n, % diffuse, | 62, 78.5% |
| n, % limited | 13, 16.5% |
| MRSS - mean (SD) | 16.4 (11) |
| Autoantibody - n, % scl70, | 28, 35.4% Scl70 |
| n, % RNA Polymerase 3, | 21, 26.6% POL3 |
| n, % centromere, | 11, 13.9% CENB |
| n, % RNP | 4, 5.06% RNP |
| Interstitial lung disease present - n, % | 43, 54.4% |
| Pulmonary hypertension present - n, % | 8, 10.1% |

TABLE 3

Clinical and demographic characteristics of the SLE patients

| | |
|---|---|
| Age-years, mean (SD) | 40.67 (10.98) |
| Sex -n, % female | 5, 83.33% |
| Race - number, percentage | 2, 33.3% Caucasian |
| | 2, 33.3% African American |
| | 2, 33.3% Asian |
| Disease Duration - years, mean (SD) | 15 (3.29) |
| ACR criteria-n, % | 3, 50% |
| Malar Rash | 0, 0% |
| Discoid Rash | 3, 50% |
| Photosensitivity | 3, 50% |
| Oral Ulcers | 5, 83% |
| Arthritis | 3, 50% |
| Serositis | 2, 33% |
| Renal Disorder | 0, 0% |
| Neurologic Disorder | 6, 100% |
| Hematologic Disorder | 5, 83% |
| Immunologic Disorder | 6, 100% |
| Positive ANA | |
| Positive Titer of anti-dsDNA-n, % total | 3, 50% |
| 1+ positive | 1 |
| 2+ positive | 1 |
| 3+ positive | 1 |
| 4+ positive | 0 |
| History of positive anti-RBP-n, % total | 4, 66.67% |
| Anti-Ro | 3 |
| Anti-La | 1 |
| Anti-Sm | 0 |
| Anti-RNP | 3 |
| SLEDAI-mean(SD) | 4.5 (2.43 |

Skin Fibrosis Evaluation and Gene Expression Analysis

After 4 weeks of BLM injections, the skin was harvested and fibrosis evaluated by determining dermal thickness—defined as the thickness of the skin from the top of the granular layer to the junction between the dermis and subcutaneous fat—by a blinded observer using NIS Elements software (Nikon). Images were captured using a Nikon Eclipse microscope coupled to a Nikon camera. For this, the skin was fixed in Clear-Rite3 (ThermoScientific), then dehydrated successively and embedded in paraffin. Five-micrometer sections were cut, rehydrated, and stained with Trichrome Masson (Sigma-Aldrich).

Skin collagen and protein content was quantified using Total Collagen Kit and Total Protein Assay respectively (QuickZyme Biosciences) according to the manufacturer's protocol. Five 10 µm sections from paraffin-embedded samples were used for collagen and protein extraction. Collagen levels were normalized to the total protein amount. For visualization of α-Smooth Muscle actin (α-SMA)-positive cells in skin, paraffin-embedded 5 µm sections were rehydrated before antigen retrieval at 100° C. in 10 mM citrate buffer, pH 6.0, for 15 minutes and then stained as indicated. α-SMA was detected with mouse anti-α-SMA (Sigma-Aldrich) and M.O.M. (mouse on mouse) Imm-PRESS Anti-Mouse IgG (Vector labs) and counterstained with hematoxylin (Fischer Scientific). The secondary antibody was revealed with a 3,3'-diaminobenzidine (DAB) substrate kit (Vector laboratories). α-SMA$^+$ cells (brown) were counted on the whole slide and the results were expressed as a ratio of the number of α-SMA$^+$ cells per total surface area of the section.

RNA was extracted from skin samples using the Qiagen RNeasy Mini Kit. Quantity of RNA was measured by Nanodrop and gene levels quantified using a NanoString panel according to the manufacturer's protocol using 100 ng total RNA (NanoString Technologies).

In Situ mRNA Hybridization Analysis

In situ RNA hybridization for mouse Siglech and Pf4 mRNA was performed on sections from FFPE mouse skin samples using the RNAscope technology (Advanced Cell Diagnostics) following the manufacturer's instructions (RNAscope 2.5 HD duplex detection reagents; RNAscope 2.5 HD detection reagents BROWN). The following probes were adopted: Probe Mm Pf4-C1, targeting 2-586 of NM_019932.4; Probe Mm Siglech-C2, targeting region 2-1359 of NM_178706.4. Probe targeting bacterial Dapb, 414-862 of EF191515 was used as negative control. Slides were counterstained with Gill's hematoxylin (Bioptica). Slides were evaluated under an AXIO Scope A1 optical microscope (Zeiss). Quantitation of cells expressing Pf4 in mouse skin samples was performed as described below for Siglec-H immunohistochemistry. Microphotographs were collected through an Axiocam 503 Color digital camera (Zeiss) using the Zen2 software Immunohistochemical Analysis For immunohistochemical analyses, skin biopsy samples from SSc patients and normal skin samples were selected from the archives of the Tumor Immunology Laboratory of the Department of Health Science, University of Palermo, Italy. For all the archival specimens, patient's IFNormed consent was available. Samples included in the study were handled in an anonymous fashion and according to the declaration of Helsinki; immunohistochemical data do not allow patients' identification or provide any IFNormation on patients' genetics.

From both human and mouse formalin-fixed and paraffin-embedded (FFPE) skin samples, four-micrometers-thick sections were cut and put onto slides. The antigen unmasking was performed using Novocastra Epitope Retrieval Solutions pH 9 in a PT Link pre-treatment module (Dako) at 98° C. for 30 minutes.

The sections were brought to room temperature and washed in PBS. After neutralization of the endogenous peroxidases with 3% H2O2 and Fc blocking by a specific protein block (Novocastra), the slides were incubated overnight with the following primary antibodies at 4° C.: monoclonal anti-human CD123 (Clone BR4MS; dilution 1:100 pH9; Leica Novocastra); monoclonal anti-mouse Siglec-h (Clone 23M14A10; dilution 1:100 pH9; LSBio LifeSpan BioSciences). Primary antibody binding was revealed by either Novolink polymer detection system (Leica Biosystems) or Super Sensitive Multi Link Alkaline Phosphatase (Biogenex Lot. QA9000417) using AEC (3-amino-9-ethyl-carbazole) (Dako) or Vulcan Fast Red (Biocare Medical) as chromogenic substrates, respectively.

The slides were counterstained with Harris hematoxylin (Novocastra) and analyzed under an AXIO Scope A1 optical microscope (Zeiss).

For quantitation of Siglec-h-immunostained cells in mouse skin samples, positive cells were counted out of 10 non-overlapping high-power microscopic fields (×400) from dermal (5 HPFs) and hypodermal (5 HPFs) areas by an expert pathologist (C.T.). Microphotographs were collected through an Axiocam 503 Color digital camera (Zeiss) using the Zen2 software.

Purification of Mouse pDCs and Macrophages

Splenocytes from WT or Tg8 mice receiving either PBS or BLM for 4 weeks were prepared using standard procedures. Cells were stained with F4/80, CD11b, B220, SiglecH and BST2 antibodies and macrophages (F4/80$^+$, CD11b$^+$) or pDCs (cells positive for F4/80 or CD11b were first excluded and pDCs identified as B220$^+$, SiglecH$^+$, BST2$^+$) were purified using a BD IFNLUX cell sorter.

Purification of Cell Types from SSc and SLE Patients or Healthy Donors

PBMCs were prepared using Ficoll-Paque density gradient from fresh blood under internal Institutional Review Board—approved protocols. pDCs were isolated as previously described (Guiducci et al. 2008) using either using negative depletion (Miltenyi Biotech) or following cell sorting using a BD IFNLUX cell sorter. As part of the gating strategy, neutrophils were excluded by FSC/SSC and cells positive for CD14 (CD3 and CD19 as well) were first excluded in order to prevent the contamination by TLR8 positive cells and then positively gated on HLA-DR, CD123 and BDCA4 to purify the pDCs. All BDCA4+ cells also express BDCA2 (results not shown). As a result, pure pDCs were obtained and no markers for neutrophils (CD66) or myeloid cells were found by PCR. B cells were FACS sorted as CD19+ and monocytes as CD14+ cells. PBMCs were depleted of pDCs using BDCA4 beads from Miltenyi. pDCs were cultured at 10,000-30,000 cells per well in a 96-round bottom plate and incubated at 37° C., 5% CO2 and 95% humidity. After 24 hours of culture, the supernatant was collected for ELISA or Mutiplex cytokine assays. In some culture conditions, cells were cultured with the PI3Kδ inhibitor, CAL-101 (Selleck chemicals) for 24 hours. The RNA-based TLR8 agonist, ORN8-L previously described (Guidacci et al. 2013) was synthetized by Chemgenes Corporation. For the TLR8 activation assay, pDCs were incubated in complete media alone, 200 μg/ml ORN8-L in complete media or 200 μg/ml ORN8-L+ 10 μg/ml CXCL4 (R&D systems).

Primary human CD14+ Monocytes were obtained from peripheral blood, using antiCD14 magnetic beads, as recommended by the manufacturer (Miltenyi Biotec). Monocytes were cultured in RPMI 1640 medium (Invitrogen) supplemented with 10% heat-inactivated defined FBS (HyClone Fisher), penicillin/streptomycin (Invitrogen), L-glutamine (Invitrogen), and 10 ng/ml human macrophage colony-stimulating factor (M-CSF; Peprotech).

For TLR7 and TLR9 activation assay, pDCs were stimulated with heat-inactivated 2 MOI of H1N1 VR-95 IFNluenza A virus (ATCC) and 0.5 μM of C274 (Guidacci et al. 2006) respectively.

Flow Cytometry Staining and Analysis

PBMCs were resuspended in FACS buffer and incubated with FcR blocking reagent (Miltenyi Biotec) for 10 minutes at 4° C. The cells were then stained with the following monoclonal antibodies: CD14, CD19, HLA-DR, CD11c, CD86, CD83 (BD biosciences) and BDCA4 and CD123 (Miltenyi Biotec) for 15 minutes at 4° C. and washed twice in FACS buffer. Cells were acquired by a fluorescence activated cell sorter (FACS) Canto flow cytometer (BD Biosciences) and analysis was performed using FlowJo analysis software (TreeStar Inc.). The gating strategy involved progressively measuring total cells, viable cells only by FSC/SSC and specific cell types. For every sample, 100,000 nucleated cells were acquired and values are expressed as percentage of viable cells, as gated by forward- and side-scatter. The pDCs were defined as CD14$^-$HLA-DR$^+$CD11c$^-$CD123$^+$BDCA4$^+$ while cDCs were CD14$^-$HLA-DR$^+$CD123$^-$ BDCA4$^-$CD11c$^+$. CD86 and CD83 mean fluorescence intensity (MFI) was measured on pDCs as defined above. Monocytes and B cells were determined as above.

Real-Time Quantitative PCR Analysis

PCR reactions were performed as described previously with 10 ng of cDNA (Barrat et al. 2005). In brief, RNA was extracted from cells using the Qiagen RNeasy Mini Kit. Quantity of RNA was measured by Nanodrop and high-capacity cDNA Reverse Transcription kit was used to generate 20-50 ng cDNA. Gene expression levels were calculated based on relative threshold cycle (Ct) values. This was done using the formula Relative Ct=100×1.8 (HSK-GENE), where HSK is the mean CT of duplicate housekeeping gene runs (we used Ubiquitin), GENE is the mean CT of duplicate runs of the gene of interest, and 100 is arbitrarily chosen as a factor to bring all values above 0.

Primers were obtained from Fischer Scientific and were as follows:

```
hCXCL4, forward:
                                     (SEQ ID NO: 1)
CACTGCCCAACTGATAGCCA;

hCXCL4, reverse:
                                     (SEQ ID NO: 2)
AGCCAACATGTAACACCAAGC;

hTLR7, forward:
                                     (SEQ ID NO: 3)
TTACCTGGATGGAAACCAGCTACT;

hTLR7, reverse:
                                     (SEQ ID NO: 4)
TCAAGGCTGAGAAGCTGTAAGCTA;

hTLR8, forward:
                                     (SEQ ID NO: 5)
AACTTTCTATGATGCTTACATTTCTTATGAC;

hTLR8, reverse:
                                     (SEQ ID NO: 6)
GGTGGTAGCGCAGCTCATTT;

hTLR9, forward:
                                     (SEQ ID NO: 7)
TGAAGACTTCAGGCCCAACTG;

hTLR9, reverse:
                                     (SEQ ID NO: 8)
TGCACGGTCACCAGGTTGT;

hTLR10, forward:
                                     (SEQ ID NO: 9)
TTTGATCTGCCCTGGTATCTCA;

hTLR10, reverse:
                                     (SEQ ID NO: 10)
AGTTGTTCTTGGGTTGTTTTCCTAAC;
```

-continued hUBI, forward:
CACTTGGTCCTGCGCTTGA; (SEQ ID NO: 11)

hUBI, reverse:
CAATTGGGAATGCAACAACTTTAT; (SEQ ID NO: 12)

hCXCR3B, forward:
TGCCAGGCCTTTACACAGC; (SEQ ID NO: 13)

hCXCR3B reverse:
TCGGCGTCATTTAGCACTTG; (SEQ ID NO: 14)

mUBI, forward:
TGGCTATTAATTATTCGGTCTGCAT; (SEQ ID NO: 15)

Chemokine and Cytokine Measurement

Supernatant from pDCs 24 hour culture was used for quantification of secreted chemokines and cytokines and measured with the use of an enzyme-linked immunosorbent assay (ELISA) or Luminex multiplex-beads immunoassay. CXCL4 ELISA (Ray Biotech) and IFNα, IP-10, IL-6, TNF Luminex assay (Millipore) was performed according to the manufacturer's protocol. Due to the variability in the number of cells obtained from the different patients and so we could compare the values across donors, all results were normalized to 10,000 cells. Of note, for all donors, pDCs were plated between 10,000-30,000 cells.

Statistical Analysis

Data were analyzed using a Mann-Whitney U-test (t test using non parametric criteria for independent samples). Comparisons between PBMC and pDCs-depleted PBMC were tested using a parametric paired t-test. All analyses were performed using Prism software (GraphPad Software). Differences were considered significant at a P level less than 0.05 with *p<0.05; p<0.01; *p<0.001.

Example 2—pDCs Infiltrated the Skin of SSc Patients and were Chronically Activated with Spontaneous Secretion of CXCL4 and IFN-α

Figure 1B:
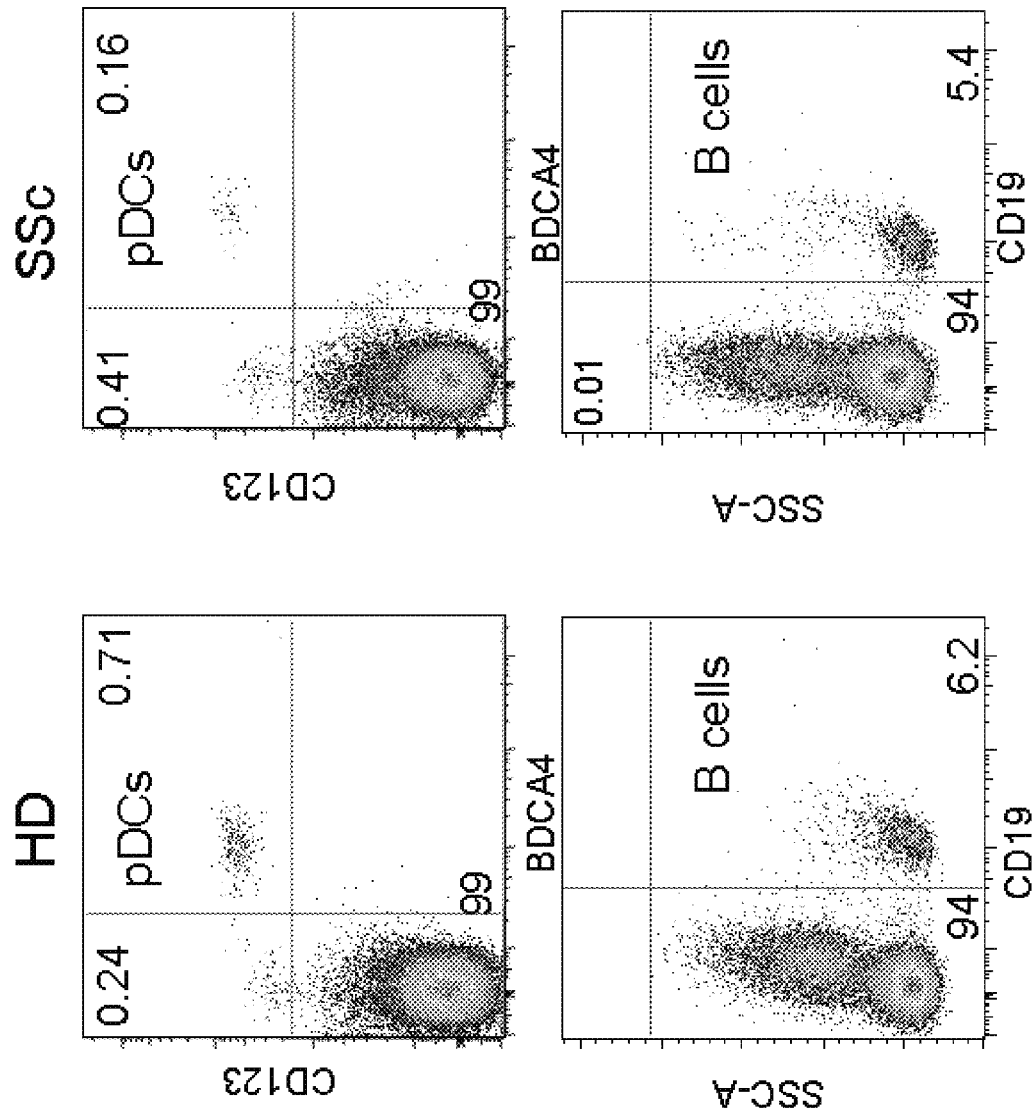
FIG. 1B are representative dot plots of pDCs, B cells, cDCs and monocytes from PBMCs from HDs or SSc patients analyzed by flow cytometry.
Figure 1B:
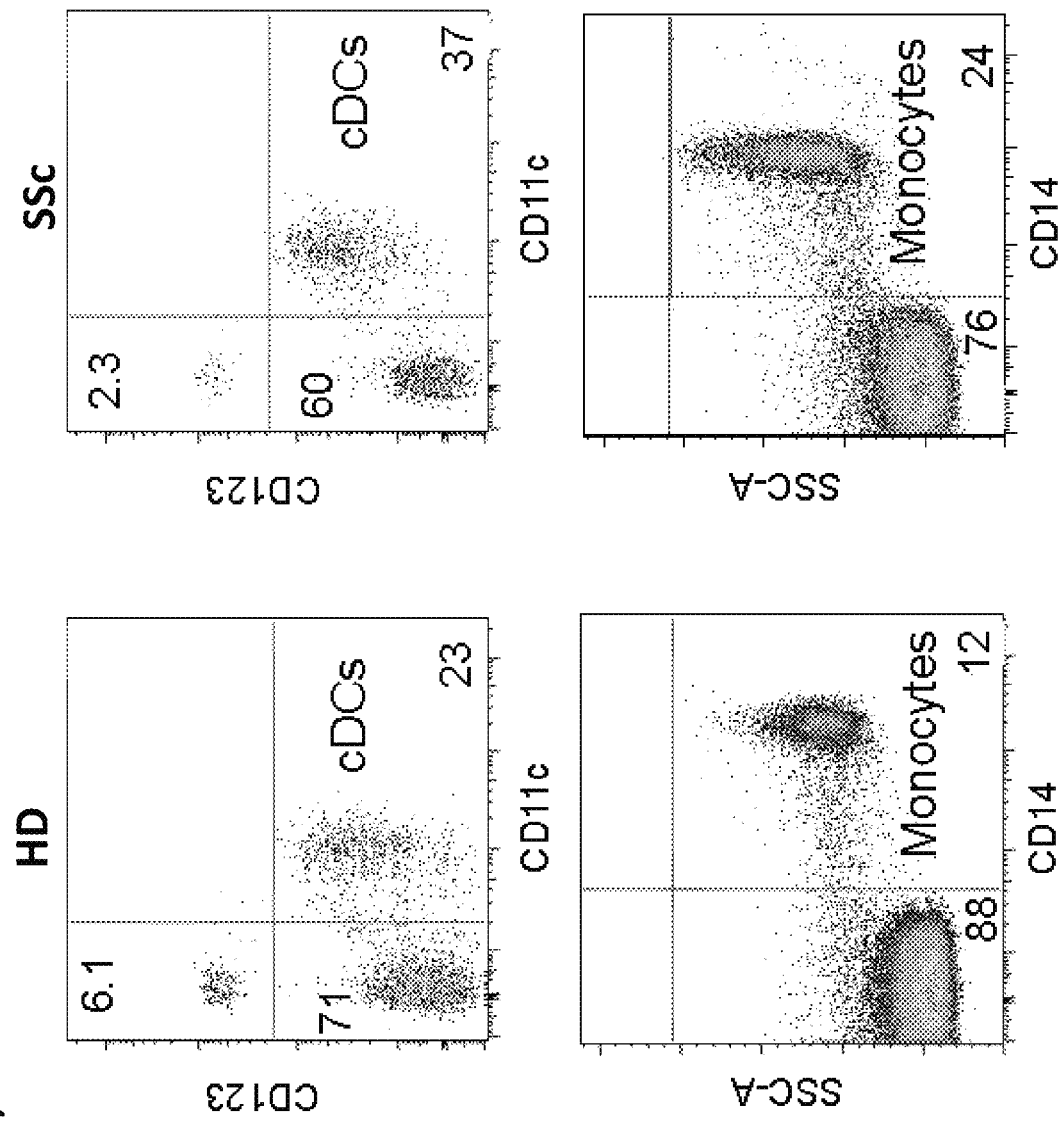
Figure 1C:
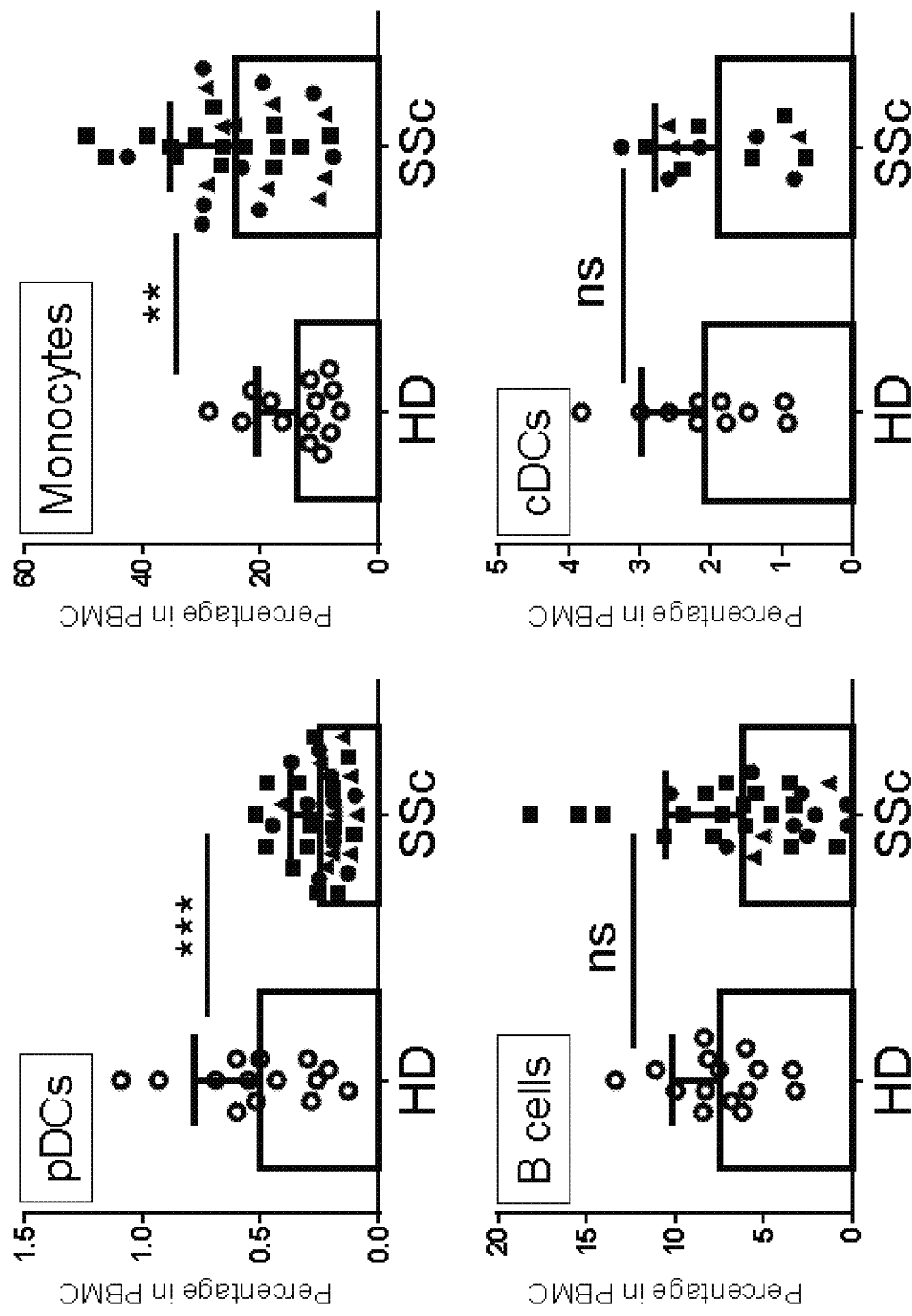
FIG. 1C is a graph of the percentages of pDCs, monocytes, B cells and cDCs within PBMC of either HDs (open circle, N=10-15) or SSc patients (N=14-33) defined as early diffuse (closed circle), late diffuse (closed square) or limited (closed triangle) were quantified by flow cytometry.
Figure 1D:
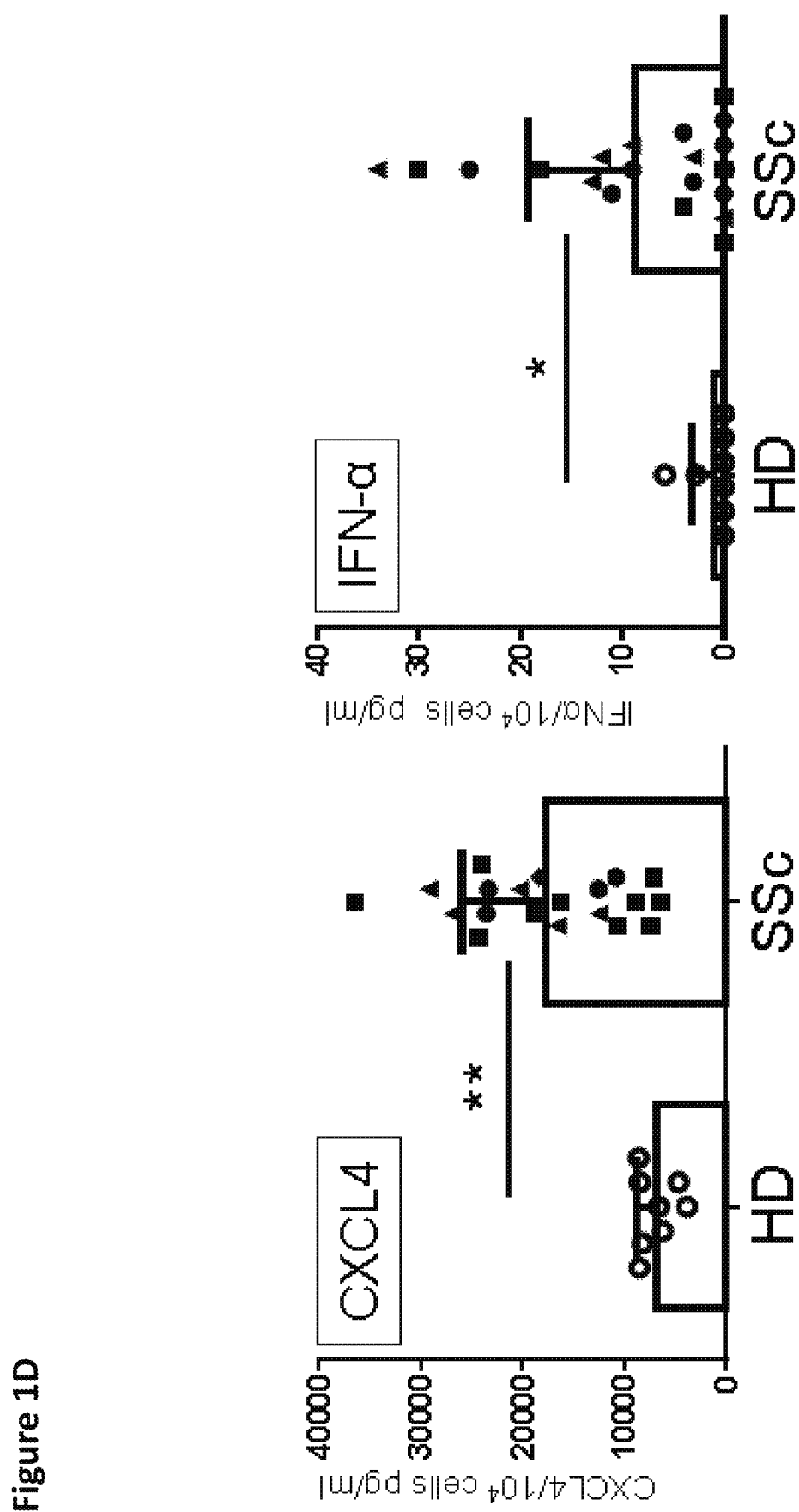
FIG. 1D is a graph of CXCL4 and IFN-α as quantified by ELISA from purified pDCs from HDs (N=8) or SSc patients (N=20) cultured for 24 hours without stimuli. Results were normalized to 10,000 cells to account for the differences between donors in the number of cells put in culture.
Figure 1E:
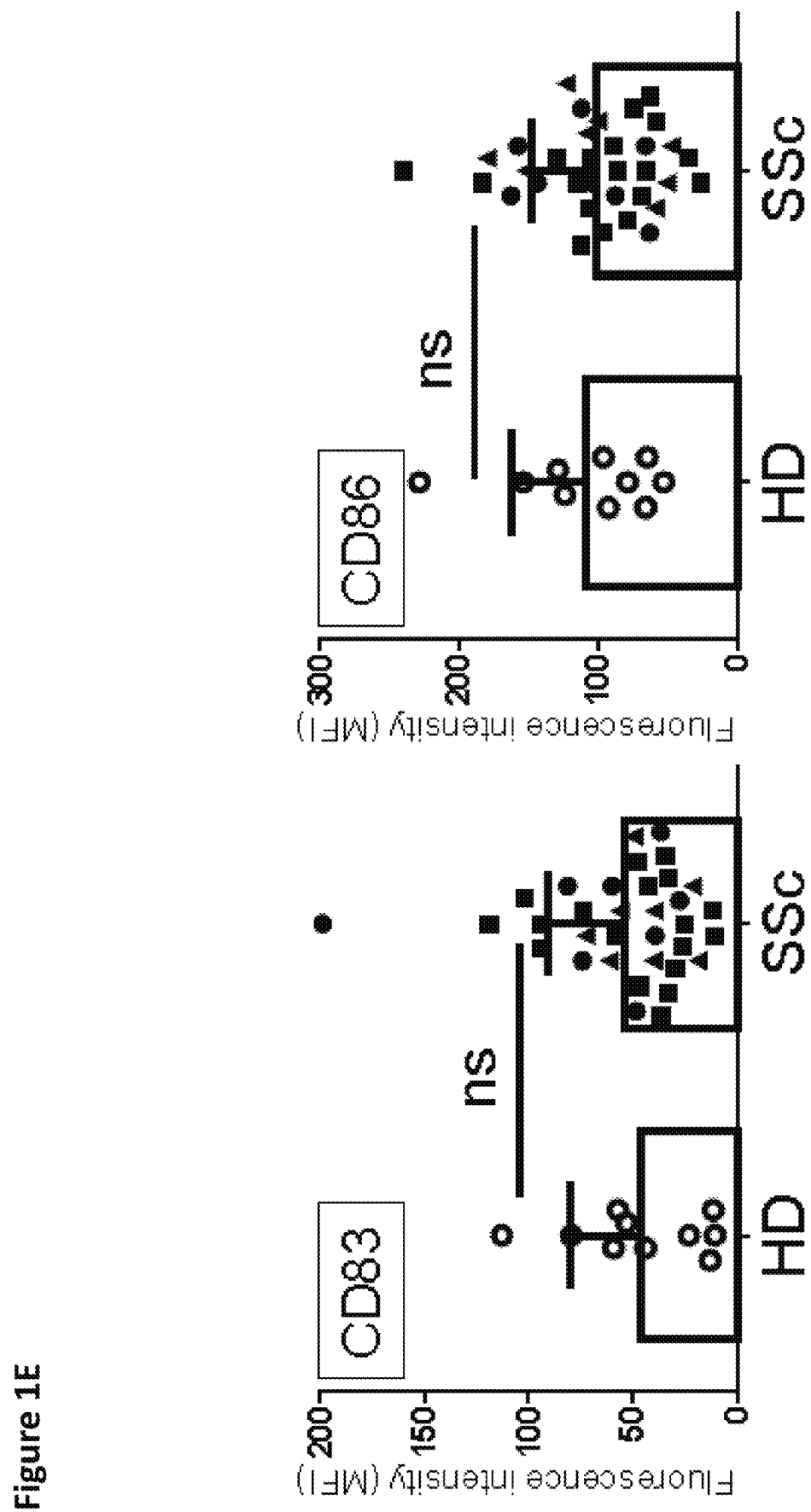
FIG. 1E is a graph of the mean fluorescence intensity of the co-stimulatory molecules CD83 and CD86 expressed on pDCs (N=10 for HDs, N=33 for SSc patients) as quantified by flow cytometry. Statistical significance was evaluated using a Mann-Whitney U-test and *p<0.05; p<0.01; *p<0.001.

Activated pDCs have been observed to accumulate in the skin of SSc patients (van Bon et al. 2014) in a similar way to what has been observed in skin lesions in diseases characterized by interface dermatitis (Wenzel and Tuting 2008). The presence of pDCs in skin biopsies of SSc patients was observed but not in biopsies of HD (FIG. 1A), highlighting the role played by these cells in patients and confirming the importance of better understanding what controls their activation in the skin of patients. Similarly to what has been shown in lupus patients (Cederblad et al. 1998; Blanco et al. 2001), a significant (p<0.001) decrease in the number of pDCs circulating in the blood of SSc patients was found as compared to HDs (FIGS. 1B and 1C). This decrease was an indicator of in vivo activation of pDCs and their migration into peripheral lymphoid tissues and to the skin (FIG. 1A). No significant difference was observed in total B cells or conventional DCs (cDCs), while monocytes were increased (FIGS. 1B and 1C). Secondly, when cultured in the absence of additional stimuli, purified pDCs from the blood of SSc patients spontaneously secreted IFN-α but also CXCL4, a chemokine recently identified as a biomarker for the disease (van Bon et al. 2014) (FIG. 1D). In some cases, the quantity of IFN was below the detection level of the assay. The kinetics of IFN-α production by pDCs was rapid which may explain the low levels of IFN, as the cell preparation likely contained a mix of cells recently activated along with cells activated more than 24 hours previously. There was no difference in the secretion of any other chemokine analyzed, namely CCL3, CCL4 and CCL5, between SSc and HDs pDCs nor was secretion of TNF, IFN-γ or IL-12p40 observed from either SSc or HDs pDCs. It has been previously shown that pDCs, when activated, can upregulate costimulatory molecules such as CD80, CD83 or CD86 and then mature into antigen presenting cells (APCs) (Duramad et al. 2003; Guiducci et al. 2006). It was observed here that pDCs from SSc patients did not express these co-stimulatory molecules (FIG. 1E) demonstrating that the chronic activation of pDCs in these patients likely involved the IFN pathway without the involvement of NF-kB-dependent signals which are required for the induction of these costimulation molecules (Guiducci et al. 2006).

Example 3—pDCs from SSc Patients Displayed an Aberrant Expression Profile of TLRs with the Presence of TLR8

The sensing of nucleic acids by TLRs leads to substantial production of IFN-α by pDCs, suggesting that the chronic activation of pDCs in SSc patients may involve TLRs.

Figure 2A:
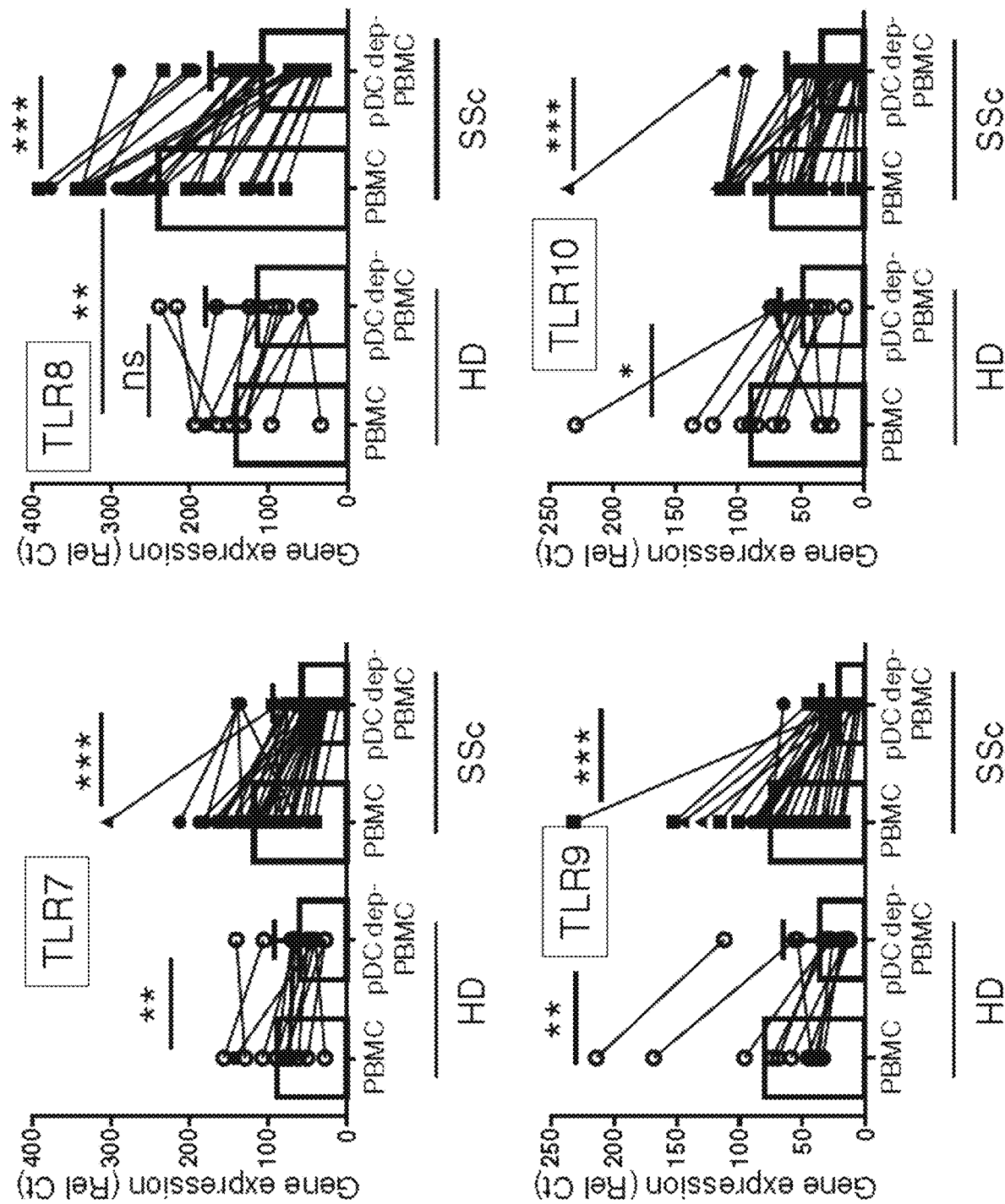
FIG. 2A shows the gene expression levels of TLR7, TLR8, TLR9 and TLR10 quantified in total PBMC or pDC-depleted PBMC prepared from either HDs (n=13) or SSc patients (n=34) by qPCR.

Thus, the mRNA expression levels of the nucleic acid-sensing TLR7, TLR8, and TLR9, as well as TLR10 were quantified on purified pDCs from SSc patients, SLE patients or HDs. Similarly to HDs, pDCs from SSc patients expressed both BDCA2 and BDCA4, and it was confirmed that monocytes from SSc patients did not have an aberrant expression of BDCA4 (data not shown). The expression levels of TLR7, TLR9, and TLR10 were similar in PBMCs prepared from SSc patients or HDs and were equally reduced in pDC-depleted PBMCs, which is expected since these three TLRs are normally expressed on pDCs (FIG. 2A). However, it was observed that TLR8 expression was increased in PBMCs of SSc patients and surprisingly that the levels of expression of TLR8 in patients were normalized to those of HDs when pDCs were depleted from PBMCs (FIG. 2A). In these experiments, monocytes were not impacted by the depletion protocol, which is consistent with their lack of BDCA4 expression (data not shown).

Furthermore, while pDCs isolated from HDs did not express TLR8 as has repeatedly been shown (Guidacci et al. 2013), aberrant expression of TLR8 in pDCs isolated from the blood of SSc patients was observed (FIG. 2D). The presence of TLR8 on pDCs was seen in 25 of the 29 patients tested, including patients with early or late diffuse SSc but also in patients with limited SSc. It was also observed that TLR8 was not expressed on pDCs isolated from lupus patients (FIG. 2D), another disease where pDCs have been involved. Although the gating strategy excluded cell types known to express TLR8, it was confirmed that no markers for non-pDCs cells (in particular neutrophils, that express abundant TLR8) could be observed, which excluded a contribution of contaminating cells to the results. Similar findings were obtained using pDCs from HDs or SLE patients. These data thus suggested that the pDCs from SSc patients do express TLR8, which appears to be a feature of SSc.

Figure 2B:
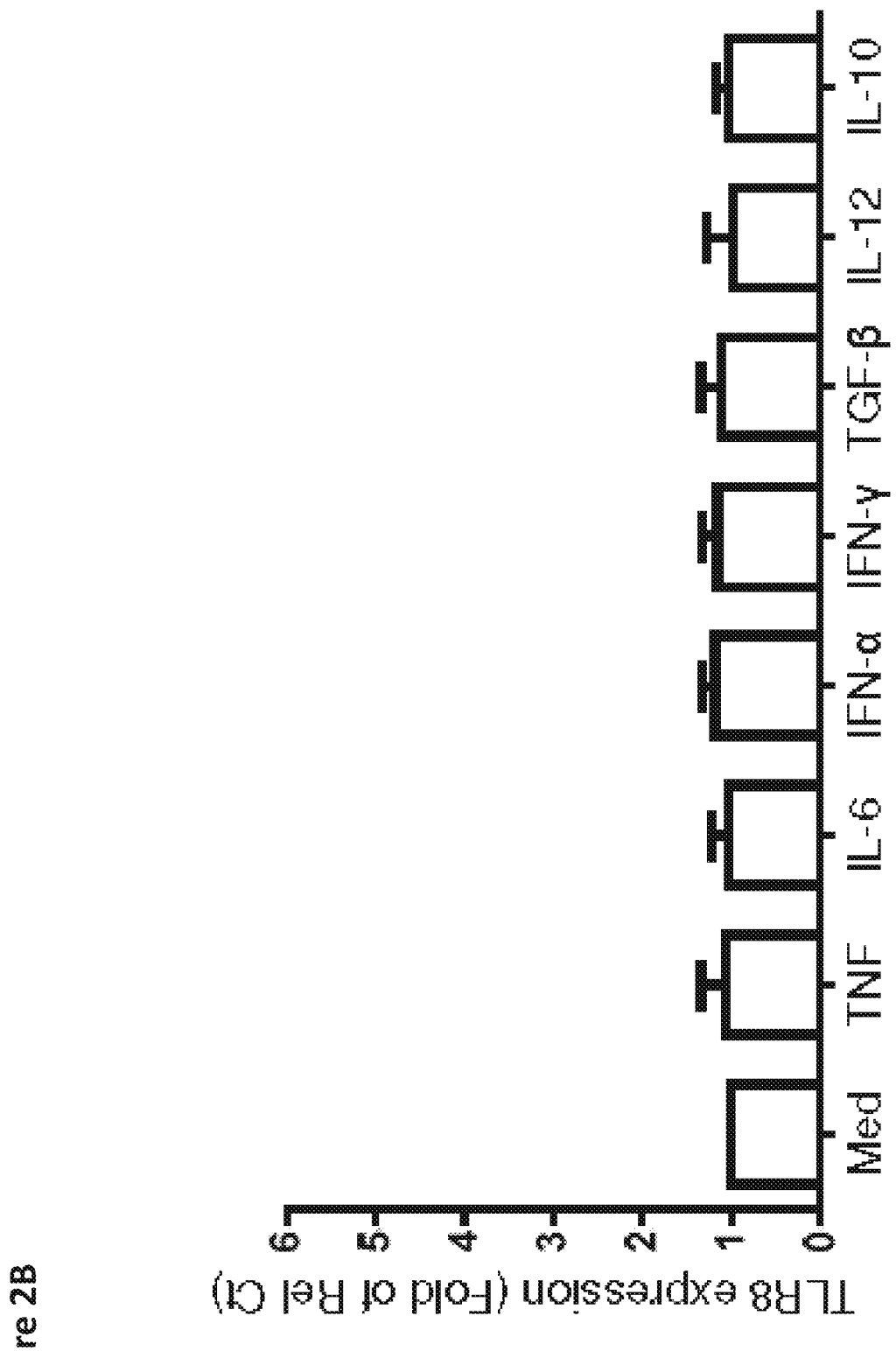
FIG. 2B shows the gene expression levels of TLR8 quantified in purified pDCs from HDs (n=4-6) cultured for 24 hours either alone or in the presence of TNF, IL-6, IFN-α, IFN-γ, TGF-β, IL-12, or IL-10.

Various inflammatory cocktails of cytokines, including IFN-α and IFN-γ (10 ng/ml), IL-12 (100 ng/ml), IL-6 (5 ng/ml), IL-10 (10 ng/ml), TNF (1 ng/ml) or TGF-β (10 ng/ml), were tested to determine what is regulating TLR8 expression on pDCs of SSc patients, but none of these molecules could induce TLR8 on pDCs of HDs (FIG. 2B).

Figure 2C:
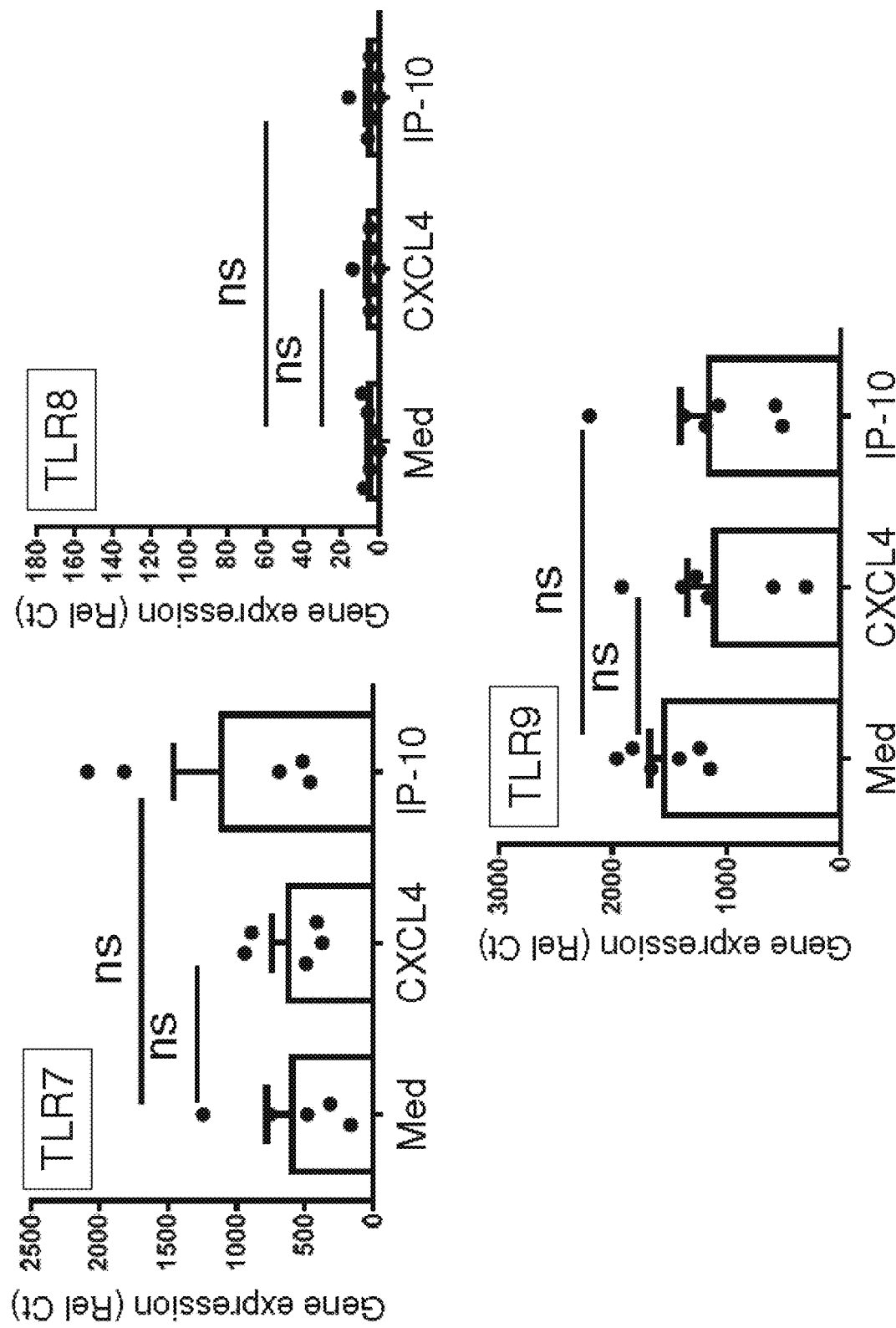
FIG. 2C shows gene expression levels of TLR7, TLR8, and TLR9 quantified in purified pDCs from HDs (n=4-6) cultured for 24 hours either alone or in the presence of CXCL4 or IP-10 analyzed by qPCR.

In particular, CXCL4 or IP-10 (two CXCR3B agonists) (10 µg/ml each) had no impact on TLR8 nor TLR7 and TLR9 expression levels in pDCs (FIG. 2C). Interestingly, this dysregulation of TLR8 expression was not observed in other cell subsets including monocytes, which naturally expressed TLR8 with similar expression between HDs and SSc patients (FIG. 2D). Similar to pDCs, purified B cells from HDs did not express TLR8, and it was observed that TLR8 was not present in B cells from SSc patients (FIG. 2D), suggesting that the dysregulation of TLR8 was a distinct feature of pDCs of SSc patients. TLR7 and TLR10 expression was similar in SSc and HD pDCs whereas TLR9 expression was slightly decreased in SSc pDCs, as is often the case when pDCs are activated (FIG. 2E). Of note, expression of TLR7 and TLR9 was significantly greater ($p<0.01$ and $p<0.001$, respectively) in pDCs of SLE patients as compared to SSc patients (FIG. 2E). No difference was observed in B cells or monocytes for TLR7, 9 or 10 (FIGS. 2F and 2G). These data suggested that in addition to being chronically activated, pDCs of SSc patients have an abnormal profile of TLRs characterized by the expression of TLR8.

Figure 3A:
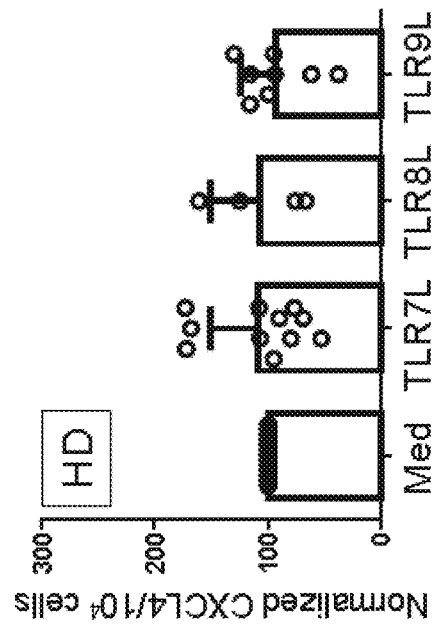
FIG. 3A shows the gene expression levels of CXCL4 quantified by qPCR in total PBMC or pDC-depleted PBMC prepared from either HDs (n=6) or SSc patients (n=23). Statistical significance was evaluated using the unpaired Mann-Whitney test between HDs and SSc PBMC and with a paired t-test between PBMC and pDC-depleted PBMC from SSc patients.

Example 4—TLR8 Signaling in pDCs of SSc Patients Induced CXCL4 Whereas TLR7 and TLR9 Did Not The chemokine CXCL4 can be secreted by many cells within the PBMCs including pDCs (van Bon et al. 2014), and was more abundant in PBMCs from SSc patients as compared to HDs (FIG. 3A). However, when pDCs were depleted from PBMCs, the increased secretion of CXCL4 observed in SSc PBMCs was normalized to HDs PBMC levels (FIG. 3A) demonstrating that the excess of CXCL4 observed in PBMCs of SSc patients is solely due to the activation of pDCs and not to the contribution of other cell types.

Figure 3B:
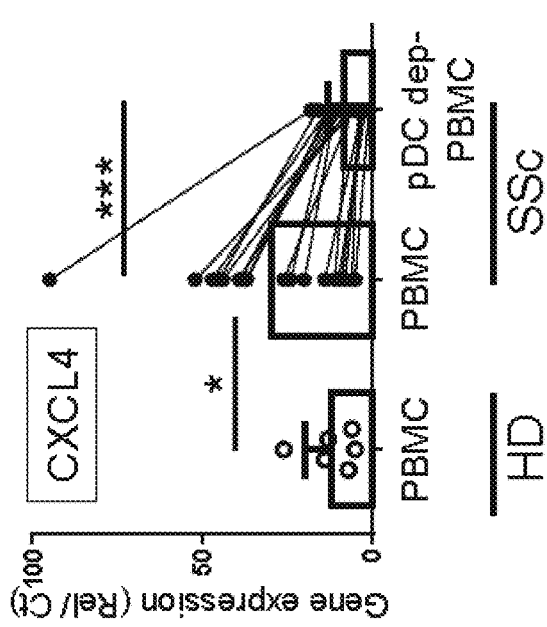
FIG. 3B shows CXCL4 in the supernatants measured by ELISA from purified pDCs from HDs (n=4-11) cultured for 24 hours either with media alone as a control, or in the presence of a TLR7 agonist, a TLR8 agonist or a TLR9 agonist. Results were normalized to the value of media alone and represented as a mean±SEM.
Figure 3C:
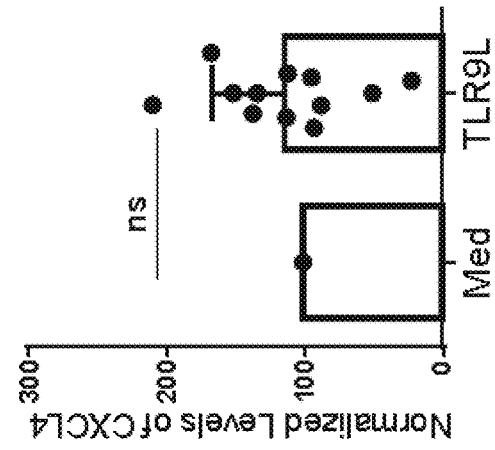
FIG. 3C is a graph showing CXCL4 production analyzed by ELISA in pDCs purified from SSc patients (n=15 and 12 respectively) cultured for 24 hours either in media alone or with ORN-8L, a TLR8 agonist. Results were normalized to control and represented as a mean±SEM.
Figure 3D:
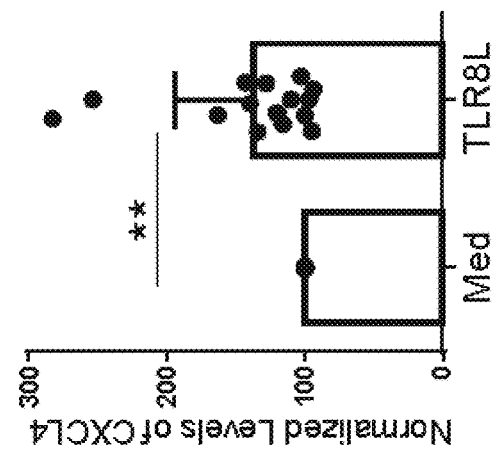
FIG. 3D is a graph showing CXCL4 production analyzed by ELISA in pDCs purified from SSc patients (n=15 and 12 respectively) cultured for 24 hours either in media alone or with CpG-C274, a TLR9 agonist. Results were normalized to control and represented as a mean±SEM.
Figure 3E:
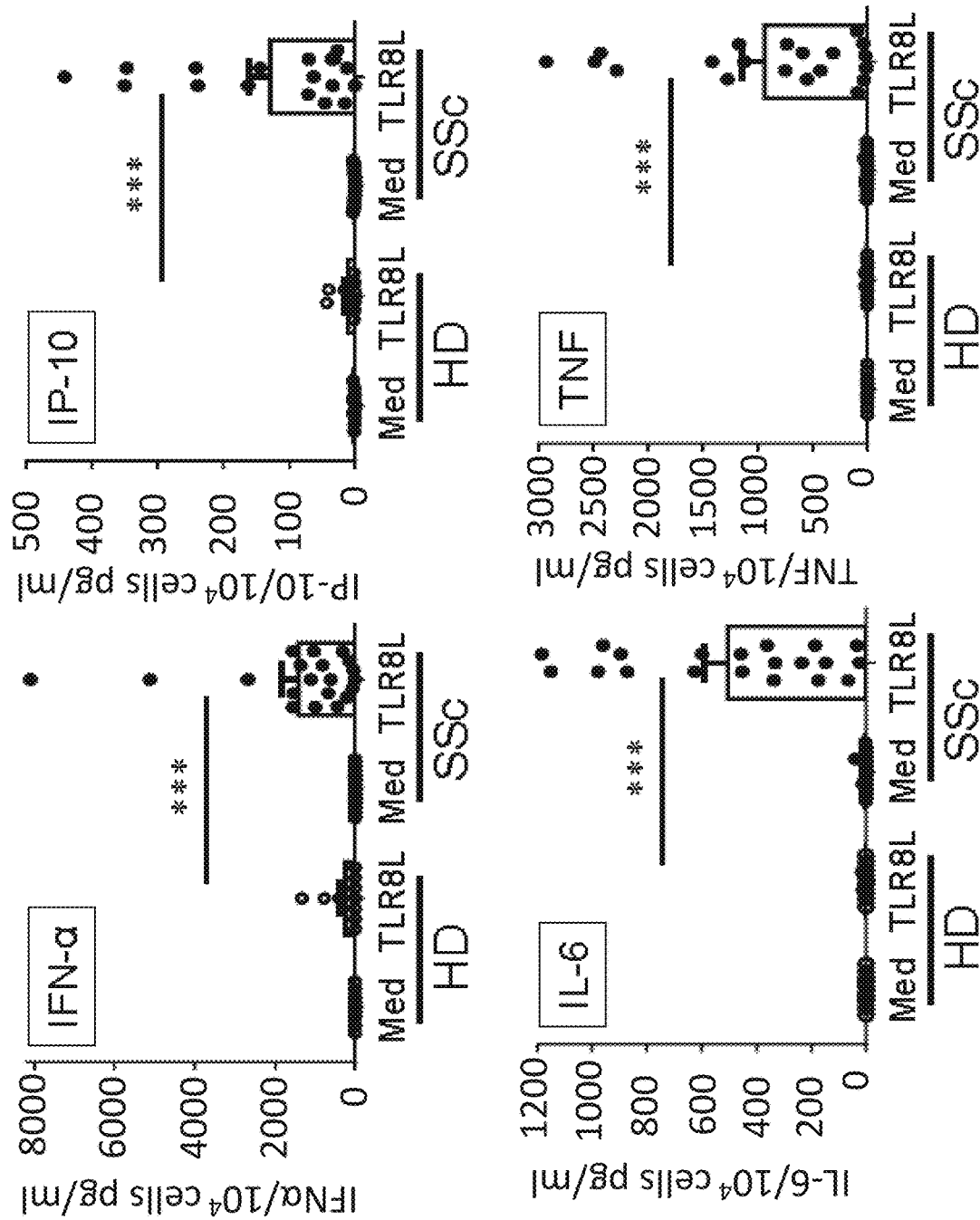
FIG. 3E is a graph showing the number of HD (n=10) and SSc pDCs (n=20) stimulated with ORN-8L for 24 hours and supernatants collected for measurement of IFN-α, IP-10, IL-6, and TNF by multiplex-bead assay. Results were normalized to 10,000 cells.
Figure 3F:
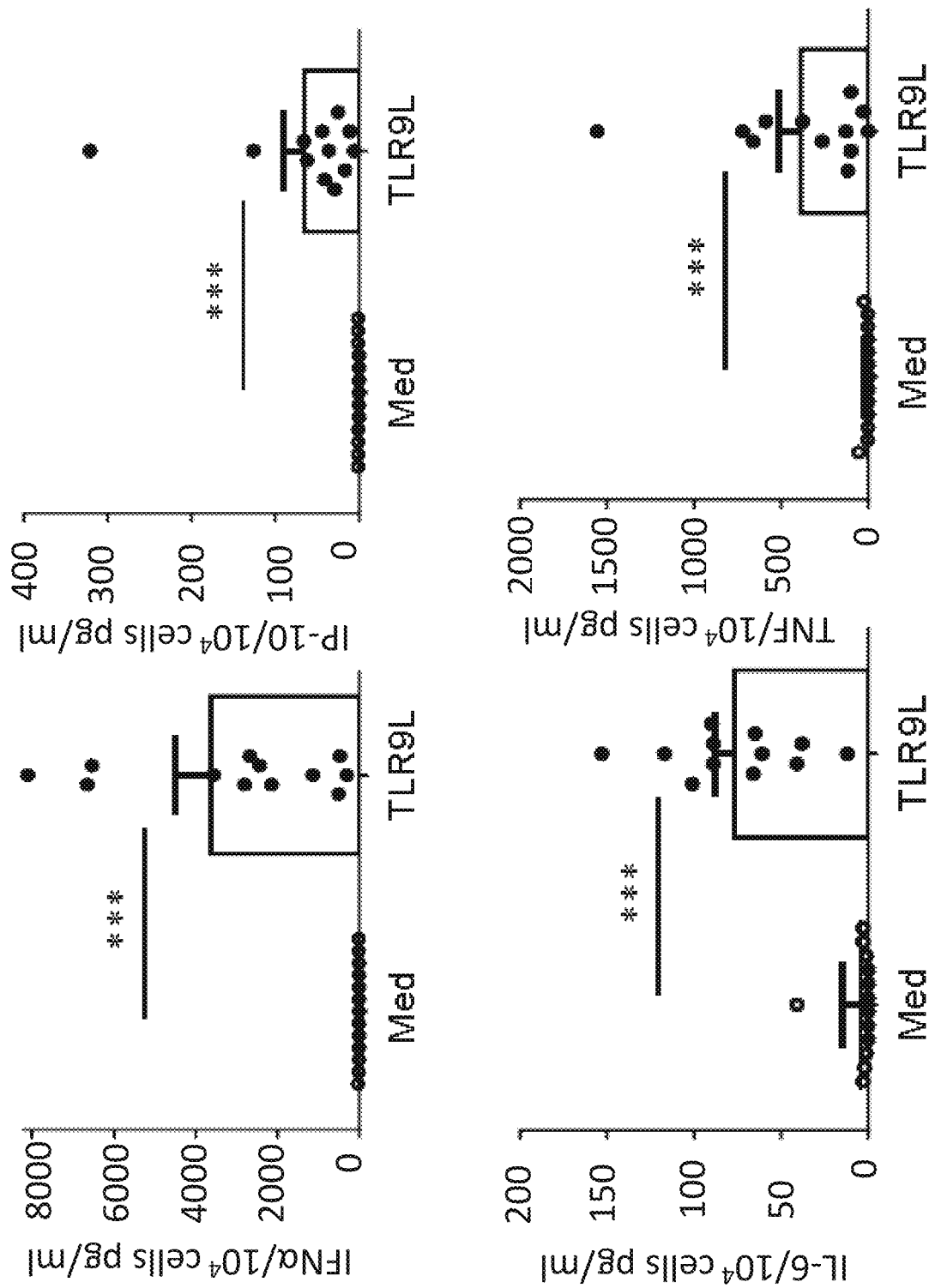
FIG. 3F is a graph showing the number of purified pDCs from SSc patients (n=12) cultured either with media alone or in the presence of a TLR9 agonist for 24 hours and supernatants collected for measurement of IFN-α, IP-10, IL-6, and TNF by multiplex-bead assay. Results were normalized to 10,000 cells. All results are represented as a mean±SEM. For FIG. 3B-3E, statistical significance was evaluated using a Mann-Whitney U-test and *p<0.05; p<0.01; *p<0.001.

Culturing pDCs purified from HDs with agonists of either TLR7 or TLR9 did not lead to CXCL4 production (FIG. 3B). In contrast, it was observed that TLR8 but not TLR9 signaling could further induce CXCL4 secretion by pDCs from SSc patients (FIGS. 3C and 3D). The triggering of TLR8 in pDCs of SSc patients also induced the production of IFN-α, IP-10, IL-6 and TNF while it had no effect on HDs pDCs (FIG. 3E). Although TLR9 signaling did not induce CXCL4, the response by pDCs from SSc patients was otherwise normal with the induction of IFN-α, IP-10, IL-6 and TNF (FIG. 3F).

Taken altogether, these data demonstrated that the aberrant expression of TLR8 on the pDCs of these patients can change the nature of the response of those cells to nucleic acids and can induce the secretion of CXCL4. This is a unique situation where the atypical expression of a TLR on a cell type can impact the nature of its response, with a clear association with a disease.

Example 5—CXCL4 Exacerbated the TLR-Mediated IFN-α Response in SSc pDCs and its Production is Under the Control of the PI3Kδ Pathway Very little is known on how CXCL4 can impact immune function and whether this chemokine has any effect on the direct induction of fibrosis in patients. In contrast, the contribution of type I IFN and pDCs has been well described in many autoimmune diseases and although its effect on fibrosis is more controversial, the presence of an IFN-related gene signature has been described in SSc patients (Rice et al. 2015; Tan et al. 2006; York et al. 2007). This raises the question as to whether the impact of CXCL4 in SSc patients is solely to potentiate the pathogenic IFN response or to promote an inflammatory response independently of the IFN pathway.

Figures 4A, 4B:
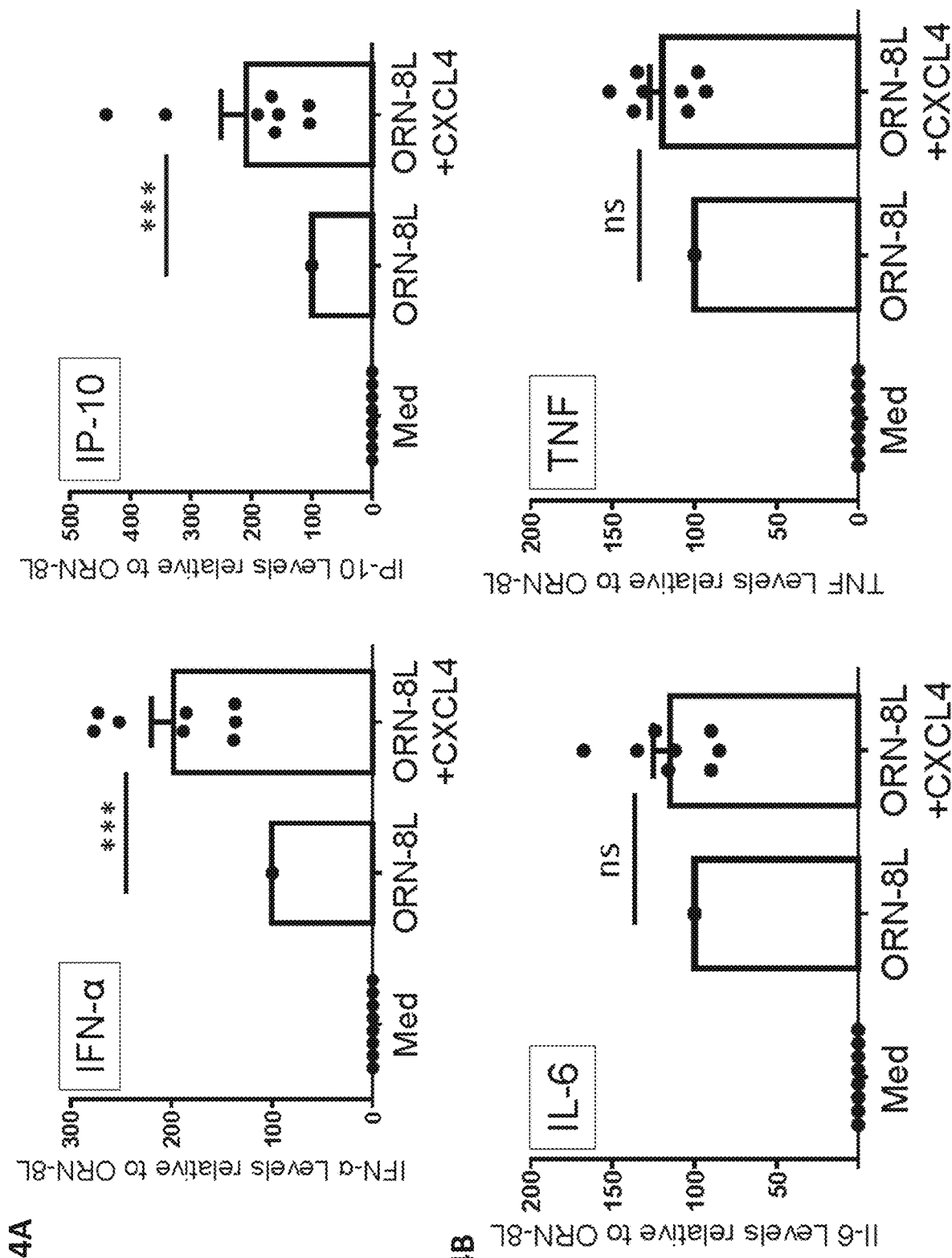
FIG. 4A are graphs showing IFN-α and IP-10 levels quantified in the supernatants by ELISA of purified pDCs from SSc patients (n=8) cultured in media alone (control), with ORN-8L, or with ORN-8L and CXCL4 for 24 hours. Values were normalized to ORN-8L alone and represented as a mean±SEM.
FIG. 4B are graphs showing IL-6 and TNF levels quantified in the supernatants by ELISA of purified pDCs from SSc patients (n=8) cultured in media alone (control), with ORN-8L, or with ORN-8L and CXCL4 for 24 hours. Values were normalized to ORN-8L alone and represented as a mean±SEM.

When purified pDCs from HDs or SSc patients were cultured with CXCL4 alone (10 µg/ml), there was no effect on IFN production. However, it was observed that adding CXCL4 significantly increased ($p<0.001$) the production of IFN-α and of IP-10 in response to TLR8 (stimulated by ORN-8L at 200 µg/ml) in the form by purified pDCs from SSc patients (FIG. 4A) while it had no effect on IL-6 or TNF production (FIG. 4B). This observation indicated that in addition to its potential direct effect on other immune functions, CXCL4 has a critical role in potentiating the TLR-induced IFN production in SSc patients.

Although purified pDCs from SSc patients can spontaneously secrete IFN-α and CXCL4 (FIG. 1D), there was not observation of an increase of co-stimulatory molecules on these cells (FIG. 1E), suggesting that the chronic activation of pDCs in these patients likely involves the transcription factor IRF7 (Guidacci et al. 2008).

It has been previously shown that IRF7 translocation to the nucleus of pDCs and subsequent production of IFN-α are under the strict control of PI3Kδ (Guidacci et al. 2008) and thus it was decided to test the involvement of PI3Kδ in controlling pDC activation in SSc patients. When cultured in the presence of the specific inhibitor of PI3Kδ CAL-101 (at 10 µM), the secretion of both CXCL4 and IFN-α was inhibited and normalized to that of HDs pDCs (FIGS. 4C and 4D). CAL-101 was used at a concentration that can effectively block TLR9-induced IFN production by pDCs from HDs without impacting IL-6 production or cell viability. Blocking PI3Kδ had no effect on the secretion of IL-6 by pDCs of SSc patients (FIG. 4E) which indicated inhibiting PI3Kδ could block the chronic activation of pDCs in SSc patients without globally affecting the ability of these cells to be activated in response to pathogens.

Example 6—CXCL4 Potentiated TLR9-Induced IFN-α but had Minimal Effect on TLR7-Mediated Activation of pDCs Purified from Either HDs or SSc Patients The effect of CXCL4 on TLR7- and TLR9-induced response by human pDCs was measured from both HDs and SSc patients. These two TLRs can induce high levels of IFN-α by human pDCs, and recent findings suggested that TLR9-induced IFN-α production was reduced by blocking CXCL4 (van Bon et al. 2014).

Figure 5E:
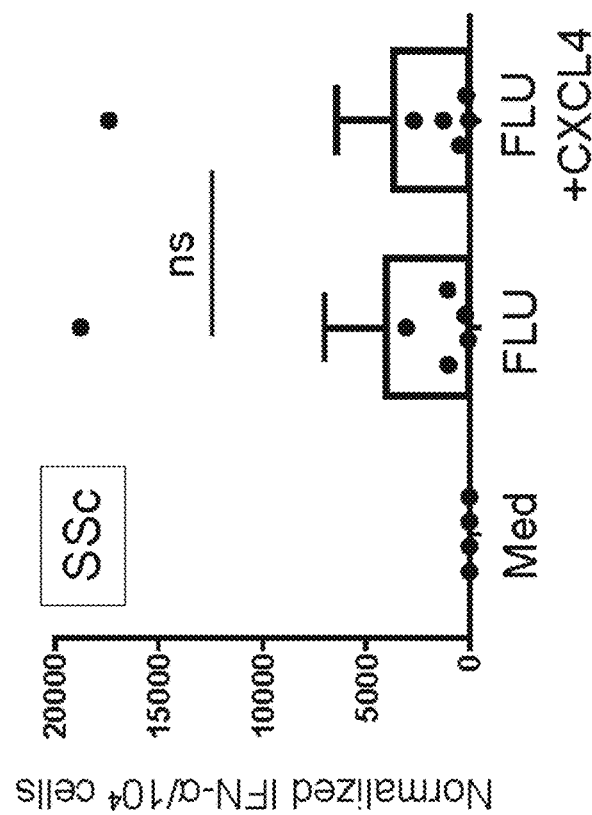
FIG. 5E shows IFN-α quantified in the supernatants by ELISA in purified pDCs from SSc patients cultured in media alone (control), or with a TLR7 agonist FLU or with FLU and CXCL4 for 24 hours. (N=6-18 as indicated). Values were normalized to 10,000 cells and all results are represented as a mean±SEM and statistical significance evaluated using a Mann-Whitney U-test and *p<0.05; p<0.01; *p<0.001.
Figure 5D:
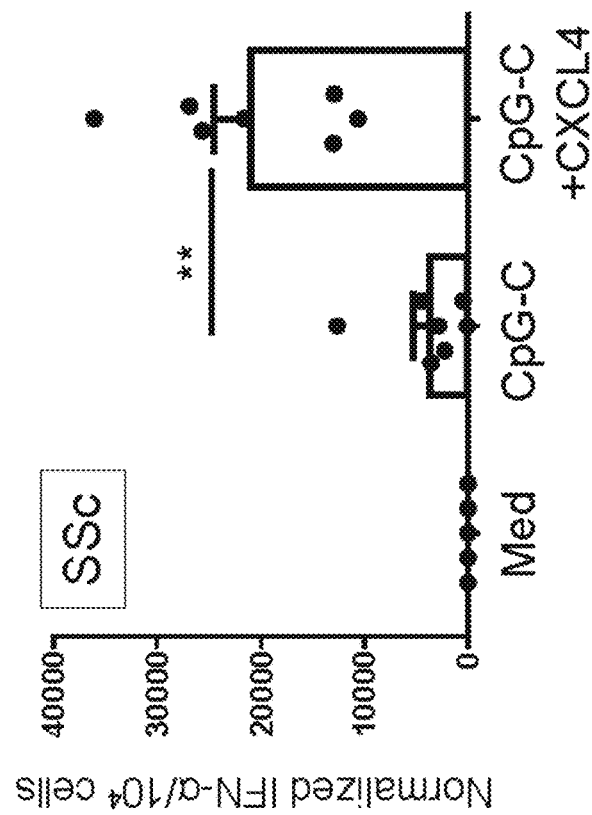
FIG. 5D shows IFN-α quantified in the supernatants by ELISA in purified pDCs from SSc patients cultured in media alone (control), or with either a CpG-C, a TLR9 agonist or with CpG-C and CXCL4.

In order to evaluate the impact of CXCL4 on TLR-induced pDCs response, agonists of TLR7 and TLR9 were used at suboptimal doses and used both a CpG-C (0.1 µM) and a CpG-B ODN (0.25 µM). It was observed that CXCL4 (10 µg/ml) drastically impacted the TLR9 response irrespective of the CpG used (FIGS. 5A and 5B) with little to no effect on the TLR7 response (FIG. 5C). This effect was similar both in HDs (FIGS. 5A-5C) and SSc patients (FIGS. 5D and 5E) which is consistent with the fact that CXCR3B is expressed at similar level in purified pDCs of HDs and SSc patients, and CXCL4 itself did not induce IFN-α. These data thus suggest that the effect of CXCL4 was not restricted to TLR8 in patients and can impact TLR9 as well.

Example 7—pDCs are Required for the Establishment and Maintenance of Skin Fibrosis in a Mouse Model of Scleroderma The display of an IFN-signature in SSc patients, the presence of pDCs in the skin of localized scleroderma (morphea) and of SSc patients (van Bon et al. 2014) and the data in the Example showing that pDCs were chronically activated in SSc patients suggest that pDCs may participate in the pathogenesis of the disease. However, whether pDCs directly contributes to the fibrosis in the skin is unclear.

To address this question, skin fibrosis was induced in C57/BL6 mice by injection of bleomycin (BLM), a cancer drug that has long been known to cause fibrosis. In mice, BLM treatment constitutes a well characterized mouse model for SSc and can induce skin fibrosis with a prevalence of almost 100% (Yamamoto et al. 1999; Batteux et al. 2011), leading to increased skin thickness and loss of the sub-cutaneous fat in favor of sclerotic tissue (Chia et al. 2016). The fibrotic outcome of BLM treatment encompasses collagen deposition in the skin and the induction of alpha-smooth muscle actin ($\alpha$-SMA)-positive stromal cells.

It was first confirmed that pDCs infiltrated the skin in this model after 4 weeks of BLM injection by measuring the presence of Siglec-H+ cells in the skin (FIG. 6A). The immunohistochemistry staining was confirmed using in-situ RNA hybridization for the siglech transcript in the skin of PBS- or BLM-treated mice (data not shown). To evaluate the direct contribution of pDCs in skin fibrosis, these cells were depleted using CLEC4C-DTR transgenic mice by injection of Diphteria Toxin (DT) starting 24 hours before the first BLM injection and continuing through the entire experiment. As previously described (Rowland et al. 2014), DT injection in CLEC4C-DTR mice was very efficient in specifically deleting pDCs) and does not impact other cell types in mice, and a significant reduction ($p<0.01$) of pDCs infiltration was observed in the skin of the mice (FIG. 6A). The loss of pDCs led to a significant reduction ($p<0.001$) in the skin thickness of BLM-injected mice with an almost preserved sub-cutaneous fat (FIG. 6B) and a normal content of collagen in the skin (FIG. 6C).

Figure 6E:
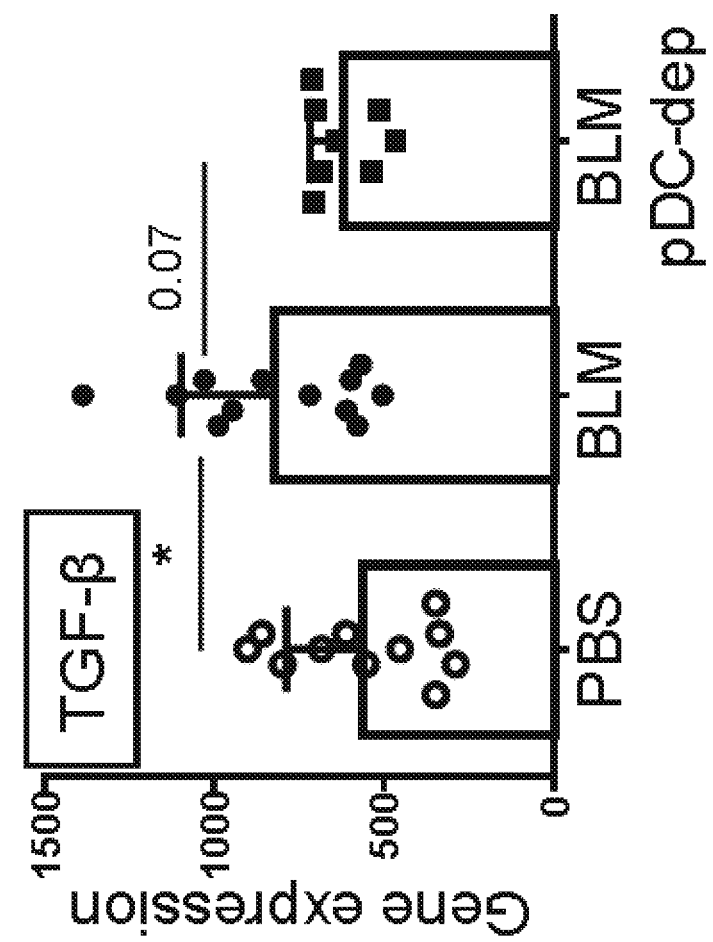
FIG. 6E is a graph of the gene expression of TGF-B in the skin of the same mice using Nanostring technology.

Dermal myofibroblasts have the capacity to synthesize and deposit extracellular matrix components (Huang et al. 2016) and can be identified by expression of $\alpha$-SMA. The depletion of pDCs resulted in a significantly decreased number of these cells ($p<0.001$) as compared to pDC-sufficient mice (FIG. 6D). The expression of TGF-$\beta$, a well-known marker of fibrosis for its impact on the synthesis and deposition of extracellular matrix by fibroblasts, was also reduced in pDC-depleted mice (FIG. 6E).

Figure 6F:
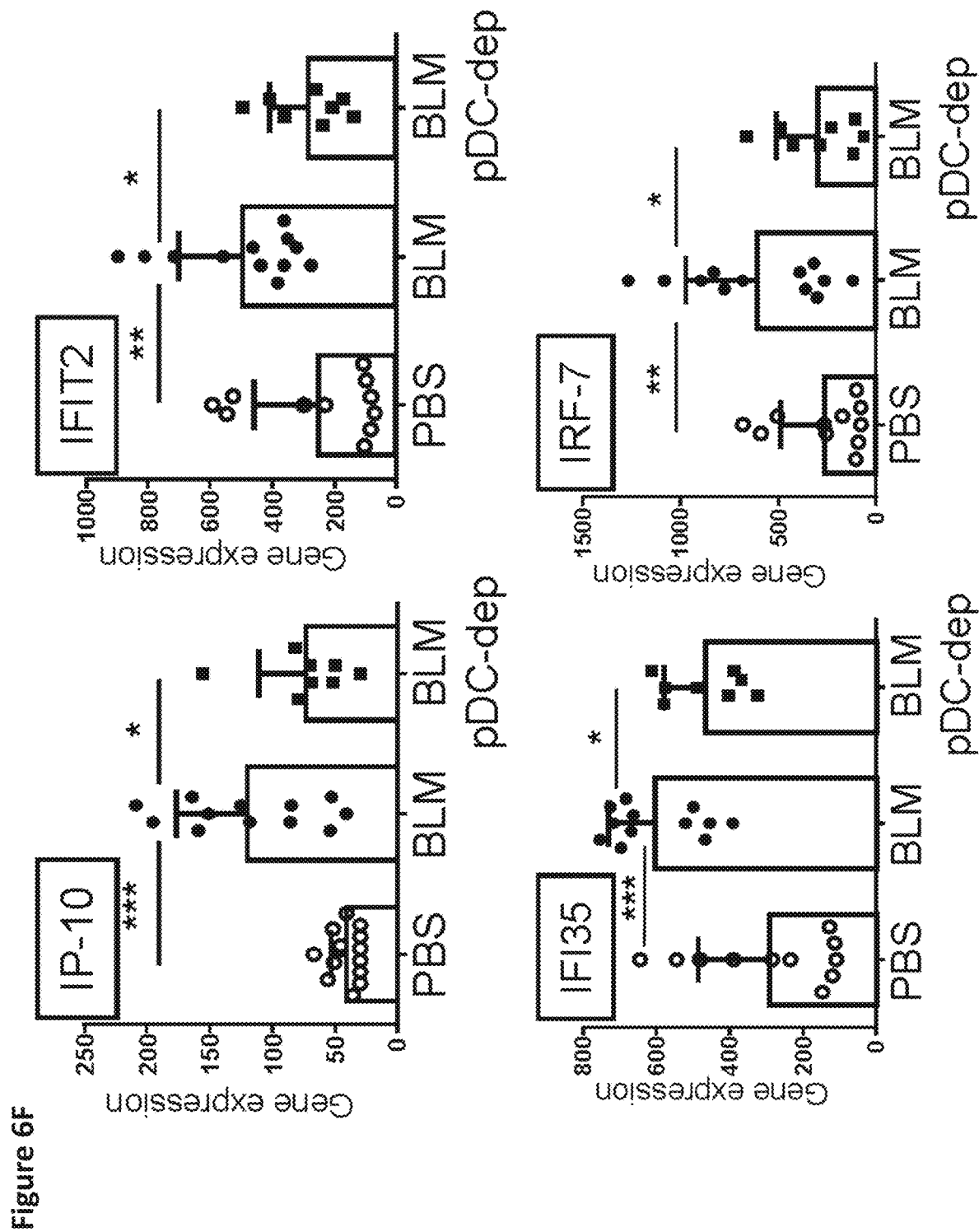
FIG. 6F are graphs of the relative gene expression in the skin of the same mice of the indicated genes using the NanoString technology.
Figure 6G:
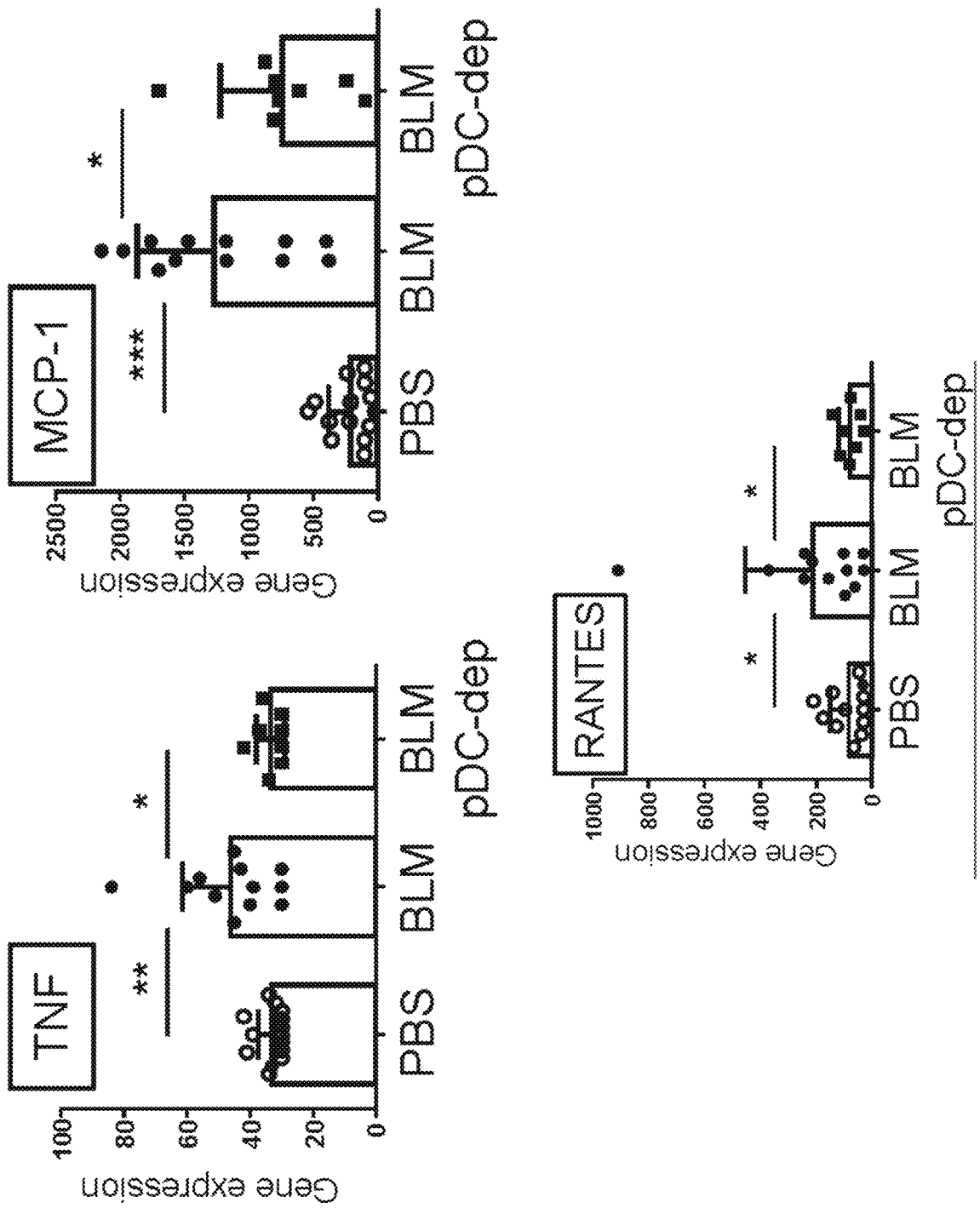
FIG. 6G are graphs of the relative gene expression in the skin of the same mice of the indicated genes using the NanoString technology. All values represent mean±SEM; n=6-14 mice for each group. Data are cumulative of three independent experiments and statistical significance was evaluated using a Mann-Whitney U-test and *p<0.05; p<0.01; *p<0.001.

It has also been shown that pDCs can induce a strong IFN response in the skin following injury (Guidacci et al. 2010) and the same was observed in this fibrosis model, with the presence of multiple IFN-regulated genes in BLM-treated animals, genes that were not expressed in pDC-depleted BLM-treated animals (FIG. 6F). It was also observed that a blockade of pro-inflammatory cytokines/chemokines such as TNF and MCP-1 (FIG. 6G) that have been associated with fibrosis (Koca et al. 2008; Yamamoto and Nishioka 2003) in pDC-depleted mice, which was accompanied by a reduction in the overall immune cell infiltration in the skin.

These data demonstrated that the pDC is a critical cell type directly involved in skin fibrosis as its depletion impacts both the inflammatory response that is induced by BLM but also the actual fibrotic outcome.

The role of pDCs in the maintenance of the disease was evaluated by depleting pDCs after three weeks of BLM treatment followed by the continuation of the BLM injections for an extra two weeks. After three weeks of BLM treatment, an increase of the skin thickness in the mice and increased in the infiltration of pDCs was observed, and this was even more apparent after 5 weeks (FIGS. 7A and 7B). When pDCs were depleted at 3 weeks in mice that had already established disease, at 5 weeks a reduction of the skin thickness was observed as compared to pDC-competent mice. Furthermore, mice that received BLM for 5 weeks with pDCs depleted at 3 weeks had reduced disease even compared to the mice treated with BLM for just 3 weeks (FIG. 7A). This suggested that pDCs are critical for the maintenance of fibrosis in the skin and that their depletion leads to reversion of disease.

Using in situ RNA hybridization for the cxcl4 transcript, the presence of pDCs in the skin correlated with the presence of CXCL4 was shown (FIG. 7C), which links both pDCs and CXCL4 to the promotion of skin fibrosis.

Example 8—TLR8 Exacerbated Disease in the Bleomycin-Induced Fibrosis Model

Figure 8A:
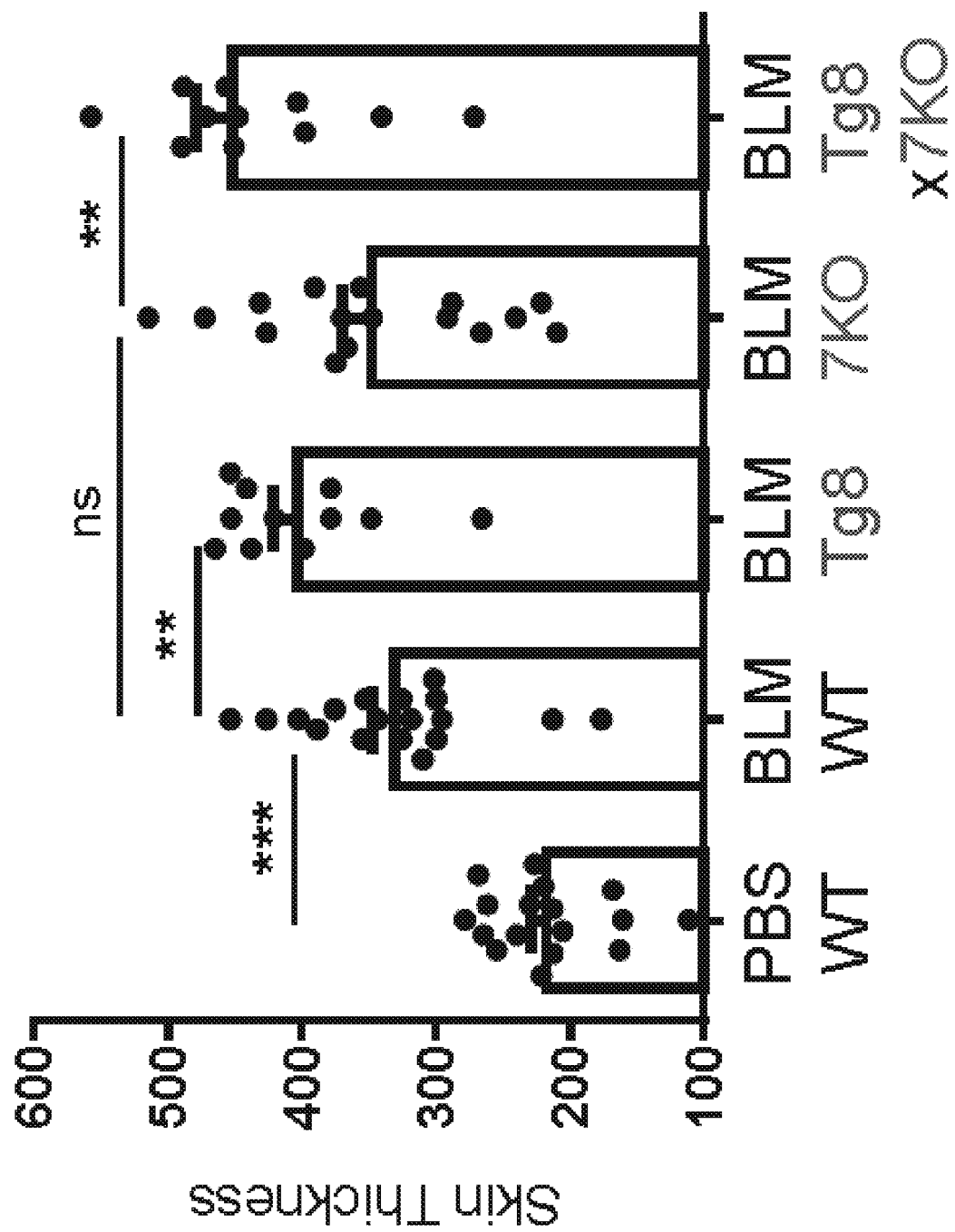
FIG. 8A is a graph of the average of skin thickness of WT mice injected with PBS, or WT mice, Tg8 mice, TLR7KO mice or Tg8×TLR7KO mice injected with BLM (n=11-18/group) as determined by images of Trichrome Masson-stained skin sections at a magnification of ×10.

It is shown herein that the aberrant expression of TLR8 in SSc pDCs led to the production of both CXCL4 and IFN-$\alpha$, suggesting that this receptor has a key role in the disease. In order to better understand whether TLR8 can promote fibrosis in a relevant in vivo model, skin fibrosis was induced in mice that carry the human TLR8 gene (Guidacci et al. 2013). These mice, called huTLR8Tg or Tg8, have a single copy of the huTLR8 gene under the control of human TLR8 genomic regulatory regions, and TLR8 cellular distribution is similar to the human situation. In addition, the respective contribution of TLR7 and TLR8 to disease has been evaluated, as both receptors recognize RNA and seem to regulate each other's response (Guidacci et al. 2013; Demaria et al. 2010). Genetically modified mice were used to perform BLM experiments using huTLR8Tg (have both functional TLR8 and TLR7), huTLR8Tg×TLR7ko (have functional TLR8 but no TLR7), TLR7ko (deficient for both TLR7 and TLR8) and C57/BL6 mice which were de facto TLR8-deficient but have TLR7. Upon BLM treatment, aggravated fibrosis and an increase of skin thickness in huTLR8Tg mice was observed over WT mice (FIG. 8A). In addition, the infiltration of pDCs present in BLM-treated B6 mice was significantly increased in the TLR8Tg mice (FIG. 8B) and did not require the presence of TLR7. The distribution of pDCs in the skin seemed altered in Tg8 mice with cells present in all the skin layers. Mice deficient for TLR7 were not protected from BLM induced fibrosis (FIG. 8A) and huTLR8Tg×TLR7ko mice also showed exacerbated response to BLM as compared to WT or TLR7ko mice (FIG. 8A). Furthermore, there was no significant differences ($p<0.01$) seen in disease between the huTLR8Tg and huTLR8Tg×TLR7ko mice, pointing to a dominant role of TLR8 in this disease (FIG. 8A). However, some of the inflammation observed in the skin could be partially attributed to TLR7.

Figure 8B:
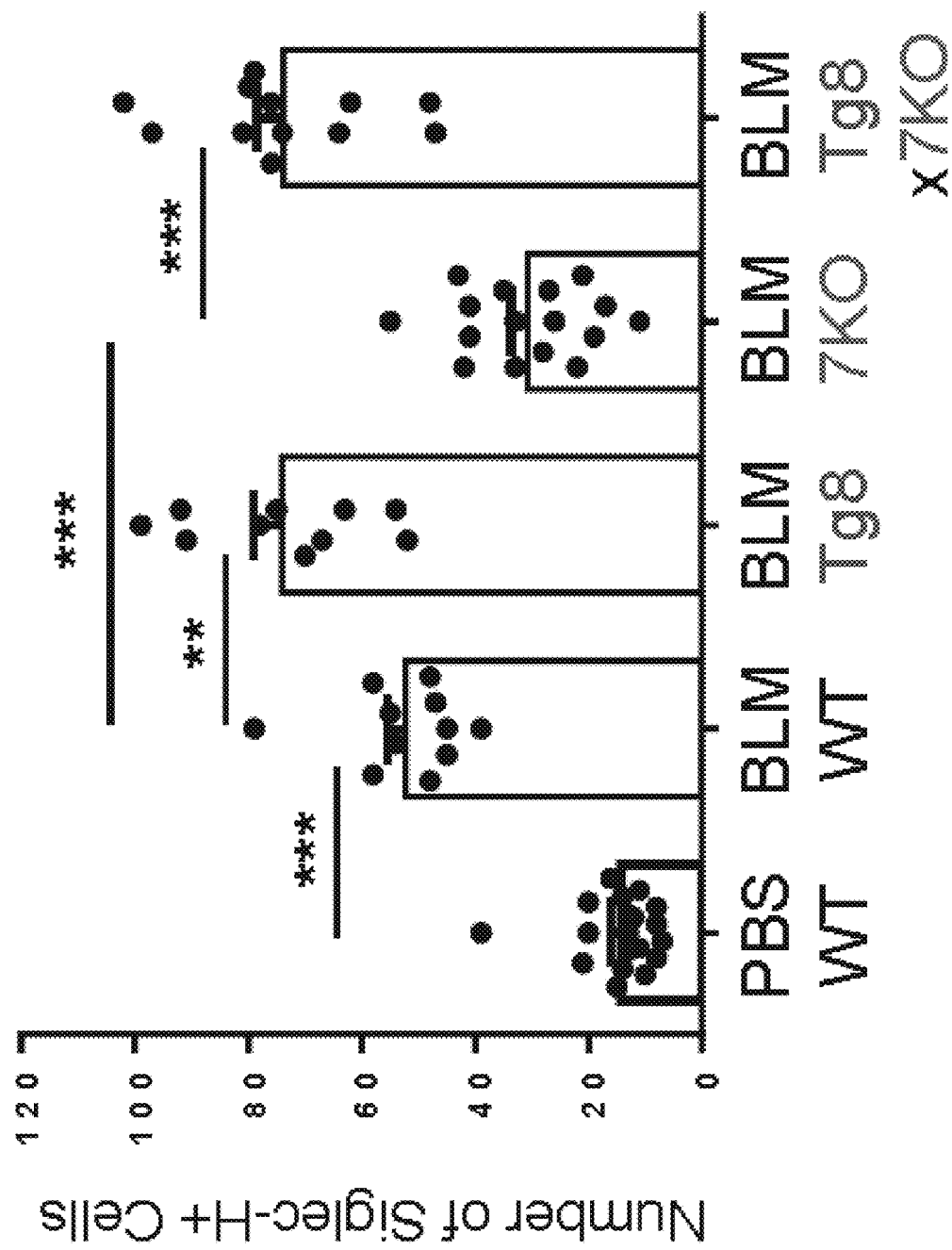
FIG. 8B are histograms that represent numbers of Siglec-H$^+$ cells in the skin of WT mice injected with PBS or with BLM and of Tg8 mice, TLR7KO mice and Tg8×TLR7KO mice injected with BLM and are cumulative of at least 10 mice from 3 independent experiments
Figure 8C:
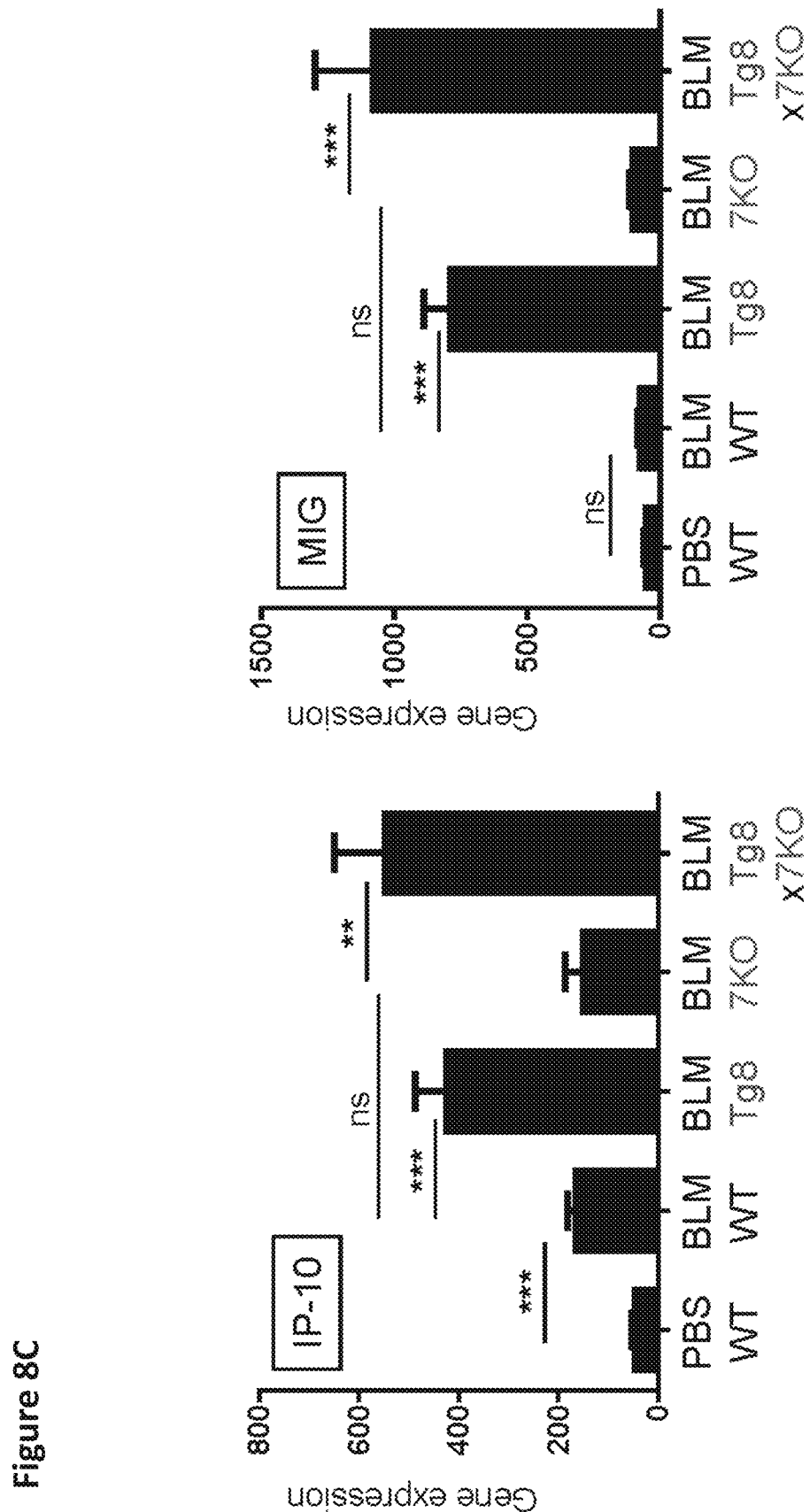
FIG. 8C is the relative expression of the indicated genes regulated by TLR8 and/or TLR7 in the same mice using the NanoString technology.
Figure 8C:
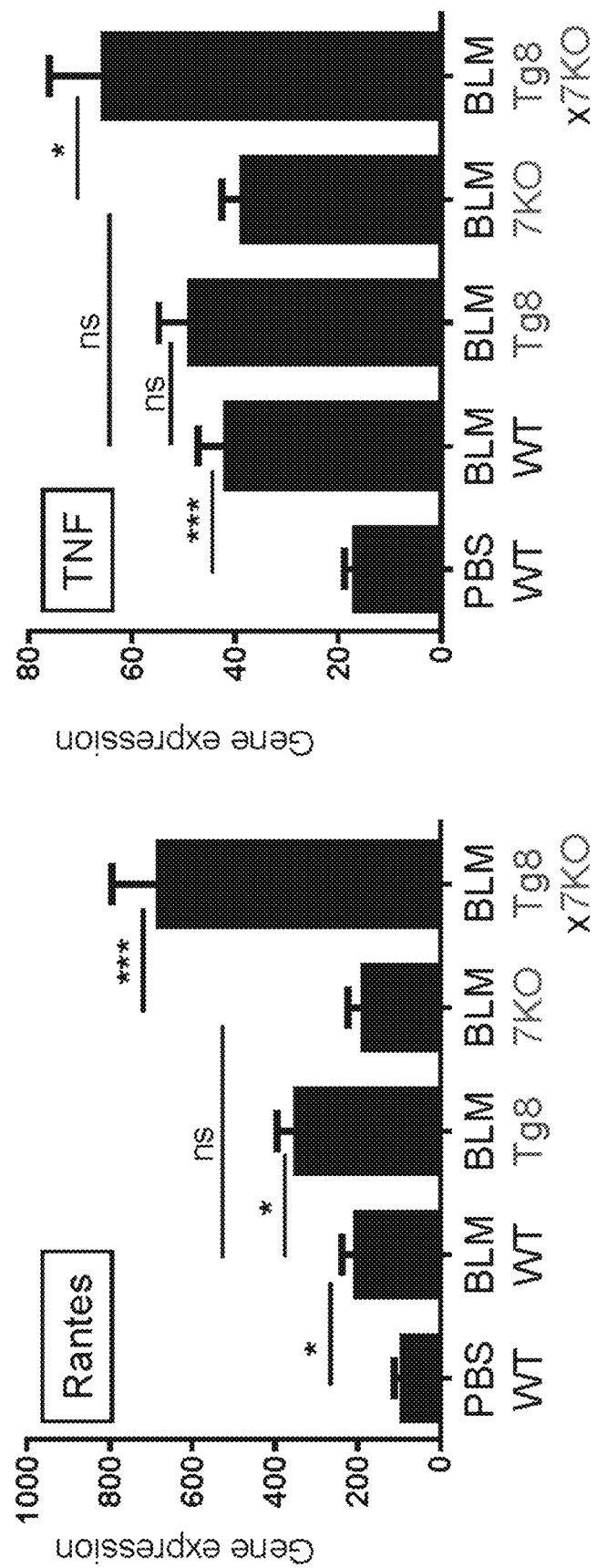
Figure 8D:
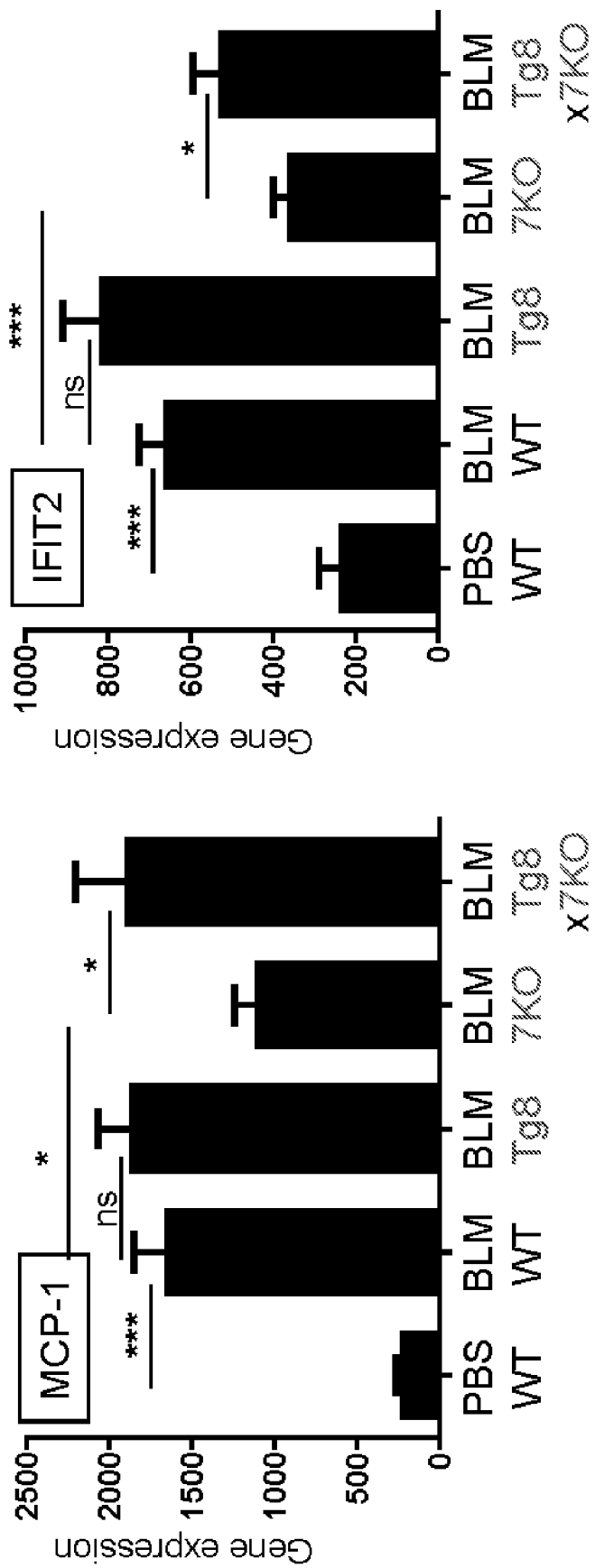
FIG. 8D is the relative expression of the indicated genes regulated by TLR8 and/or TLR7 using the NanoString technology.
Figure 8D:
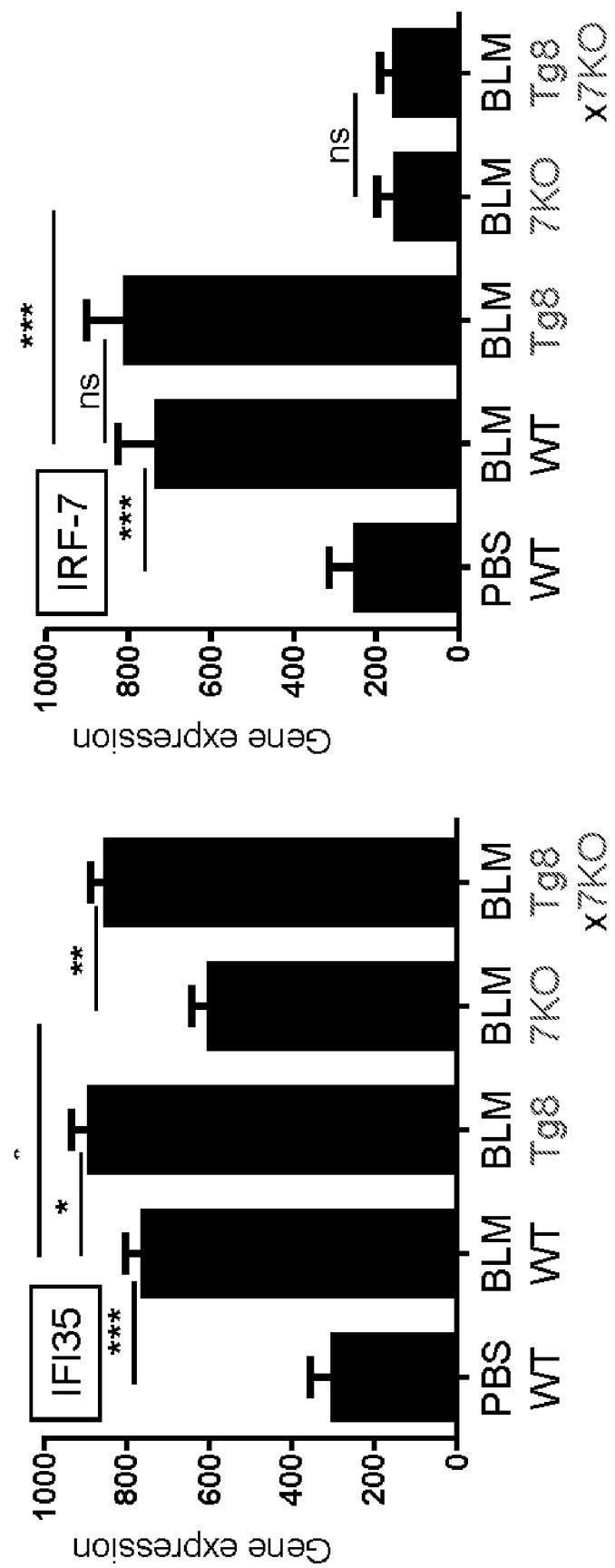

First, it was observed that the infiltration of pDCs was reduced in TLR7ko mice (FIG. 8B). Second, the inflammatory response observed in the skin was dependent on both TLR7 and TLR8 with key differences between the genes of interest (FIGS. 8C and 8D). The expression of genes such as CXCL9 (MIG), CXCL10 (IP-10), RANTES or TNF seemed to be regulated by TLR8 signaling as their expression was increased in TLR8Tg mice irrespective of the presence of TLR7 (FIG. 8C). Other genes, mostly regulated by IFN-$\alpha$, were reduced in TLR7ko mice (with sometimes a contribution of TLR8) (FIGS. 8C and 8D) which may be explained by the reduced skin infiltration of pDCs observed in TLR7ko mice (FIG. 8B).

Figure 8E:
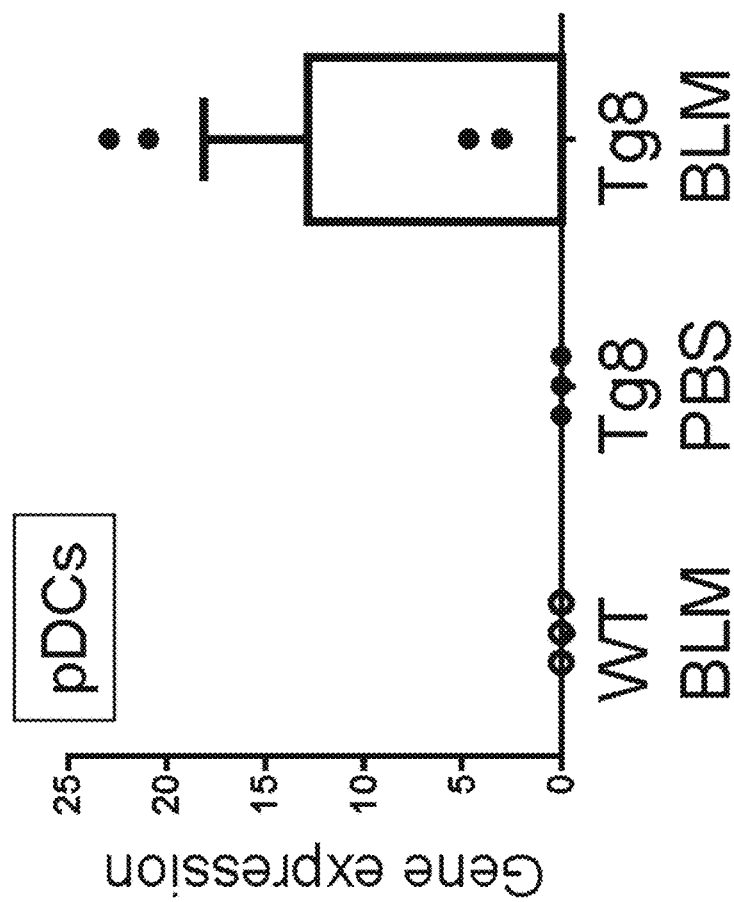
FIG. 8E shows the gene expression levels of huTLR8 by qPCR for macrophages (F4/80$^+$, CD11b$^+$) purified from WT or Tg8 mice (N=3-4) that received PBS or 4 weeks of BLM as indicated.
Figure 8F:
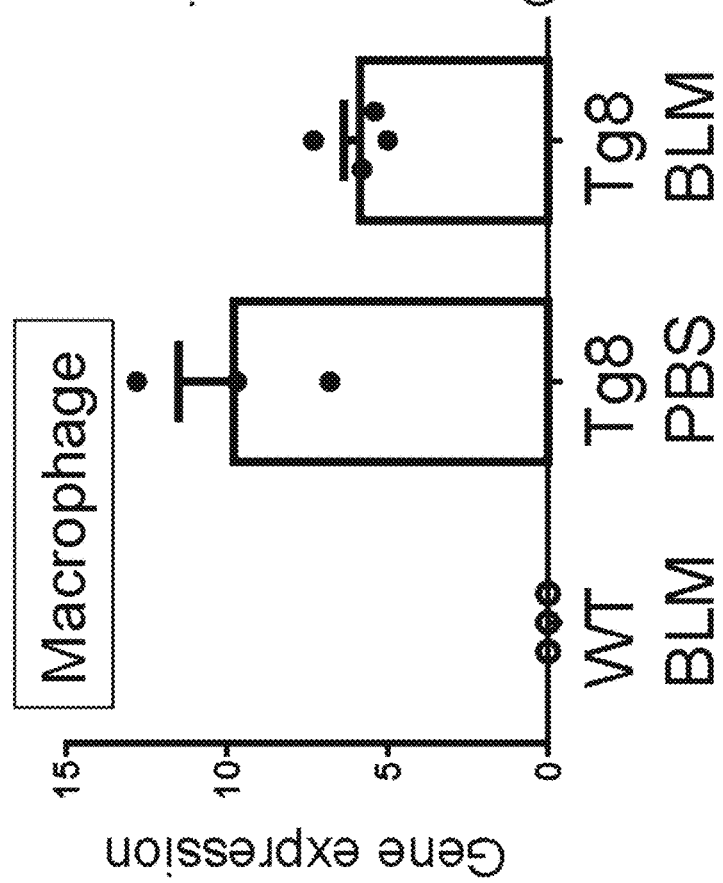
FIG. 8F is a graph of the gene expression levels of huTLR8 by qPCR for purified pDCs (F4/80$^-$, CD11b$^-$ and B220$^+$, SiglecH$^+$, BST2$^+$) from WT or Tg8 mice (N=3-4) that received PBS or 4 weeks of BLM as indicated. All results are represented as a mean±SEM from three to six independent experiments for each group and statistical significance was evaluated using a Mann-Whitney U-test and *p<0.05; p<0.01; *p<0.001.

In order to better understand how the BLM model relates to the human situation with respect to TLR8 activation of pDCs, the expression levels of TLR8 in purified splenic macrophages was quantified which we have shown to express huTLR8 (Guidacci et al. 2013) (FIG. 8E) or in splenic pDCs (FIG. 8F) in mice treated for 4 weeks either with PBS or BLM. It was observed that in mice injected with PBS, pDCs do not express TLR8 but that this receptor is upregulated in pDCs following the induction of fibrosis with BLM (FIG. 8F).

Altogether these data indicated that TLR8 is the key RNA-sensing TLR involved in the establishment of fibrosis and can promote both an increase in the inflammatory response but also skin fibrosis.

Figure 9A:
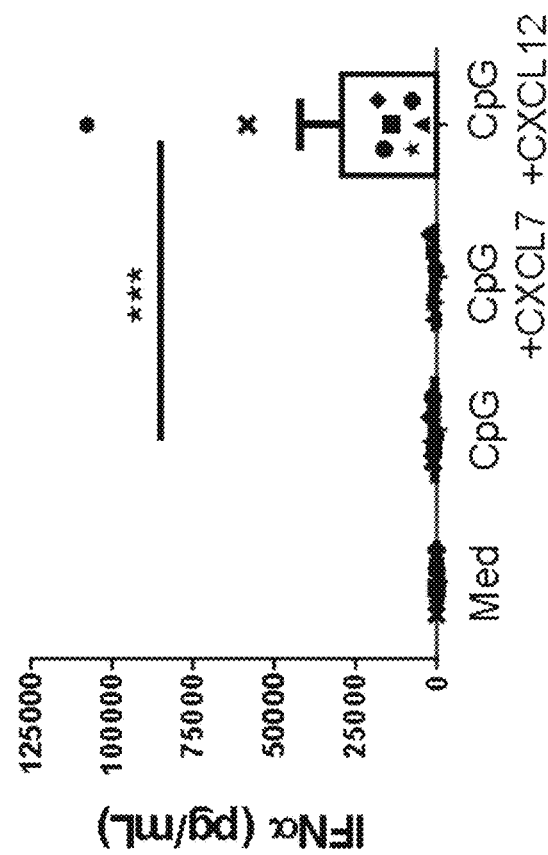
FIG. 9A is a graph showing IFN-α as quantified in the supernatants by ELISA of purified pDCs from HDs were cultured in media alone (control), with either a CpG TLR9 agonist or with CpG and either CXCL10 or CXCL9.
Figure 9B:
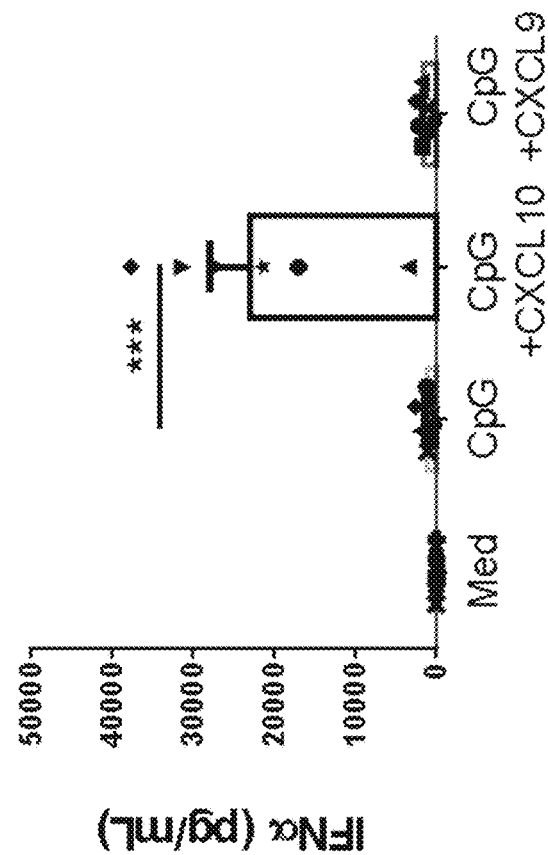
FIG. 9B is a graph showing IFN-α as quantified in the supernatants by ELISA of purified pDCs from HDs were cultured in media alone (control), with either a CpG TLR9 agonist or with CpG and either CXCL7 or CXCL12. Results are represented as a mean±SEM with individual donor shown and statistical significance evaluated using a Mann-Whitney U-test and *p<0.05; p<0.01; *p<0.001.

Example 9—Impact of CXCL7, CXCL9, CXCL10 and CXLC 12 on TLR9 Mediated Activation of pDCs Purified pDCs from HDs were cultured in media alone (control), with either a CpG TLR9 agonist (0.25 µM) or with CpG and either CXCL10, CXCL9, CXCL7 or CXCL12 (all at 10 µg/ml). IFN-α was quantified in the supernatants by ELISA. As seen in FIG. 9, CXCL10 and CXCL12 also potentiated IFNα production from TLR9 in pDCs from HDs but CXCL9 and CXCL7 did not.

Example 10—CXCL4 and CXCL10 TLR9-Mediated Activation of pDCs does not Take Place Solely Via CXCR3

Figure 10B:
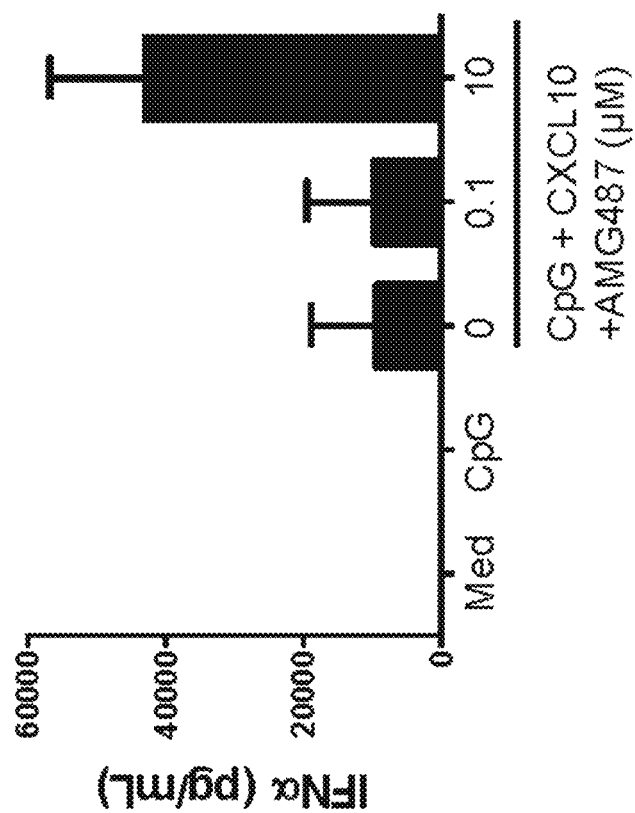
FIG. 10B is a graph of IFN-α quantified in the supernatants by ELISA of purified pDCs from HDs were cultured in media alone (control), with either a CpG TLR9 agonist or with CpG and either CXCL10 alone or in the presence of the CXCR3 inhibitor AMG487 at the indicated concentration for 24 hours. IFN-α was quantified in the supernatants by ELISA. Results are represented as a mean±SEM.
Figure 10A:
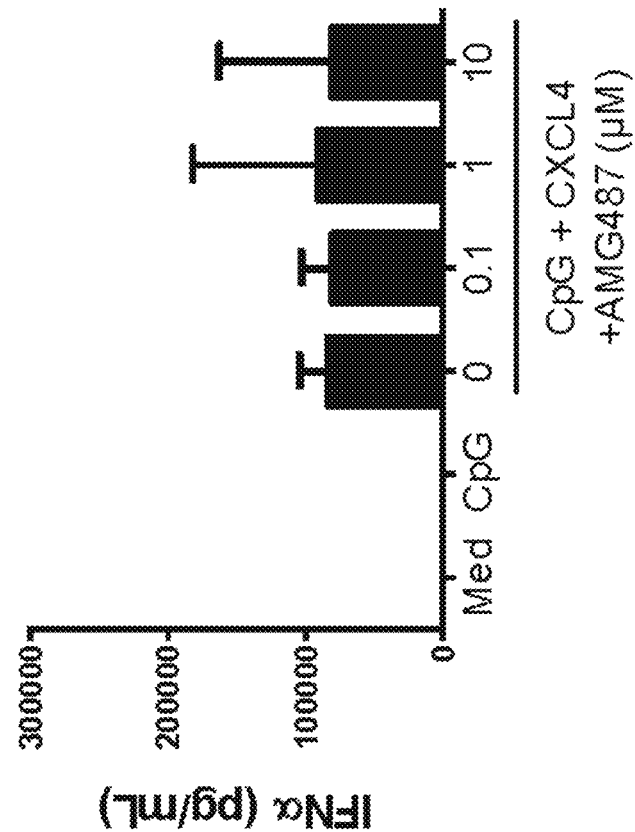
FIG. 10A is a graph of IFN-α quantified in the supernatants by ELISA of purified pDCs from HDs were cultured in media alone (control), with either a CpG TLR9 agonist or with CpG and either CXCL4 alone or in the presence of the CXCR3 inhibitor AMG487 at the indicated concentration for 24 hours.

Purified pDCs from HDs were cultured in media alone (control), with either a CpG TLR9 agonist (0.25 µM) or with CpG and either CXCL4 or CXCL10 (both at 10 µg/ml) alone or in the presence of the CXCR3 inhibitor AMG487 at 0, 0.1, 1 or 10 µM for 24 hours. IFN-α was quantified in the supernatants by ELISA. As shown in FIG. 10, the inhibition of CXCR3 had no effect on the activation of TLR9 by CXCL4 and CXLC10 indicating the chemokines are not activating TLR9 in pDCs via the CXCR3 receptor.

Example 11—CXCL4 Negatively Regulates TLR9-Mediated Activation of Human B Cells

Human B cells were purified from PBMC of HDs and cultured for 6 hours or 24 hours either with medium only, with CpG-B (at 0.15 µM), with CXCL4 (at 10 µg/ml) alone or with a combination of CpG-B and CXCL4. IL-6, TNF, and IL-10 gene levels were measured at 6 hours post culture using PCR. The secretion of cytokines/chemokines in the supernatants was quantified using Luminex. CD83, CD80, CD86 and CD69 expression was measured by flow cytometry at 24 hour post culture.

Figure 11:
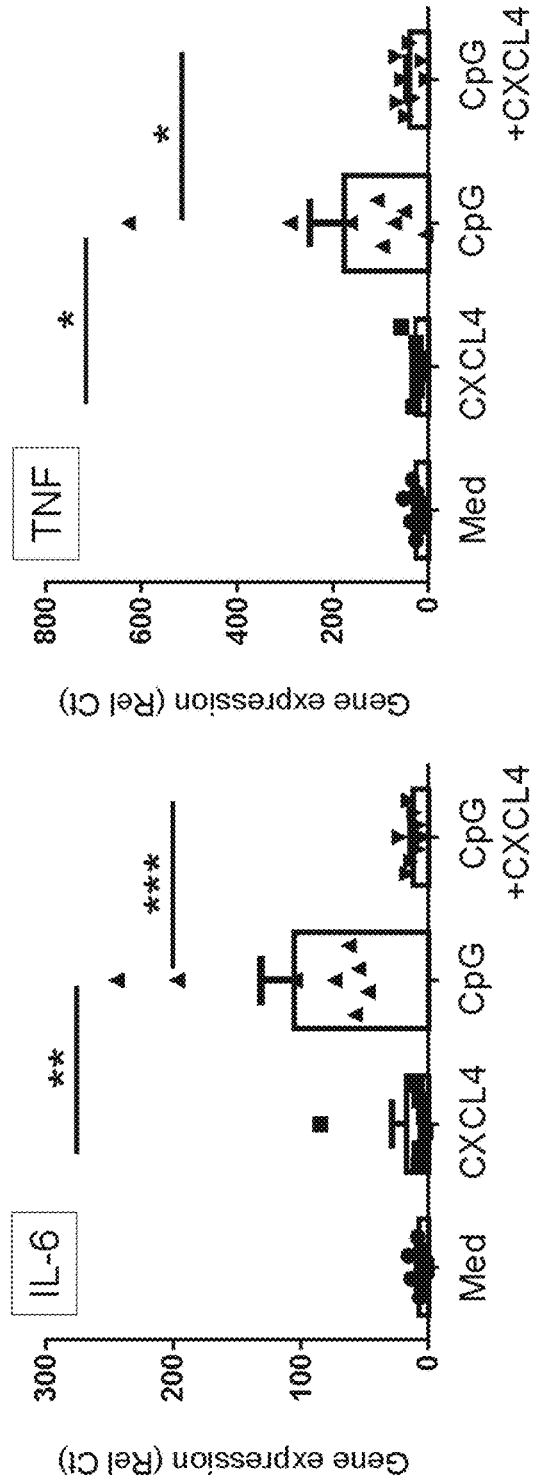
FIG. 11 shows that CXCL4 negatively regulates TLR9 (CpG-B)-mediated activation of human B cells.
Figure 11A:
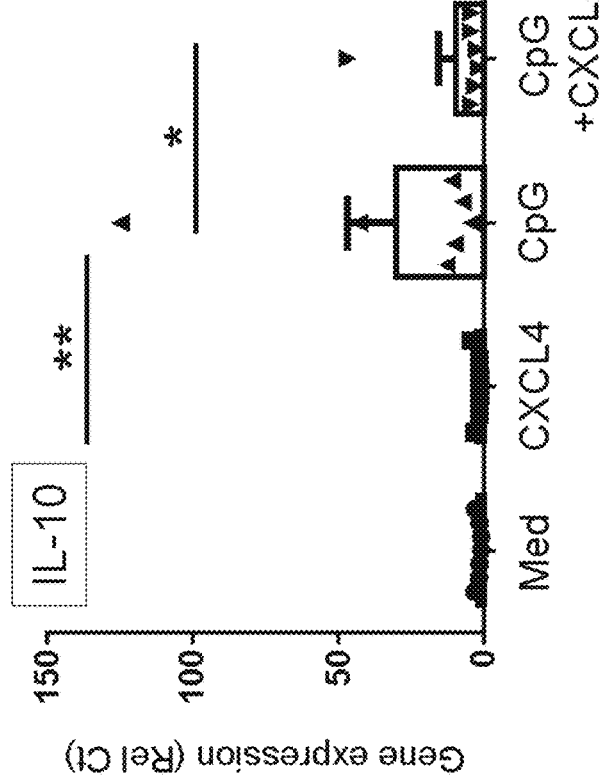
FIG. 11A is a graph of the gene levels of IL-6, TNF, and IL-10 in human B cells purified from PBMC of HDs and cultured for 6 hours either with medium only, with CpG-B, with CXCL4 alone or with a combination of CpG-B and CXCL4.
Figure 11B:
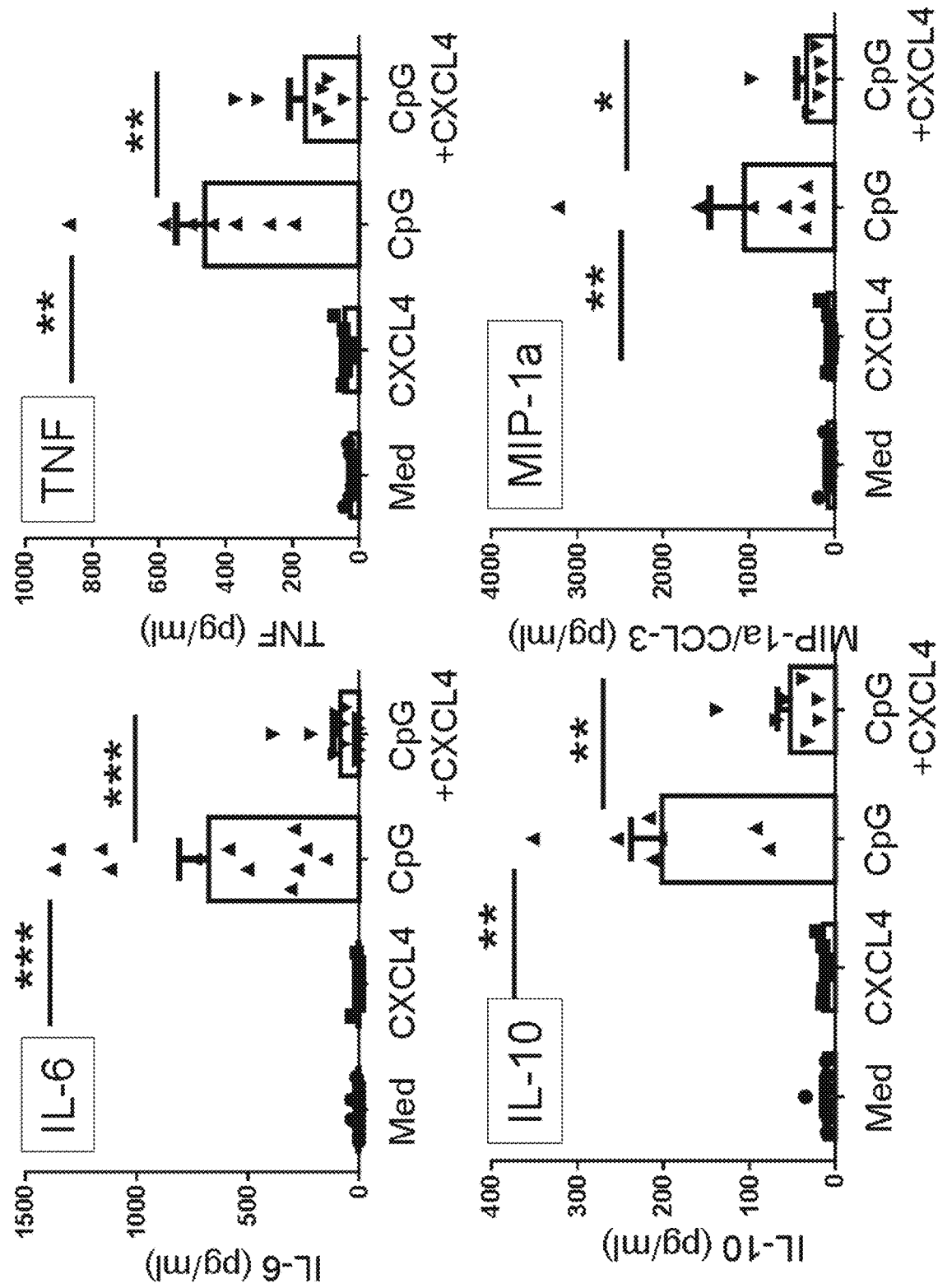
FIG. 11B is a graph of the secretion of the indicated cytokines and chemokines in human B cells purified from PBMC of HDs and cultured for 6 hours either with medium only, with CpG-B, with CXCL4 alone or with a combination of CpG-B and CXCL4.
Figure 11C:
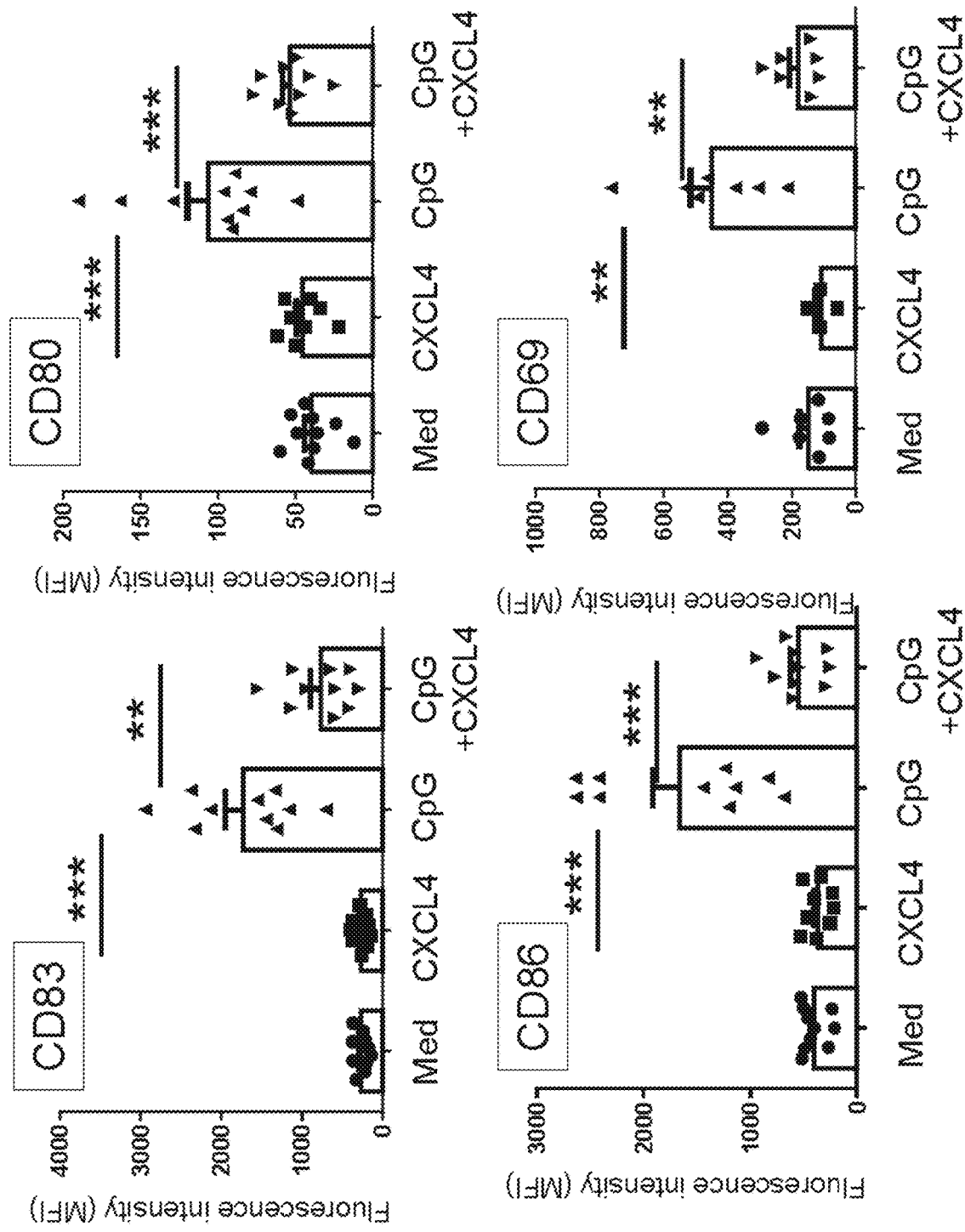
FIG. 11C is a graph of CD83, CD80, CD86 and CD69 expression was measured by flow cytometry in human B cells purified from PBMC of HDs and cultured for 24 hours either with medium only, with CpG-B, with CXCL4 alone or with a combination of CpG-B and CXCL4. Results are represented as a mean±SEM and individual donors are shown and statistical significance evaluated using a Mann-Whitney U-test and *p<0.05; p<0.01; *p<0.001.

As seen in FIG. 11 in B cells, CXCL4 negatively regulated the expression of IL-6, TNF and IL-10 as shown by PCR in FIG. 11A and by the amount of protein produced by the cells as shown in FIG. 11B.

Figure 12A:
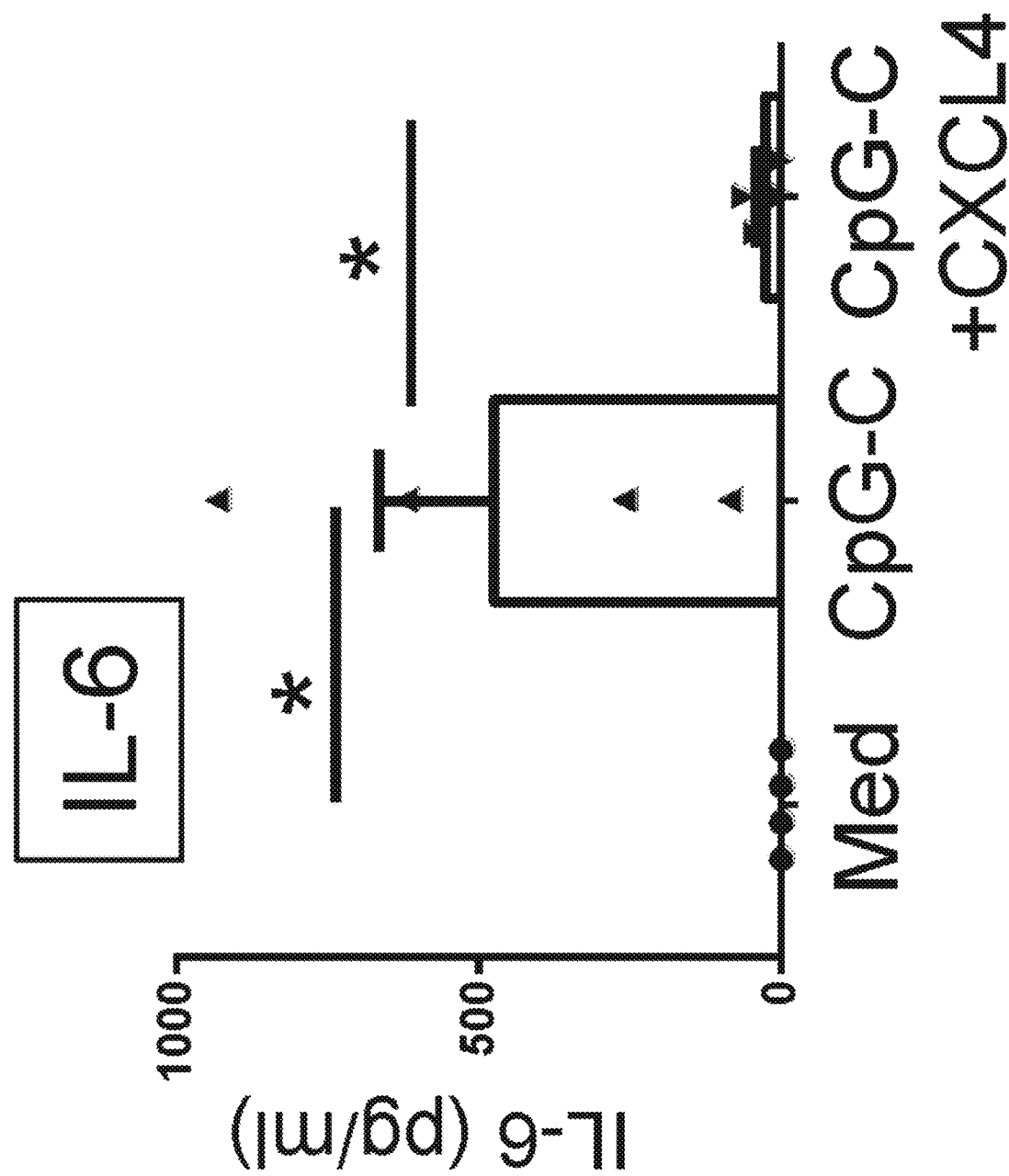
FIG. 12A shows the IL-6 gene levels as measured at 6 hours post culture of human B cells purified and cultured either with medium only, with CpG-C alone or with a combination of CpG-C and CXCL4.
Figure 12B:
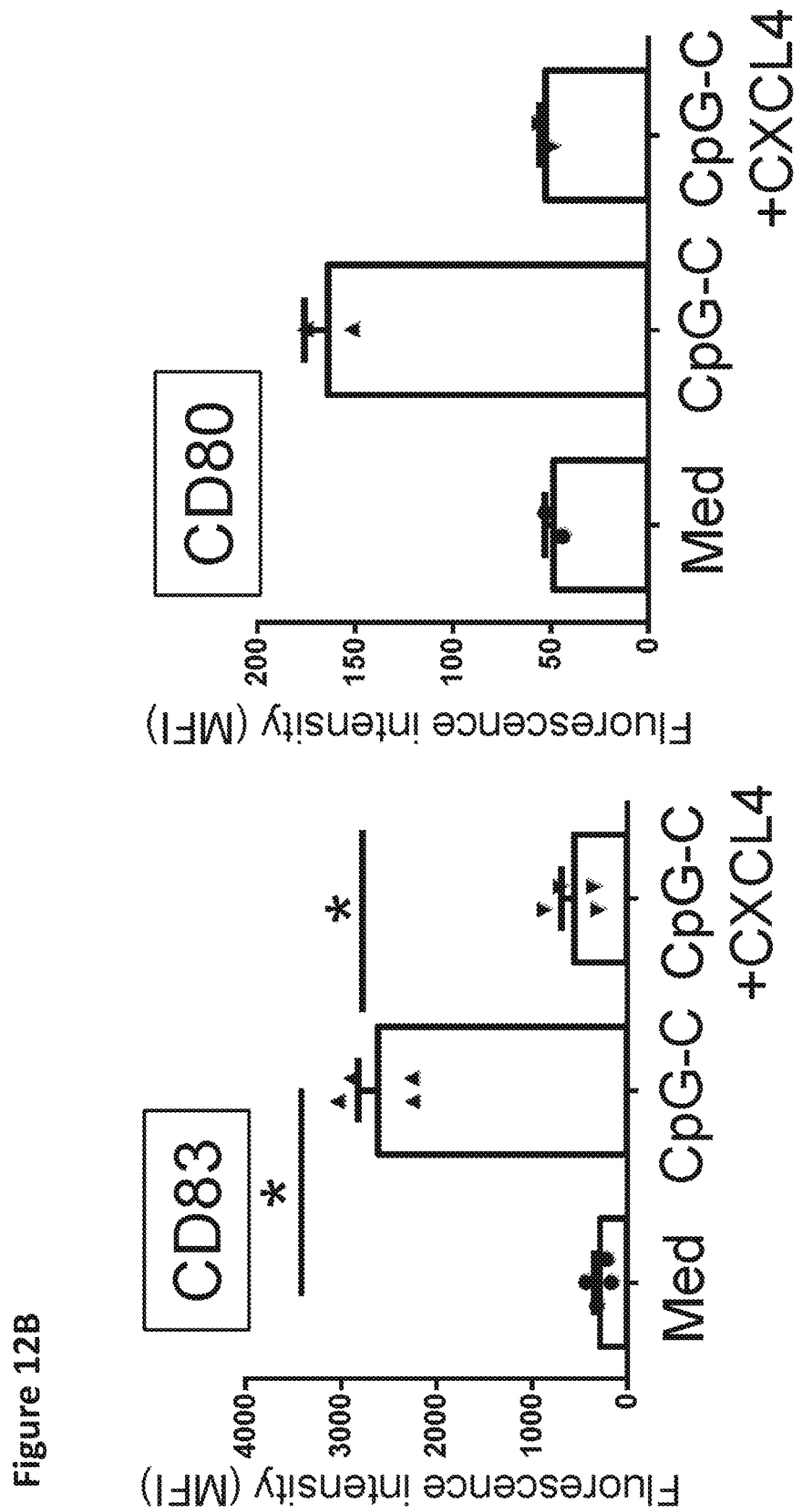
FIG. 12B shows the CD83, CD80, CD86 and CD69 expression measured by flow cytometry at 24 hours post culture of human B cells purified and cultured either with medium only, with CpG-C alone or with a combination of CpG-C and CXCL4. Results are represented as a mean±SEM and individual donors are shown and statistical significance evaluated using a Mann-Whitney U-test and *p<0.05; p<0.01; *p<0.001.
Figure 12B:
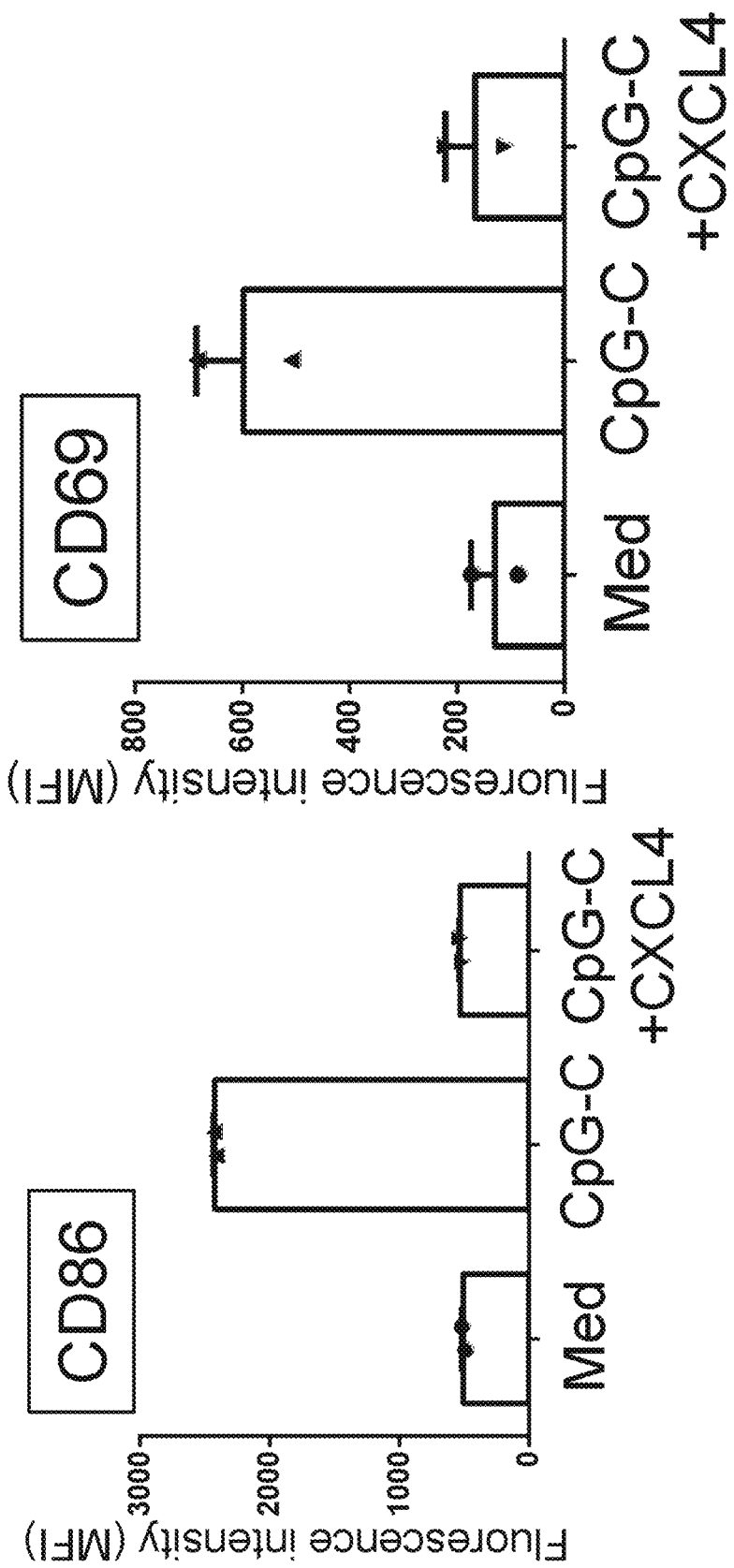

Human B cells were purified and cultured for 6 hours or 24 hours either with medium only, with CpG-C (at 0.15 µM) alone or with a combination of CpG-C and CXCL4 (at 10 µg/ml). IL-6 gene levels was measured at 6 hour post culture by PCR and CD83, CD80, CD86 and CD69 expression was measured by flow cytometry at 24 hour post culture. The same results were shown in FIG. 12 when CpG-C was used as shown in FIG. 11 when CpG-B was used-CXCL4 negatively regulated TLR9 activation.

Example 12—CXCL4 has Little Effect on TLR7-Mediated Activation of Human B Cells

Human B cells were purified from PBMC of HDs and cultured for 6 hours or 24 hours either with medium only, with R848, a TLR7 agonist (at 0.15 µM), with CXCL4 (at 10 µg/ml) alone or with a combination of R848 and CXCL4. IL-6 and TNF gene levels were measured at 6 hour post culture by PCR, secretion of IL-6 and TNF were quantified using luminex and CD83 and CD80 expression was measured by flow cytometry at 24 hour post culture.

Figure 13A:
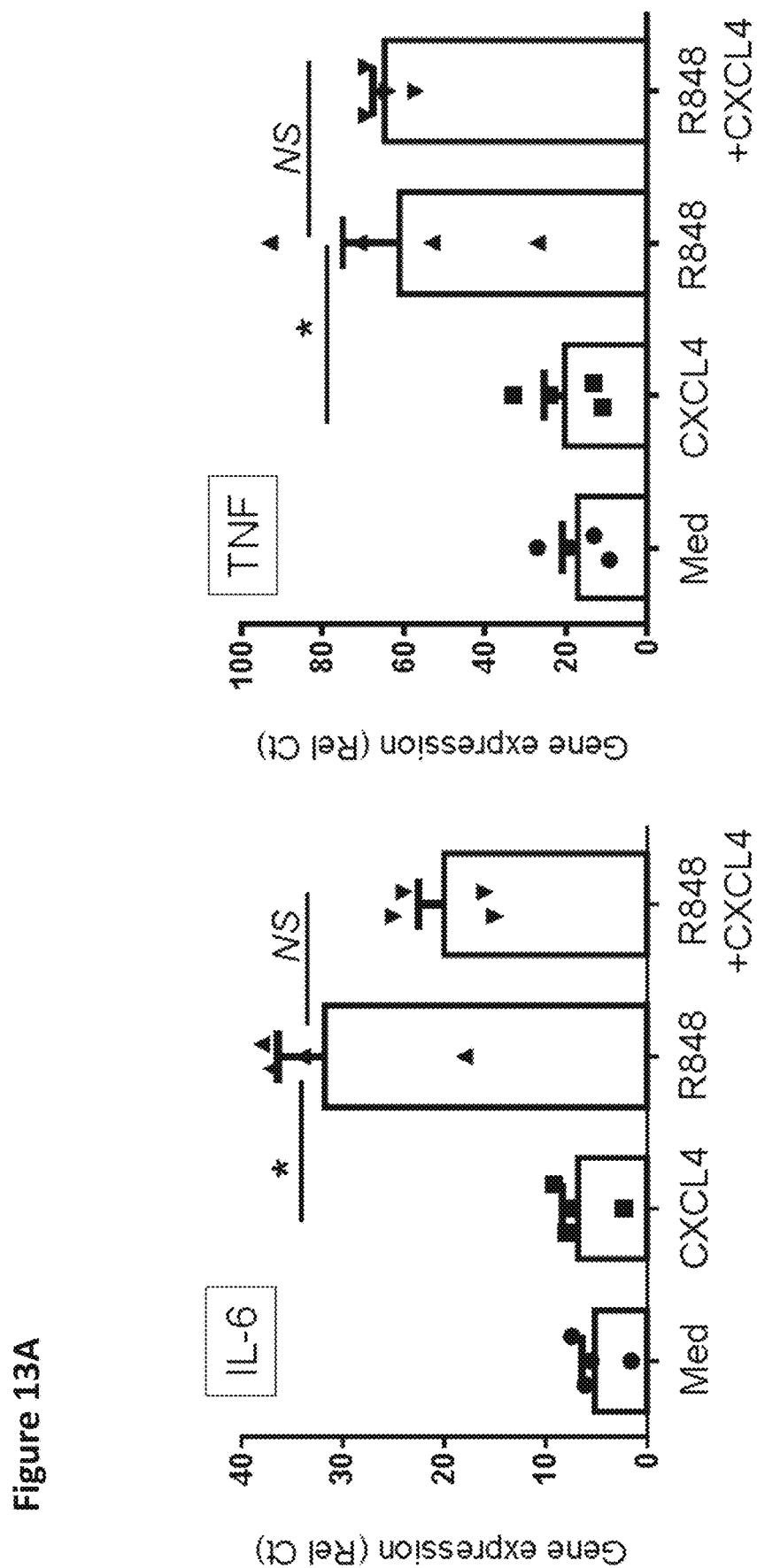
FIG. 13A show the IL-6 and TNF gene levels measured at 6 hours post culture in human B cells purified from PBMC of HDs and cultured either with medium only, with R848, with CXCL4 alone or with a combination of R848 and CXCL4.
Figure 13B:
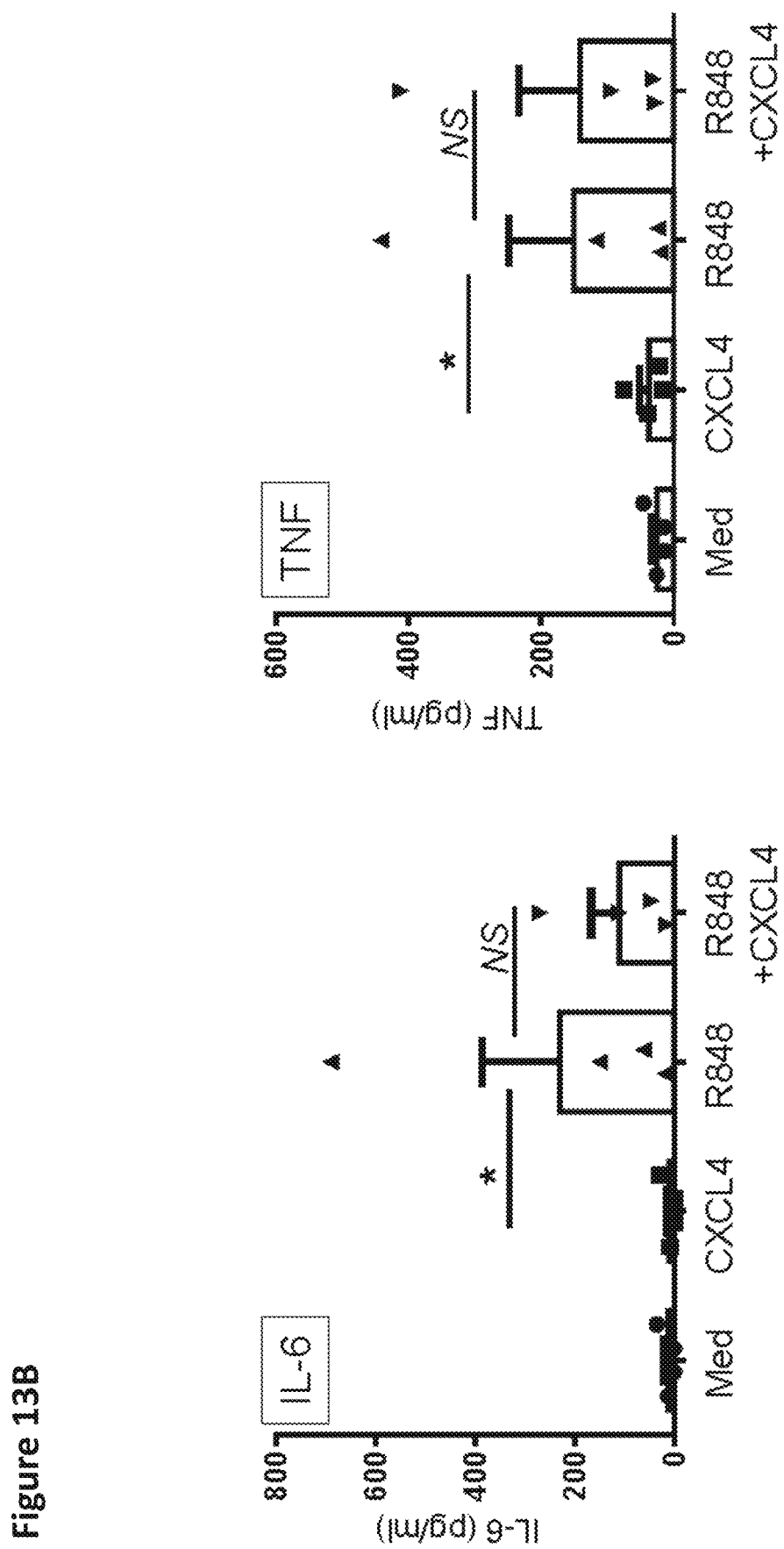
FIG. 13B shows the amount of secretion of IL-6 and TNF measured at 6 hours post culture in human B cells purified from PBMC of HDs and cultured either with medium only, with R848, with CXCL4 alone or with a combination of R848 and CXCL4.
Figure 13C:
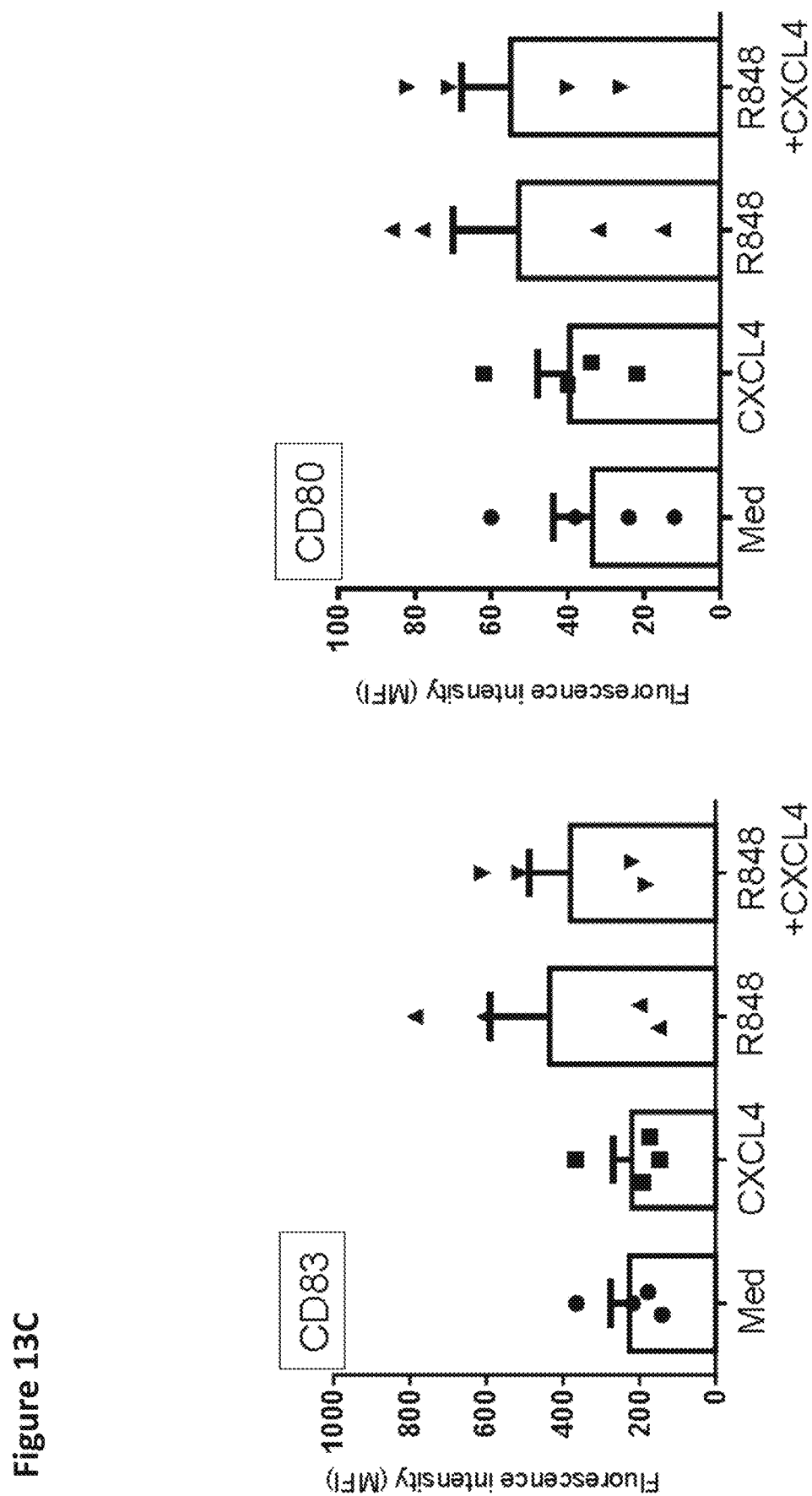
FIG. 13C show CD83 and CD80 expression measured by flow cytometry at 24 hours post culture in human B cells purified from PBMC of HDs and cultured either with medium only, with R848, with CXCL4 alone or with a combination of R848 and CXCL4. Results are represented as a mean±SEM and individual donors are shown and statistical significance evaluated using a Mann-Whitney U-test and *p<0.05; p<0.01; *p<0.001.

As shown in FIG. 13, CXCL4 had little effect on the gene expression or secretion of IL-6 and TNF when activated by TFR7.

Example 13—Impact of CXCL4, CXCL7, CXCL9, CXCL10 and CXCL12 on TLR9-Mediated Activation of Human B Cells Purified B cells from HDs were cultured in media alone (control), with either a CpG TLR9 agonist (0.15 µM) or with CpG and either CXCL4, CXCL10, CXCL9, CXCL4, CXCL7 or CXCL12 (all at 10 µg/ml). IL-6 was quantified in the supernatants by ELISA.

As shown in FIG. 14, CXCL4, CXCL9, CXCL10, and CXCL12 inhibited the activation of B cells via TLR9 as shown by the production of IL-6.

Example 14—CXCL4 and CXCL10 TLR9-Mediated Inhibition of B Cells Not Take Place Solely Via CXCR3

Purified B cells from HDs were cultured in media alone (control), with either a CpG TLR9 agonist (0.25 µM) or with CpG and CXCL4 or CXCL10 (10 µg/ml) alone or in the presence of the CXCR3 inhibitor AMG487 at 0, 0.1, 1 or 10 µM for 6 hours or 24 hours. IL-6 was quantified by ELISA at 24 hours and IL-6 and TNF gene expression levels were quantified by q-PCR at 6 hours and CD83, CD80, CD86 and CD69 expression was measured by flow cytometry at 24 hours post culture.

Figure 15A:
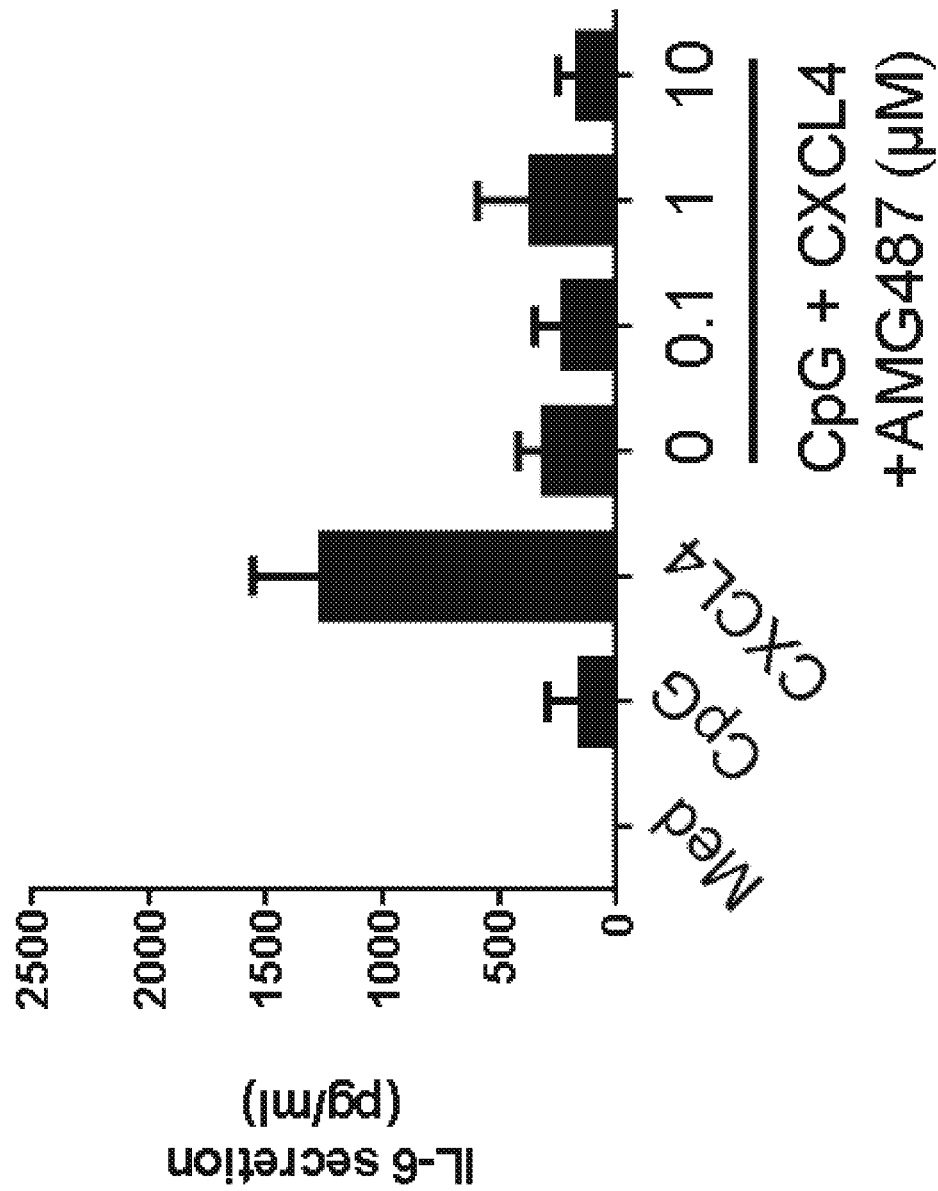
FIG. 15A is a graph of IL-6 as quantified by ELISA at 24 hours in purified B cells from HDs cultured in media alone (control), with either a CpG TLR9 agonist or with CpG and CXCL4 alone or in the presence of the CXCR3 inhibitor AMG487 at the indicated concentration.
Figure 15B:
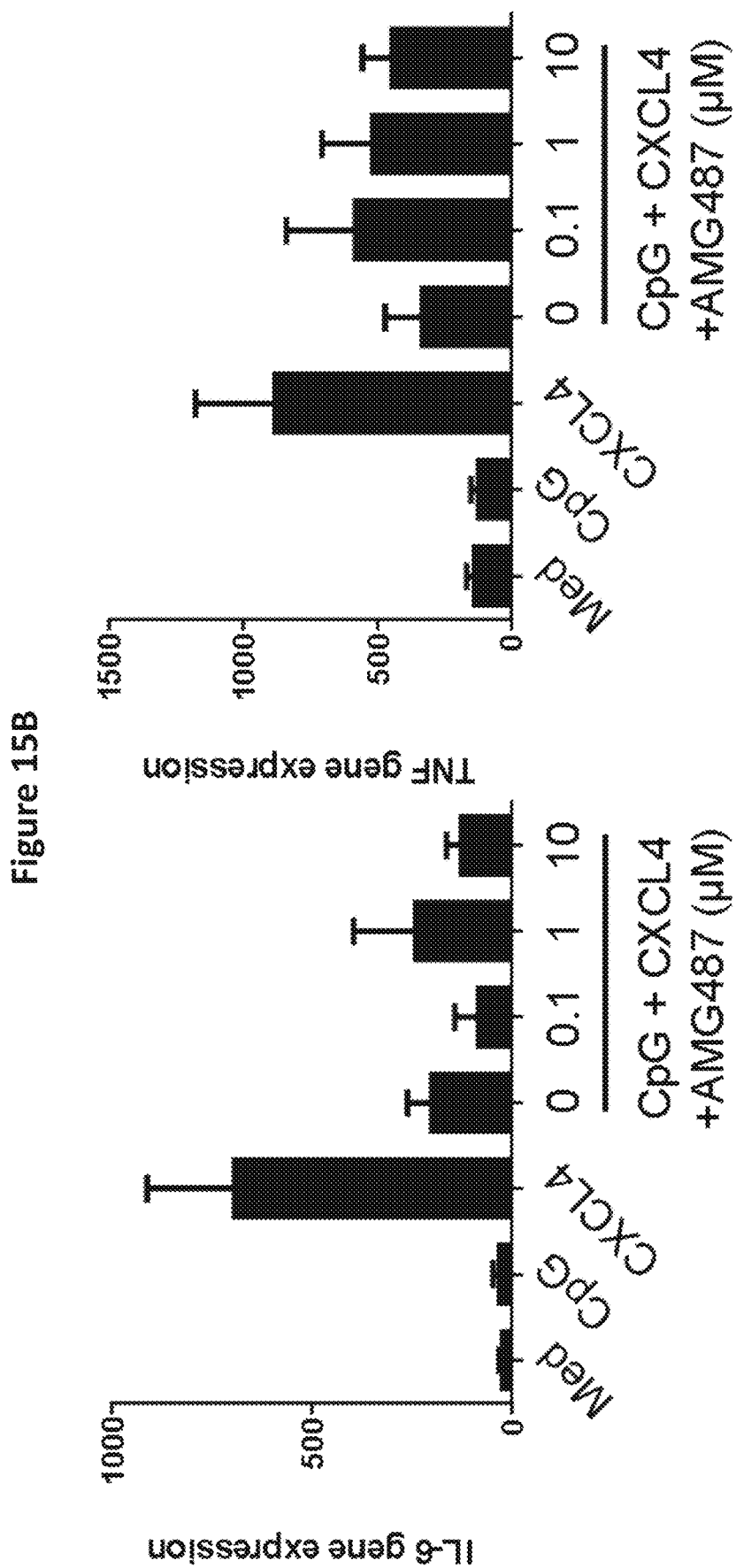
FIG. 15B is a graph of IL-6 and TNF gene expression levels as quantified by qPCR at 6 hours in purified B cells from HDs cultured in media alone (control), with either a CpG TLR9 agonist or with CpG and CXCL4 alone or in the presence of the CXCR3 inhibitor AMG487 at the indicated concentration.
Figure 15C:
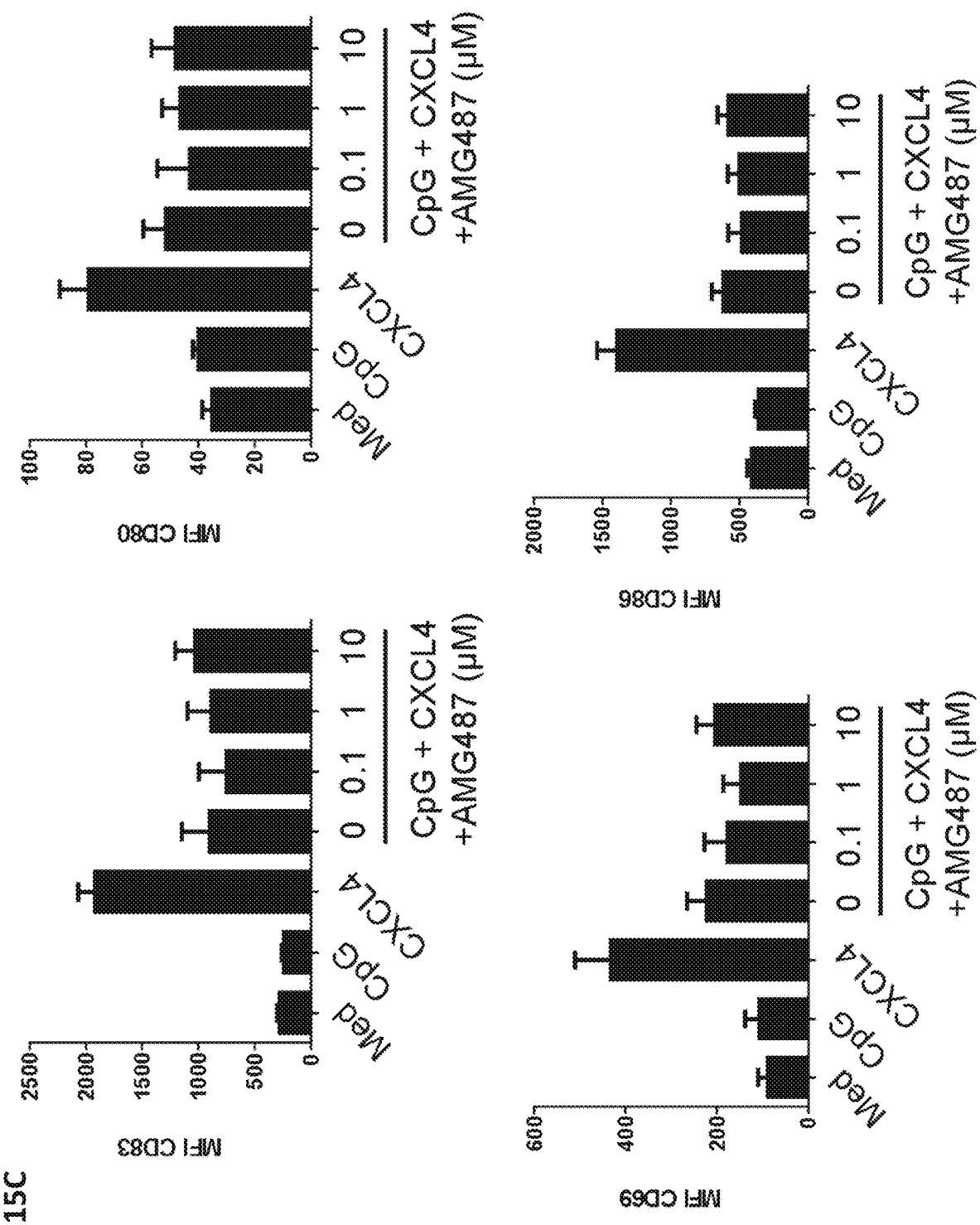
FIG. 15C is a graph of CD83, CD80, CD86 and CD69 expression as measured by flow cytometry at 24 hours post culture in purified B cells from HDs cultured in media alone (control), with either a CpG TLR9 agonist or with CpG and CXCL4 alone or in the presence of the CXCR3 inhibitor AMG487 at the indicated concentration. Results are represented as a mean±SEM and statistical significance evaluated using a Mann-Whitney U-test and *p<0.05; p<0.01; *p<0.001.
Figure 16A:
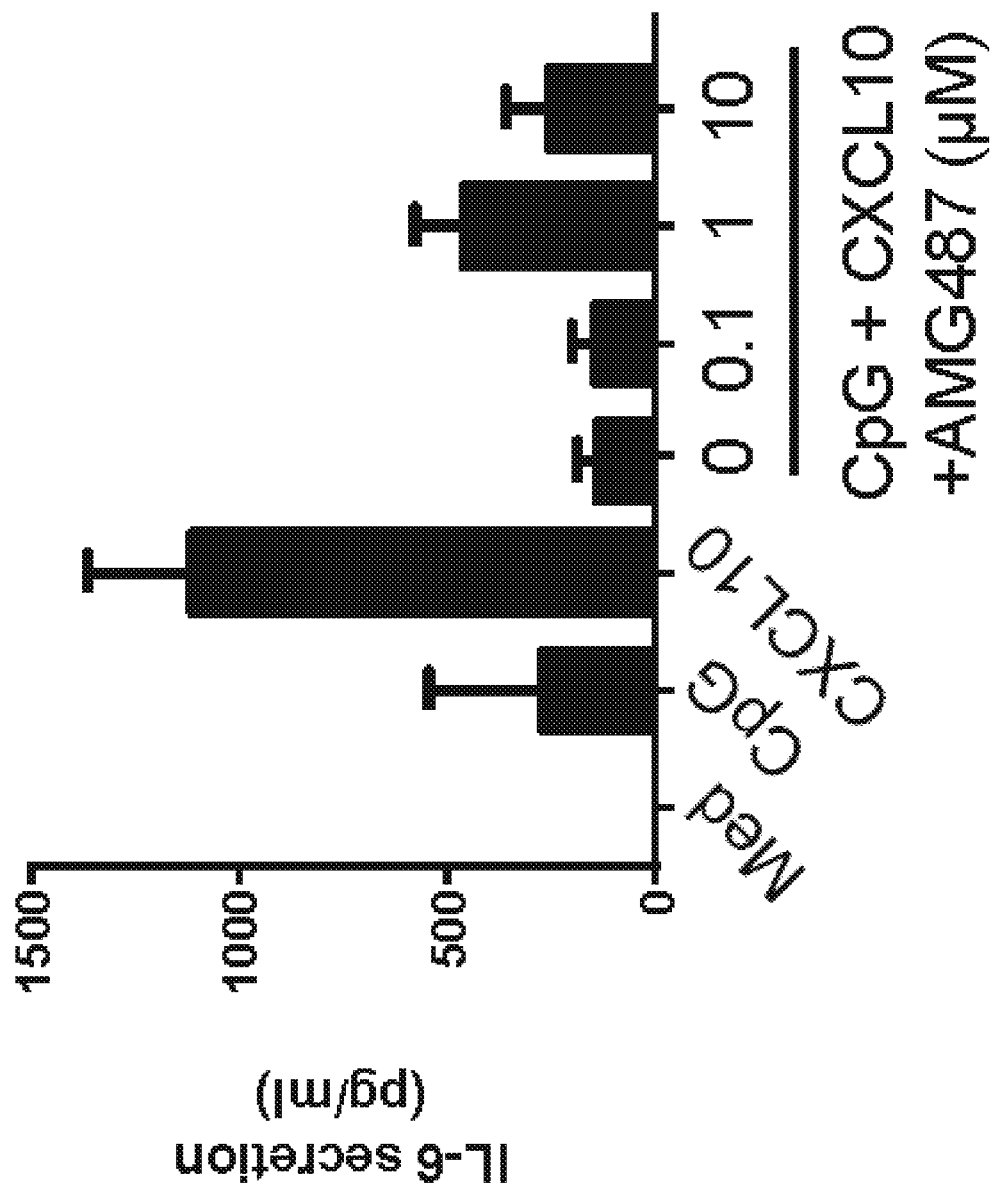
FIG. 16A is a graph of IL-6 as quantified by ELISA at 24 hours post culture from purified B cells from HDs cultured in media alone (control), with either a CpG TLR9 agonist or with CpG and CXCL10 alone or in the presence of the CXCR3 inhibitor AMG487 at the indicated concentration.
Figure 16B:
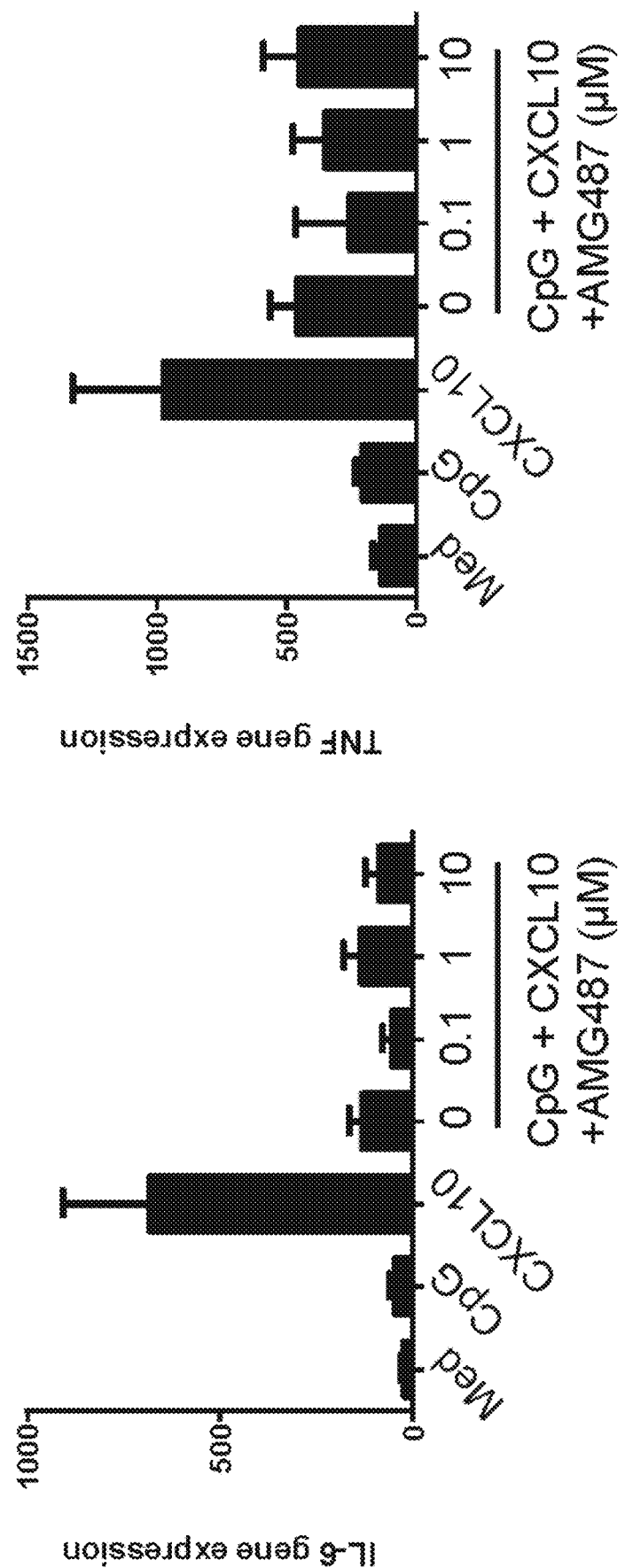
FIG. 16B is a graph of IL-6 and TNF gene expression levels as quantified by qPCR at 6 hours post culture from purified B cells from HDs cultured in media alone (control), with either a CpG TLR9 agonist or with CpG and CXCL10 alone or in the presence of the CXCR3 inhibitor AMG487 at the indicated concentration.
Figure 16C:
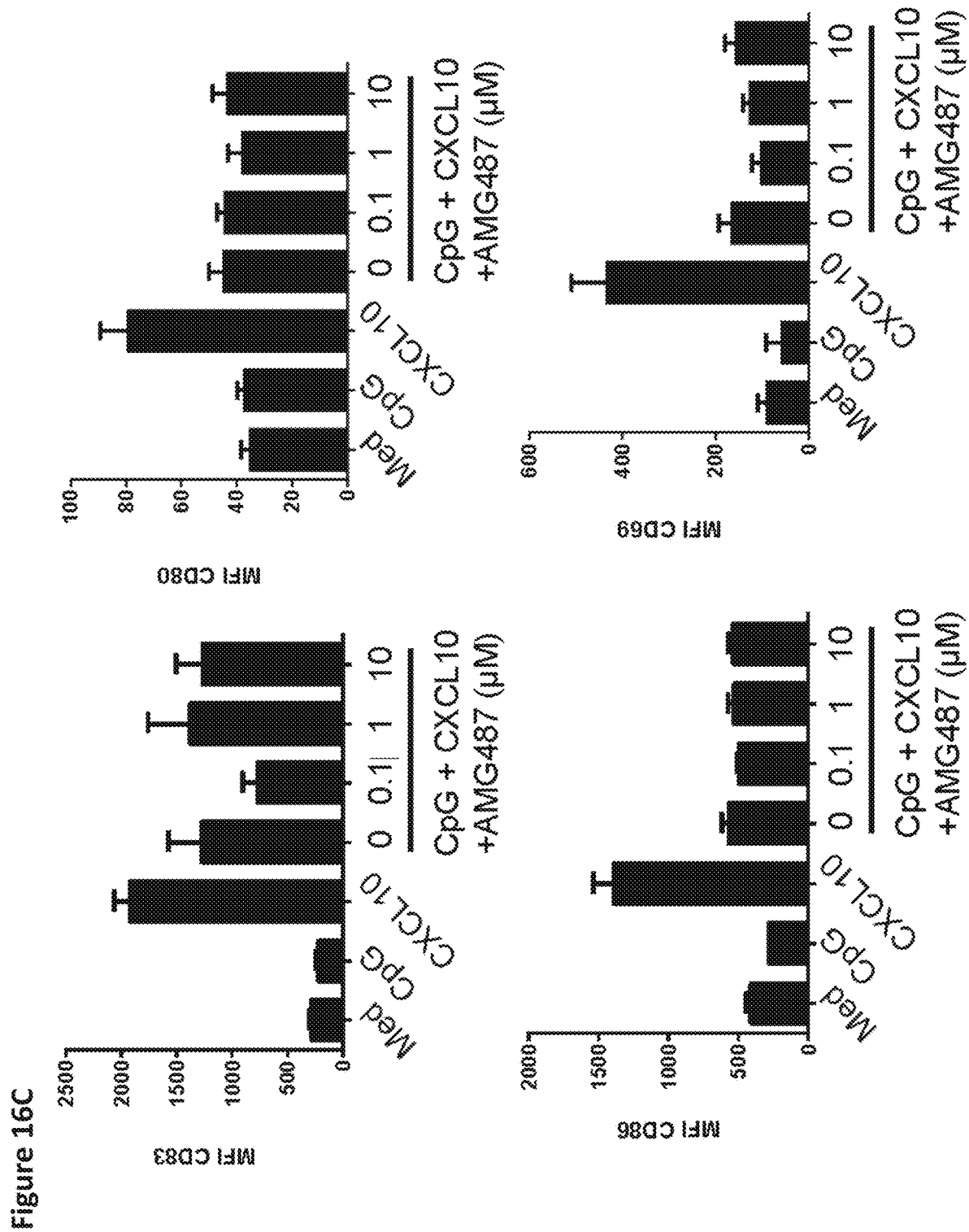
FIG. 16C is a graph of CD83, CD80, CD86 and CD69 expression as measured by flow cytometry at 24 hours post culture from purified B cells from HDs cultured in media alone (control), with either a CpG TLR9 agonist or with CpG and CXCL10 alone or in the presence of the CXCR3 inhibitor AMG487 at the indicated concentration. Results are represented as a mean±SEM and statistical significance evaluated using a Mann-Whitney U-test and *p<0.05; p<0.01; *p<0.001.

As shown in FIGS. 15 (CXCL4) and 16 (CXCL10), the inhibition of CXCR3 had no effect on the inhibition of TLR9 by CXCL4 and CXLC10 indicating the chemokines are not acting on TLR9 in B cells solely via the CXCR3 receptor.

Example 15 CXCL4 and TLR8 Synergize to Induce IL-6/TNF Production by Human Macrophage but CXCL4 Reduced IP-10 Production by TLR8-Activated Macrophages Human macrophages were prepared from purified monocytes by culturing the cells overnight with G-CSF. Cells were then cultured for 24 hours either with medium only, with ORN8L (at 20 µg/ml), with CXCL4 (at 10 µg/ml) alone or with a combination of the CpG-ODN with increasing concentration of CXCL4 (1, 3 or 10 µg/ml). IL-6, TNF and IP-10 secretion in the supernatant was quantified by immunoassay (ELISA) at 24 hours.

Figure 17:
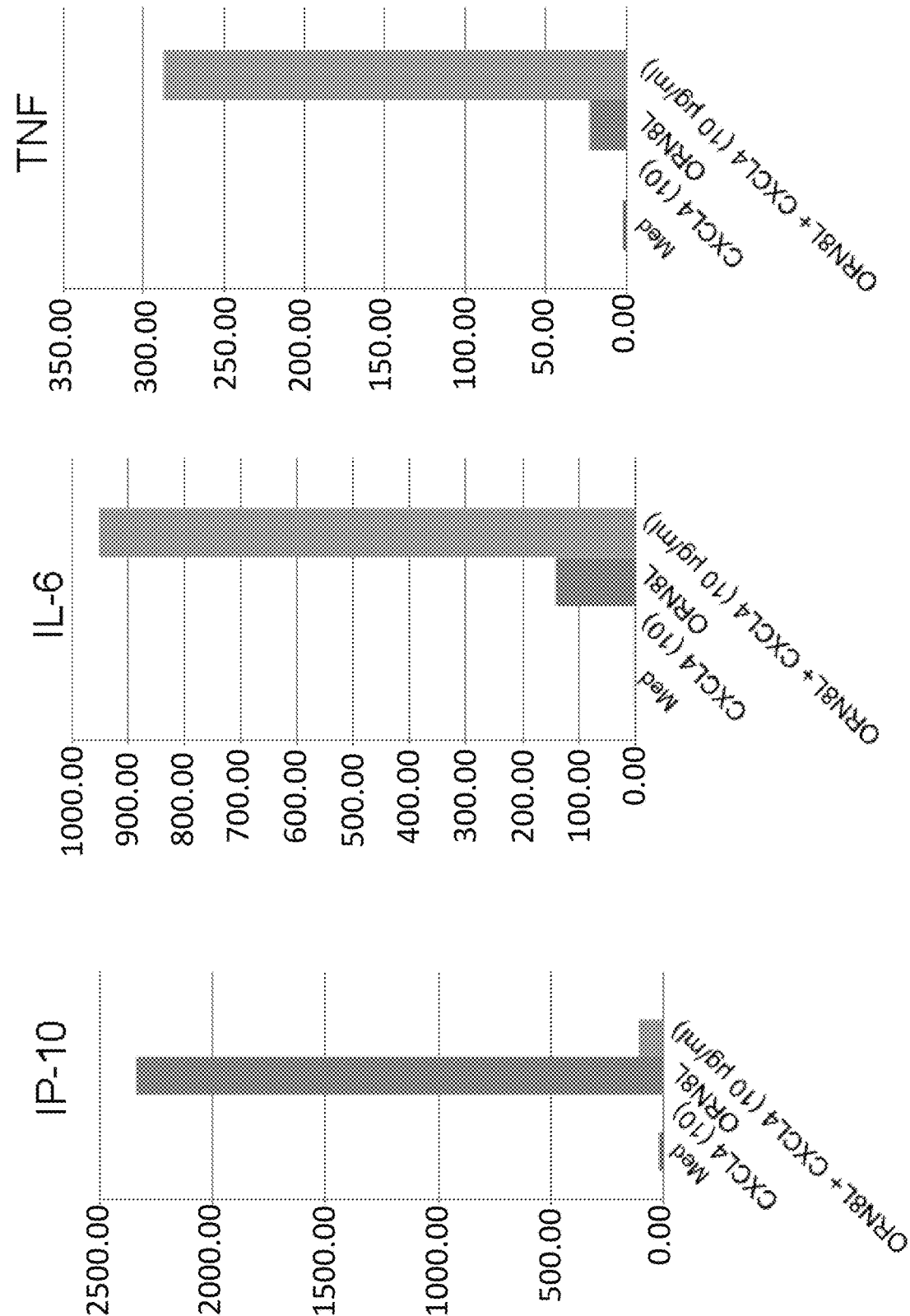
FIG. 17 shows CXCL4 and TLR8 synergize to induce IL-6/TNF production by human macrophages but CXCL4 reduces IP-10 production by TLR8-activated Macrophages.

As shown in FIG. 17, CXCL4 and TLR8 synergized to induce both IL-6 and TNF production in human macrophages but reduced IP-10.

REFERENCES

Barrat et al., Nucleic Acids of Mammalian Origin Can Act as Endogenous Ligands for Toll-like Receptors and May Promote Systemic Lupus Erythematosus. *J Exp Med* 202, 1131-1139 (2005).

Batteux et al., New insights on chemically induced animal models of systemic sclerosis. *Current opinion in rheumatology* 23, 511-518 (2011).

Blanco et al., Induction of dendritic cell differentiation by IFN-alpha in systemic lupus erythematosus. *Science* 294, 1540-1543 (2001).

Cederblad et al., Patients with systemic lupus erythematosus have reduced numbers of circulating natural interferon-alpha-producing cells. *J Autoimmun* 11, 465-470 (1998).

Chia et al., Dendritic cells maintain dermal adipose-derived stromal cells in skin fibrosis. *J Clin Invest* 126, 4331-4345 (2016).

Demaria et al., TLR8 deficiency leads to autoimmunity in mice. *J Clin Invest* 120, 3651-3662 (2010).

Duramad et al., IL-10 regulates plasmacytoid dendritic cell response to CpG-containing immunostimulatory sequences. *Blood* 102, 4487-4492 (2003).

Guiducci et al., Autoimmune skin inflammation is dependent on plasmacytoid dendritic cell activation by nucleic acids via TLR7 and TLR9. *J Exp Med* 207, 2931-2942 (2010).

van Bon et al., Proteome-wide analysis and CXCL4 as a biomarker in systemic sclerosis. *N Engl J Med* 370, 433-443 (2014).

Guiducci et al., RNA recognition by human TLR8 can lead to autoimmune inflammation. *J Exp Med* 210, 2903-2919 (2013).

Guiducci et al., TLR recognition of self nucleic acids hampers glucocorticoid activity in lupus. *Nature* 465, 937-941 (2010).

Guiducci et al., PI3K is critical for the nuclear translocation of IRF-7 and type I IFN production by human plasmacytoid predendritic cells in response to TLR activation. *J Exp Med* 205, 315-322 (2008).

Guiducci et al., Properties regulating the nature of the plasmacytoid dendritic cell response to Toll-like receptor 9 activation. *J Exp Med* 203, 1999-2008 (2006).

Hochberg, Updating the American College of Rheumatology revised criteria for the classification of systemic lupus erythematosus. *Arthritis Rheum* 40, 1725 (1997).

Huang et al., Nintedanib inhibits fibroblast activation and ameliorates fibrosis in preclinical models of systemic sclerosis. *Ann Rheum Dis* 75, 883-890 (2016).

Koca et al., Effectiveness of etanercept in bleomycin-induced experimental scleroderma. *Rheumatology* (Oxford) 47, 172-175 (2008).

Lafyatis et al., B cell depletion with rituximab in patients with diffuse cutaneous systemic sclerosis. *Arthritis Rheum* 60, 578-583 (2009).

LeRoy and Medsger, Jr., Criteria for the classification of early systemic sclerosis. *J Rheumatol* 28, 1573-1576 (2001).

Mayes et al., Prevalence, incidence, survival, and disease characteristics of systemic sclerosis in a large US population. *Arthritis Rheum* 48, 2246-2255 (2003).

Rice et al., A longitudinal biomarker for the extent of skin disease in patients with diffuse cutaneous systemic sclerosis. *Arthritis & rheumatology* 67, 3004-3015 (2015).

Rowland et al., Early, transient depletion of plasmacytoid dendritic cells ameliorates autoimmunity in a lupus model. *J Exp Med* 211, 1977-1991 (2014).

Sisirak et al., Genetic evidence for the role of plasmacytoid dendritic cells in systemic lupus erythematosus. *J Exp Med* 211, 1969-1976 (2014).

Tan et al., Signatures of differentially regulated interferon gene expression and vasculotrophism in the peripheral blood cells of systemic sclerosis patients. *Rheumatology* (Oxford) 45, 694-702 (2006).

van Bon et al. Proteome-wide analysis and CXCL4 as a biomarker in systemic sclerosis. *N Engl J Med* 370, 433-443 (2014).

van den Hoogen et al., 2013 classification criteria for systemic sclerosis: an American College of Rheumatology/European League against Rheumatism collaborative initiative. *Arthritis Rheum* 65, 2737-2747 (2013).

Varga and Abraham, Systemic sclerosis: a prototypic multisystem fibrotic disorder. *J Clin Invest* 117, 557-567 (2007).

Wenzel and Tuting, An IFN-Associated Cytotoxic Cellular Immune Response against Viral, Self-, or Tumor Antigens Is a Common Pathogenetic Feature in "Interface Dermatitis". *J Invest Dermatol* 128, 2392-2402 (2008).

Yamamoto et al., Animal model of sclerotic skin. I: Local injections of bleomycin induce sclerotic skin mimicking scleroderma. *J Invest Dermatol* 112, 456-462 (1999).

Yamamoto and Nishioka, Role of monocyte chemoattractant protein-1 and its receptor, CCR-2, in the pathogenesis of bleomycin-induced scleroderma. *J Invest Dermatol* 121, 510-516 (2003).

The invention claimed is:

1. A method of activating an immune response in a subject, comprising administering to the subject a therapeutically effective amount of a chemokine CXCL4, wherein the chemokine CXCL4 potentiates the response of toll-like receptor (TLR) 9 to produce interferon-α in plasmacytoid dendritic cells from the subject and the activation of the immune response is beneficial to treating cancer.

2. The method of claim 1, wherein the cancer is chosen from the group consisting of lung cancer, colon cancer, melanoma, pancreatic cancer, mammary cancer, prostate cancer, breast cancer, ovarian cancer, basal cell carcinoma, biliary tract cancer, bladder cancer, bone cancer, cervical cancer, colon and rectum cancer, connective tissue cancer, cancer of the digestive system, endometrial cancer, esophageal cancer, cancer of the head and neck, kidney cancer, larynx cancer, liver cancer, fibroma, neuroblastoma, oral cavity cancer, skin cancer, testicular cancer, thyroid cancer, uterine cancer, medulloblastoma, sarcoma, squamous cell carcinoma, and lymphoma.

3. The method of claim 1, wherein the CXCL4 is administered by injection directly into a tumor in the subject.

4. The method of claim 1, further comprising administering to the subject an agonist of TLR9.

5. The method of claim 4, wherein the agonist is chosen from the group consisting of CpG nucleotides, CpG-A, CpG-B and CpG-C.

6. The method of claim 4, further comprising administering to the subject a checkpoint inhibitor.

7. The method of claim 6, wherein the checkpoint inhibitor inhibits a protein chosen from the group consisting of CTLA-4, PD-L1, PD-L2, and PD-1.

8. The method of claim 1, wherein the CXCL4 is administered via the administration of plasmacytoid dendritic cells into tumor tissue in the subject, wherein the plasmacytoid dendritic cells have been contacted ex vivo with the chemokine peptide or protein and further contacted with an agonist of TLR9.

9. The method of claim 8, wherein the plasmacytoid dendritic cells were obtained from the subject.

10. The method of claim 8, wherein the TLR9 agonist is chosen from the group consisting of CpG nucleotides, CpG-A, CpG-B and CpG-C.

\* \* \* \* \*

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial Sequence
<220> FEATURE:
<223> OTHER INFORMATION: synthetic primer

<400> SEQUENCE: 1
cactgcccaa ctgatagcca                                          20

<210> SEQ ID NO 2
<211> LENGTH: 21
<212> TYPE: DNA
<213> ORGANISM: Artificial Sequence
```

```
<220> FEATURE:
<223> OTHER INFORMATION: synthetic primer

<400> SEQUENCE: 2
agccaacatg taacaccaag c                                          21

<210> SEQ ID NO 3
<211> LENGTH: 24
<212> TYPE: DNA
<213> ORGANISM: Artificial Sequence
<220> FEATURE:
<223> OTHER INFORMATION: synthetic primer

<400> SEQUENCE: 3
ttacctggat ggaaaccagc tact                                       24

<210> SEQ ID NO 4
<211> LENGTH: 24
<212> TYPE: DNA
<213> ORGANISM: Artificial Sequence
<220> FEATURE:
<223> OTHER INFORMATION: synthetic primer

<400> SEQUENCE: 4
tcaaggctga gaagctgtaa gcta                                       24

<210> SEQ ID NO 5
<211> LENGTH: 31
<212> TYPE: DNA
<213> ORGANISM: Artificial Sequence
<220> FEATURE:
<223> OTHER INFORMATION: synthetic primer

<400> SEQUENCE: 5
aactttctat gatgcttaca tttcttatga c                               31

<210> SEQ ID NO 6
<211> LENGTH: 20
<212> TYPE: DNA
<213> ORGANISM: Artificial Sequence
<220> FEATURE:
<223> OTHER INFORMATION: synthetic primer

<400> SEQUENCE: 6
ggtggtagcg cagctcattt                                            20

<210> SEQ ID NO 7
<211> LENGTH: 21
<212> TYPE: DNA
<213> ORGANISM: Artificial Sequence
<220> FEATURE:
<223> OTHER INFORMATION: synthetic primer

<400> SEQUENCE: 7
tgaagacttc aggcccaact g                                          21

<210> SEQ ID NO 8
<211> LENGTH: 19
<212> TYPE: DNA
<213> ORGANISM: Artificial Sequence
<220> FEATURE:
<223> OTHER INFORMATION: synthetic primer

<400> SEQUENCE: 8
tgcacggtca ccaggttgt                                             19
```

<210> SEQ ID NO 9
<211> LENGTH: 22
<212> TYPE: DNA
<213> ORGANISM: Artificial Sequence
<220> FEATURE:
<223> OTHER INFORMATION: synthetic primer

<400> SEQUENCE: 9
tttgatctgc cctggtatct ca                                              22

<210> SEQ ID NO 10
<211> LENGTH: 26
<212> TYPE: DNA
<213> ORGANISM: Artificial Sequence
<220> FEATURE:
<223> OTHER INFORMATION: synthetic primer

<400> SEQUENCE: 10
agttgttctt gggttgtttt cctaac                                          26

<210> SEQ ID NO 11
<211> LENGTH: 19
<212> TYPE: DNA
<213> ORGANISM: Artificial Sequence
<220> FEATURE:
<223> OTHER INFORMATION: synthetic primer

<400> SEQUENCE: 11
cacttggtcc tgcgcttga                                                  19

<210> SEQ ID NO 12
<211> LENGTH: 19
<212> TYPE: DNA
<213> ORGANISM: Artificial Sequence
<220> FEATURE:
<223> OTHER INFORMATION: synthetic primer

<400> SEQUENCE: 12
cacttggtcc tgcgcttga                                                  19

<210> SEQ ID NO 13
<211> LENGTH: 19
<212> TYPE: DNA
<213> ORGANISM: Artificial Sequence
<220> FEATURE:
<223> OTHER INFORMATION: synthetic primer

<400> SEQUENCE: 13
tgccaggcct ttacacagc                                                  19

<210> SEQ ID NO 14
<211> LENGTH: 20
<212> TYPE: DNA
<213> ORGANISM: Artificial Sequence
<220> FEATURE:
<223> OTHER INFORMATION: synthetic primer

<400> SEQUENCE: 14
tcggcgtcat ttagcacttg                                                 20

<210> SEQ ID NO 15
<211> LENGTH: 25
<212> TYPE: DNA
<213> ORGANISM: Artificial Sequence
<220> FEATURE:
<223> OTHER INFORMATION: synthetic primer

```
<400> SEQUENCE: 15
tggctattaa ttattcggtc tgcat                                              25

<210> SEQ ID NO 16
<211> LENGTH: 24
<212> TYPE: DNA
<213> ORGANISM: Artificial Sequence
<220> FEATURE:
<223> OTHER INFORMATION: synthetic primer

<400> SEQUENCE: 16
gcaagtggct agagtgcaga gtaa                                               24
```